(12) United States Patent
Gaur

(10) Patent No.: US 7,563,601 B1
(45) Date of Patent: Jul. 21, 2009

(54) ARTIFICIAL RIBOSWITCH FOR CONTROLLING PRE-MRNA SPLICING

(75) Inventor: Rajesh K. Gaur, Glendora, CA (US)

(73) Assignee: City of Hope, Duarte, CA (US)

( * ) Notice: Subject to any disclaimer, the term of this patent is extended or adjusted under 35 U.S.C. 154(b) by 308 days.

(21) Appl. No.: 11/446,527

(22) Filed: Jun. 1, 2006

Related U.S. Application Data

(60) Provisional application No. 60/686,838, filed on Jun. 1, 2005.

(51) Int. Cl.
  C12Q 1/68      (2006.01)
  C12P 19/34     (2006.01)
  C07H 21/02     (2006.01)
  C07H 21/04     (2006.01)

(52) U.S. Cl. .................. 435/91.1; 435/6; 435/91.31; 536/23.1

(58) Field of Classification Search ............ 435/6, 435/91.1, 375, 91.31; 514/1, 2, 44; 536/23.1, 536/24, 24.3, 24.5
See application file for complete search history.

(56) References Cited

OTHER PUBLICATIONS

Opalinska, J.B. et al., Nature Reviews, vol. 1, pp. 503-514 (2002).*
Peracchi, A. et al., Rev. Med. Virol., vol. 14, pp. 47-64 (2004).*
Chriila, T. et al., Biomaterials, vol. 23, pp. 321-342 (2002).*
Agrawal, S. et al., Molecular med. Today, vol. 6, pp. 72-81 (2000).*
Branch, A., Trends in Biochem. Sci., vol. 23, pp. 45-40 (1998).*
Crooke, S. Antisense Res. & Application, Chapter 1, pp. 1-50 (Springer-Verlag, Publ.) S. Crooke, Ed) (1998).*
Aebi, M., Hornig, H., Padgett, R.A., Reiser, J. and Weissmann, C. (1986) Sequence requirements for splicing of higher eukaryotic nuclear pre-mRNA. *Cell* 47:555-565.
Aurup, H., Williams, D. and Eckstein, F. (1992) 2'-Fluoro- and 2'-amino-2'-deoxynucleoside 5'-triphosphates as substrates for T7 RNA polymerase. *Biochemistry* 31:9636-9641.
Banerjee, H., Rahn, A., Davis, W. and Singh, R. (2003) Sex lethal and U2 small nuclear ribonucleoprotein auxiliary factor (U2AF$^{65}$) recognize polypyrimidine tracts using multiple modes of binding. *RNA* 9:88-99.
Belshaw, P.J., Ho, S.N., Crabtree, G.R. and Schreiber, S.L. (1996) Controlling protein association and subcellular localization with a synthetic ligand that induces heterodimerization of proteins. *Proc. Natl. Acad. Sci.* USA 93:4604-4607.
Bevers, S., Ha S.B. and McLaughlin, L.W. (1999) Critical nature of a specific uridine $O^2$ -carbonyl for cleavage by the hammerhead ribozyme. *Biochemistry* 38:7710-7718.
Black, D. L. (2003) Mechanisms of alternative pre-messenger RNA splicing. *Annu. Rev. Biochem.* 72:291-336.
Boggs, R.T., Gregor, P., Idriss, S., Belote, J.M. and McKeown, M. (1987) Regulation of sexual differentiation in D. melanogaster via alternative splicing of RNA from the transformer gene. *Cell* 50:739-747.

Bunch, T.A., Grinblat, Y. and Goldstein, L.S. (1988) Characterization and use of the Drosophila metallothionein promoter in cultured Drosophila melanogaster cells. *Nucleic Acids Res.* 16:1043-1061.
Buratti, E., Muro, A.F., Giombi, M., Gherbassi, D., Iaconcig, A. and Baralle, F.E. (2004) RNA folding affects the recruitment of SR proteins by mouse and human polypurinic enhancer elements in the fibronectin EDA exon. *Mol. Cell. Biol.* 24:1387-1400.
Burgstaller, P. and Famulok, M. (1994) Isolation of RNA aptamers for biological cofactors by in vitro selection. *Angew. Chem. Int. Ed. Engl.* 33:1084-1087.
Cartegni, L. and Krainer, A.R. (2003) Correction of disease-associated exon skipping by synthetic exon-specific activators. *Nat. Struct. Biol.* 10:120-125.
Chen, Z., Monia, B.P. and Corey, D.R. (2002) Telomerase inhibition, telomere shortening, and decreased cell proliferation by cell permeable 2'-O-methoxyethyl oligonucleotides. *J Med. Chem.* 45:5423-5425.
Chiara, M.D., Palandjian, L., Feld Kramer, R. and Reed, R. (1997) Evidence that U5 snRNP recognizes the 3' splice site for catalytic step II in mammals. *EMBO J* 16:4746-4759.
Chua, K. and Reed, R. (2001) An upstream AG determines whether a downstream AG is selected during catalytic step II of splicing. *Mol. Cell. Biol.* 21:1509-1514.
Claverie, J.M. (2001) Gene number. What if there are only 30,000 human genes? *Science* 291:1255-1257.
Cline, T.W. and Meyer, B.J. (1996) Vive la difference: males vs females in flies vs worms. *Annu. Rev. Genet.* 30:637-702.
Collins, C.A. and Guthrie, C. (1999) Allele-specific genetic interactions between Prp8 and RNA active site residues suggest a function for Prp8 at the catalytic core of the spliceosome. *Genes Dev.* 13:1970-1982.
Collins, C.A. and Guthrie, C. (2001) Genetic interactions between the 5' and 3' splice site consensus sequences and U6 snRNA during the second catalytic step of pre-mRNA splicing. *RNA* 7:1845-1854.
Das, R. and Reed, R. (1999) Resolution of the mammalian E complex and the ATP-dependent spliceosomal complexes on native agarose mini-gels. *RNA* 5:1504-1508.
Deirdre, A., Scadden, J. and Smith, C.W. (1995) Interactions between the terminal bases of mammalian introns are retained in inosine-containing pre-mRNAs. *EMBO J* 14:3236-3246.
Dignam, J.D., Lebovitz, R.M. and Roeder, R.G. (1983) Accurate transcription initiation by RNA polymerase II in a soluble extract from isolated mammalian nuclei. *Nucleic Acids Res.* 11:1475-1489.

(Continued)

*Primary Examiner*—Jane Zara
(74) *Attorney, Agent, or Firm*—Perkins Coie LLP; James J. Zhu

(57) ABSTRACT

The present invention relates to riboswitches that have been engineered to regulate pre-mRNA splicing. In particular, the insertion of a high affinity theophylline binding aptamer into the 3' splice site region, 5' splice site region, or branchpoint sequence (BPS) of a pre-mRNA modulates RNA splicing in the presence of theophylline. Accordingly, the aspects of the present invention include, but are not limited to, theophylline-dependent riboswitches which modulate RNA splicing, methods of modulating RNA splicing using theophylline and its corresponding riboswitches, methods of improving/identifying theophylline-dependent riboswitches, methods of treating diseases associated with or caused by abnormal RNA splicing.

5 Claims, 37 Drawing Sheets

OTHER PUBLICATIONS

Dominski, Z. and Kole, R. (1993) Restoration of correct splicing in thalassemic pre-mRNA by antisense oligonucleotides. *Proc. Natl. Acad. Sci.* USA 90:8673-8677.

Dredge, B.K., Polydorides, A.D. and Darnell, R.B. (2001) The splice of life: alternative splicing and neurological disease. *Nat. Rev. Neurosci.* 2:43-50.

Duconge, F. and Toulme, J.J. (1999) In vitro selection identifies key determinants for loop-loop interactions: RNA aptamers selective for the TAR RNA element of HIV-1. *RNA* 5:1605-1614.

Eder, P.S., DeVine, R.J., Dagle, J.M. and Walder, J.A. Substrate specificity and kinetics of degradation of antisense oligonucleotides by a 3' exonuclease in plasma. *Antisense Res. Dev.*, 1:141-151 (1991).

Endo, M., Mitsui, T., Okuni, T., Kimoto, M., Hirao, I. and Yokoyama, S. (2004) Unnatural base pairs mediate the site-specific incorporation of an unnatural hydrophobic component into RNA transcripts. *Bioorg. Med. Chem. Lett.* 14:2593-2596.

Eperon, I.C. and Muntoni, F. (2003) Can a 'patch' in a skipped exon make the pre-mRNA splicing machine run better? *Trends Mol. Med.* 9:233-234.

Eperon, L. P., Graham, I.R., Griffiths, A.D. and Eperon, I.C. (1988) Effects of RNA secondary structure on alternative splicing of pre-mRNA: is folding limited to a region behind the transcribing RNA polymerase? *Cell* 54:393-401.

Faustino, N.A. and Cooper, T.A. (2003) Pre-mRNA splicing and human disease. *Genes Dev.* 17:419-437.

Freyer, G.A., Arenas, J., Perkins, K.K., Furneaux, H.M., Pick, L., Young, B., Roberts, R.J. and Hurwitz, J. (1987) In vitro formation of a lariat structure containing a $G^{2'}-{}^{5'}G$ linkage. *J Biol. Chem.* 262:4267-4273.

Garcia-Blanco, M.A., Baraniak, A.P. and Lasda, E.L. (2004) Alternative splicing in disease and therapy. *Nat. Biotechnol.* 22:535-546.

Gaur, R.K., McLaughlin, L.W. and Green, M.R. (1997) Functional group substitutions of the branchpoint adenosine in a nuclear pre-mRNA and a group II intron. *RNA* 3:861-869.

Gaur, R.K., Valcarcel, J. and Green, M.R. (1995) Sequential recognition of the pre-mRNA branch point by U2AF[65] and a novel spliceosome-associated 28-kDa protein. *RNA* 1:407-417.

Goguel, V. and Rosbash, M. (1993) Splice site choice and splicing efficiency are positively influenced by pre-mRNA intramolecular base pairing in yeast. *Cell* 72:893-901.

Goguel, V., Wang, Y. and Rosbash, M. (1993) Short artificial hairpins sequester splicing signals and inhibit yeast pre-mRNA splicing. *Mol. Cell. Biol.* 13:6841-6848.

Goodall, G.J. and Filipowicz, W. (1991) Different effects of intron nucleotide composition and secondary structure on pre-mRNA splicing in monocot and dicot plants. *EMBO J* 10:2635-2644.

Gottesfeld, J.M., Neely, L., Trauger, J.W., Baird, E.E. and Dervan, P.B. (1997) Regulation of gene expression by small molecules. *Nature* 387:202-205.

Gozani, O., Patton, J.G. and Reed, R. (1994) A novel set of spliceosome-associated proteins and the essential splicing factor PSF bind stably to pre-mRNA prior to catalytic step II of the splicing reaction. *EMBO J* 13:3356-3367.

Granadino, B., Penalva, L.O., Green, M.R., Valcarcel, J. and Sanchez, L. (1997) Distinct mechanisms of splicing regulation in vivo by the Drosophila protein Sex-lethal. *Proc. Natl. Acad. Sci.* USA 94:7343-7348.

Graveley, B.R. (2001) Alternative splicing: increasing diversity in the proteomic world. *Trends Genet.* 17:100-107.

Graveley, B.R. (2005) Small molecule control of pre-mRNA splicing. *RNA* 11:355-358.

Guschlbauer, W. (1980) Conformational analysis of ribonucleosides from proton-proton coupling constants. *Biochim. Biophys. Acta.* 610:47-55.

Heidenreich, O., Benseler, F., Fahrenholz, A. and Eckstein, F. (1994) High activity and stability of hammerhead ribozymes containing 2'-modified pyrimidine nucleosides and phosphorothioates. *J Biol. Chem.* 269:2131-2138.

Heidenreich, O., Kang, S.H., Xu, X. and Nerenberg, M. (1995) Application of antisense technology to therapeutics. *Mol. Med. Today* 1:128-133.

Ho, S.N., Biggar, S.R., Spencer, D.M., schreiber, S.L. and Crabtree, G.R. (1996) Dimeric ligands define a role for transcriptional activation domains in reinitiation. *Nature* 382:822-826.

Hornig, H., Aebi, M. and Weissmann, C. (1986) Effect of mutations at the lariat branch acceptor site on β-globin pre-mRNA splicing in vitro. *Nature* 324:589-591.

Huang, Z. and Szostak, J.W. (2003) Evolution of aptamers with a new specificity and new secondary structures from an ATP aptamer. *RNA* 9:1456-1463.

Hull, J., Shackleton, S. and Harris, A. (1993) Abnormal mRNA splicing resulting from three different mutations in the CFTR gene. *Hum. Mol. Genet.* 2:689-692.

Inoue, K., Hoshijima, K., Sakamoto, H. and Shimura, Y. (1990) Binding of the Drosophila sex-lethal gene product to the alternative splice site of transformer primary transcript. *Nature* 344:461-463.

Jenison, R.D., Gill, S.C., Pardi, A. and Polisky, B. (1994) High-resolution molecular discrimination by RNA. *Science* 263:1425-1429.

Johnson, J.M., Castle, J., Garrett-Engele, P., Kan, Z., Loerch, P.M., Armour, C.D., Santos, R., Schadt, E.E., Stoughton, R. and Shoemaker, D.D. (2003) Genome-wide survey of human alternative pre-mRNA splicing with exon junction microarrays. *Science* 302:2141-2144.

Joyce, G.F. (1994) In vitro evolution of nucleic acids. *Curr. Opin. Struct. Biol.* 4:331-336.

Kan, Z., Rouchka, E.C., Gish, W.R. and States, D.J. (2001) Gene structure prediction and alternative splicing analysis using genomically aligned ESTs. *Genome Res.* 11:889-900.

Kandels-Lewis, S. and Seraphin, B. (1993) Role of U6 snRNA in 5' splice site selection. *Science* 262:2035-2039.

Kawasaki, A.M., Casper, M.D., Freier, S.M., Lesnik, E.A., Zounes, M.C., Cummins, L.L., Gonzalez, C. and Cook, P.D. (1993) Uniformly modified 2'-deoxy-2'-fluoro phosphorothioate oligonucleotides as nuclease-resistant antisense compounds with high affinity and specificity for RNA targets. *J Med. Chemistry* 36:831-841.

Konarska, M.M. and Sharp, P.A. (1986) Electrophoretic separation of complexes involved in the splicing of precursors to mRNAs. *Cell* 46:845-855.

Konforti, B.B., Koziolkiewicz, M.J. and Konarska, M.M. (1993) Disruption of base pairing between the 5' splice site and the 5' end of U1 snRNA is required for spliceosome assembly. *Cell* 75:863-873.

Krainer, A.R., Maniatis, T., Ruskin, B. and Green, M.R. (1984) Normal and mutant human beta-globin pre-mRNAs are faithfully and efficiently spliced in vitro. *Cell* 36:993-1005.

Krajewska, M., Fenoglio-Preiser, C.M., Krajewski, S., Song, K., Macdonald, J.S., Stemmerman, G. and Reed, J.C. (1996a) Immunohistochemical analysis of Bcl-2 family proteins in adenocarcinomas of the stomach. *Am. J Pathol.* 149:1449-1457.

Krajewska, M., Krajewski, S., Epstein, J.I., Shabaik, A., Sauvageot, J., Song, K., Kitada, S. and Reed, J.C. (1996b) Immunohistochemical analysis of bcl-2, bax, bcl-X, and mcl-1 expression in prostate cancers. *Am. J Pathol.* 148:1567-1576.

Kramer, A. (1996) The structure and function of proteins involved in mammalian pre-mRNA splicing. *Annu. Rev. Biochem.* 65:367-409.

Kubik, M.F., Bell, C., Fitzwater T., Watson, S.R., Tasset, D.M. (1997) Isolation and characterization of 2'-fluoro-, 2'-fluoro-, 2'-amino-, and 2'-fluoro-/amino-modified RNA ligands to human IFN-γ that inhibit receptor binding. *J. Immunol.* 159:259-267.

Kurreck, J. (2003) Antisense technologies. Improvement through novel chemical modifications. *Eur. J Biochem.* 270:1628-1644.

Kuwabara, T., Warashina, M., Tanabe, T., Tani, K., Asano, S. and Taira, K. (1998) A novel allosterically trans-activated ribozyme, the maxizyme, with exceptional specificity in vitro and in vivo. *Mol. Cell. Biol.* 2:617-627.

Kuznetsova, M., Novopashina, D., Repkova, M., Venyaminova, A. and Vlassov, V. (2004) Binary hammerhead ribozymes with high cleavage activity. *Nucleosides, Nucleotides & Nucleic Acids* 23:1037-1042.

Lamond, A.I., Konarska, M.M. and Sharp, P.A. (1987) A mutational analysis of spliceosome assembly: evidence for splice site collaboration during spliceosome formation. *Genes Dev.* 1:532-543.

Lesser, C. and Guthrie, C. (1993) Mutations in U6 snRNA that alter splice site specificity: implications for the active site. *Science* 262:1982-1988.

Lian, Y. and Garner, H.R. (2005) Evidence for the regulation of alternative splicing via complementary DNA sequence repeats. *Bioinformatics* 21:1358-1364.

Liu, H.-X., Goodall, G.J., Kole, R. and Filipowicz, W. (1995) Effects of secondary structure on pre-mRNA splicing: hairpins sequestering the 5' but not the 3' splice site inhibit intron processing in *Nicotiana plumbaginifolia*. *EMBO J* 14:377-388.

Liu, Z.-R., Laggerbauer, B., Luhrmann, R. and Smith, C.W. (1997) Crosslinking of the U5 snRNP-specific 116-kDa protein to RNA hairpins that block step 2 of splicing. *RNA* 3:1207-1219.

Lopez, A.J. (1998) Alternative splicing of pre-mRNA: developmental consequences and mechanisms of regulation. *Annu. Rev. Genet.* 32:279-305.

Luukkonen, B.G. and Seraphin, B. (1997) The role of branchpoint-3' splice site spacing and interaction between intron terminal nucleotides in 3' splice site selection in Saccharomyces cerevisiae. *EMBO J* 16:779-792.

Malca, H., Shomron, N. and Ast, G. (2003) The U1 snRNP base pairs with the 5' splice site within a penta-snRNP complex. *Mol. Cell. Biol.* 23:3442-3455.

Maniatis, T. and Tasic, B. (2002) Alternative pre-mRNA splicing and proteome expansion in metazoans. *Nature* 418:236-243.

Marshall, K.A. and Ellington, A.D. (2000) In vitro selection of RNA aptamers. *Methods Enzymol.* 318:193-214.

Merendino, L., Guth, S., Bilbao, D., Martinez, C. and Valcarcel, J. (1999) Inhibition of msl-2 splicing by Sex-lethal reveals interaction between U2AF$^{35}$ and the 3' splice site AG. *Nature* 402:838-841.

Mironov, A.A., Fickett, J.W. and Gelfand, M.S. (1999) Frequent alternative splicing of human genes. *Genome Res.* 9:1288-1293.

Modrek, B., Resch, A., Grasso, C. and Lee, C. (2001) Genome-wide detection of alternative splicing in expressed sequences of human genes. *Nucleic Acids Res.* 29:2850-2859.

Monia, B.P., Lesnik, E.A., Gonzalez, C., Lima, W.F., McGee, D., Guinosso, C.J., Kawasaki, A.M., Cook, P.D. and Freier, S.M. (1993) Evaluation of 2'-modified oligonucleotides containing 2'-deoxy gaps as antisense inhibitors of gene expression. *J Biol. Chem.* 268:14514-14522.

Moore, M.J., Query, C.C. and Sharp, P.A. (1993) Splicing of precursors to mRNA by the spliceosome. In Gesteland, R.F. and Atkins, J.R. (eds.), In the RNA world. Cold Spring Harbor, New York, pp. 303-357.

Moore, M.J. and Sharp, P.A. (1992) Site-specific modification of pre-mRNA: the 2'-hydroxyl groups at the splice sites. *Science* 256:992-997.

Newman, A. (1994) Activity in the spliceosome. *Curr. Biol.*, 4:462-464.

Newman, A.J., Lin, R.J., Cheng, S.C. and Abelson, J. (1985) Molecular consequences of specific intron mutations on yeast mRNA splicing in vivo and in vitro. *Cell* 42:335-344.

Nilsen, T.W. (2003) The spliceosome: the most complex macromolecular machine in the cell? *Bioessays* 25:1147-1149.

Nissim-Rafinia, M. and Kerem, B. (2002) Splicing regulation as a potential genetic modifier. *Trends Genet.* 18:123-127.

Novak, U., Grob, T.J., Baskaynak, G., Peters, U.R., Aebi, S., Zwahlen, D., Tschan, M.P., Kreuzer, K.A., Leibundgut, E.O., Cajot, J.F., Tobler, A. and Fey, M.F. (2001) Overexpression of the p73 gene is a novel finding in high-risk B-cell chronic lymphocytic leukemia. *Ann. Oncol.* 12:981-986.

Nudler, E. and Mironov, A.S. (2004) The riboswitch control of bacterial metabolism. *Trends Biochem Sci.* 29:11-17.

Pagani, F. and Baralle, F.E. (2004) Genomic variants in exons and introns: identifying the splicing spoilers. *Nat Rev. Genet.* 5:389-396.

Parker, R. and Siliciano, P.G. (1993) Evidence for an essential non-Watson-Crick interaction between the first and last nucleotides of a nuclear pre-mRNA intron. *Nature* 361:660-662.

Patterson, B. and Guthrie, C. (1991) A U-rich tract enhances usage of an alternative 3' splice site in yeast. *Cell* 64:181-187.

Phillips, A. and Cooper, T. (2000) RNA processing and human disease. *Cell. Mol. Life Sci.* 57:235-249.

Pieken, W.A., Olsen, D.B., Benseler, F., Aurup, H. and Eckstein, F. (1991) Kinetic characterization of ribonuclease-resistant 2'- modified hammerhead ribozymes. *Science* 253:314-317.

Proctor, D.J., Ma, H., Kierzek, E., Kierzek, R., Gruebele, M. and Bevilacqua, P.C. (2004) Folding thermodynamics and kinetics of YNMG RNA hairpins: specific incorporation of 8-bromoguanosine leads to stabilization by enhancement of the folding rate. *Biochemistry* 43:14004-14014.

Query, C.C., Moore, M.J. and Sharp, P.A. (1994) Branch nucleophile selection in pre-mRNA splicing: evidence for the bulged duplex model. *Genes & Dev.* 8:587-597.

Reed, R. and Palandjian, L. (1997) Spliceosome assembly. In Krainer, A. (ed.), Eukaryotic mRNA Processing. IRL Press, Oxford, pp. 103-129.

Roberts, G.C. and Smith, C.W. (2002) Alternative splicing: combinatorial output from the genome. *Curr. Opin. Chem. Biol.* 6:375-383.

Ruskin, B. and Green, M.R. (1985) Role of the 3' splice site consensus sequence in mammalian pre-mRNA splicing. *Nature* 317:732-734.

Ruskin, B., Zamore, P.D. and Green, M.R. (1988) A factor, U2AF, is required for U2 snRNP binding and splicing complex assembly. *Cell* 52:207-219.

Ryner, L.C. and Baker, B.S. (1991) Regulation of doublesex pre-mRNA processing by 3' splice site activation. *Genes & Dev.*, 5:2071-2085.

Sakamoto, H., Inoue, K., Higuchi, I., Ono, Y. and Shimura, Y. (1992) Control of Drosophila Sex-lethal pre-mRNA splicing by its own female- specific product. *Nucleic Acids Res.* 20:5533-5540.

Sassanfar, M. and Szostak, J.W. (1993) An RNA motif that binds ATP. *Nature* 364:550-553.

Sawa, H. and Abelson, J. (1992) Evidence for a base-pairing interaction between U6 small nuclear RNA and the 5' splice site during the splicing reaction in yeast. *Proc. Natl. Sci.* USA 89:11269-11273.

Sawa, H. and Shimura, Y. (1992) Association of U6 snRNA with the 5'-splice site region of pre-mRNA in the spliceosome. *Genes & Dev.* 6:244-254.

Seraphin, B., Kretzner, L. and Rosbash, M. (1988) A U1 snRNA:pre-mRNA base pairing interaction is required early in yeast spliceosome assembly but does not uniquely define the 5' cleavage site. EMBO J. 7:2533-2538.

Seraphin, B. and Rosbash, M. (1990) Exon mutations uncouple 5' splice site selection from U1 snRNA pairing. *Cell* 63:619-629.

Shaw, J.P., Kent, K., Bird, J., Fishback, J. and Froehler, B. (1991) Modified deoxyoligonucleotides stable to exonuclease degradation in serum. *Nucleic Acids Res.* 19:747-750.

Shomron, N. and Ast, G. (2003) Boric acid reversibly inhibits the second step of pre-mRNA splicing. *FEBS Lett.* 552:219-224.

Shomron, N., Malca, H., Vig, I. and Ast, G. (2002) Reversible inhibition of the second step of splicing suggests a possible role of zinc in the second step of splicing. *Nucleic Acids Res.* 30:4127-4137.

Siliciano, P.G. and Guthrie, C. (1988) 5' splice site selection in yeast: genetic alterations in base-pairing with U1 reveal additional requirements. *Genes & Dev.* 2:1258-1267.

Singh, R., Banerjee, H. and Green, M.R. (2000) Differential recognition of the polypyrimidine-tract by the general splicing factor U2AF65 and the splicing repressor sex-lethal. *RNA* 6:901-911.

Singh, R., Valcarcel, J. and Green, M.R. (1995) Distinct binding specificities and functions of higher eukaryotic polypyrimidine tract-binding proteins. *Science* 268:1173-1176.

Skordis, L.A., Dunckley, M.G., Yue, B., Eperon, I.C. and Muntoni, F. (2003) Bifunctional antisense oligonucleotides provide a trans-acting splicing enhancer that stimulates SMN2 gene expression in patient fibroblasts. *Proc. Natl. Acad. Sci.* USA 100:4114-4119.

Smith, C.W. and Valcarcel, J. (2000) Alternative pre-mRNA splicing: the logic of combinatorial control. *Trends Biochem. Sci.* 25:381-388.

Solnick, D. (1985) Alternative splicing caused by RNA secondary structure. *Cell* 43:667-676.

Sontheimer, E. and Steitz, J.A. (1993) The U5 and U6 small nuclear RNAs as active site components of the spliceosome. *Science* 262:1989-1996.

Sosnowski, B.A., Belote, J.M. and McKeown, M. (1989) Sex-specific alternative splicing of RNA from the transformer gene results from sequence-dependent splice site blockage. *Cell* 58:449-459.

Soukup, G.A. and Breaker, R.R. (1999a) Engineering precision RNA molecular switches. *Proc. Natl. Acad. Sci.* USA 96:3584-3589.

Soukup, G.A. and Breaker, R.R. (1999b) Nucleic acid molecular switches. *Trends Biotechnol.* 17:469-476.

Soukup, G.A., Emilsson, G.A. and Breaker, R.R. (2000) Altering molecular recognition of RNA aptamers by allosteric selection. *J Mol. Biol.* 298:623-632.

Staley, J.P. and Guthrie, C. (1998) Mechanical devices of the spliceosome: motors, clocks, springs, and things. *Cell* 92:315-326.

Steinman, H.A., Burstein, E., Lengner, C., Gosselin, J., Pihan, G., Duckett, C.S. and Jones, S.N. (2004) An alternative splice form of Mdm2 induces p53-independent cell growth and tumorigenesis. *J Biol. Chem.* 279:4877-4886.

Stevens, S.W., Ryan, D.E., Ge, H.Y., Moore, R.E., Young, M.K., Lee, T.D. and Abelson, J. (2002) Composition and functional characterization of the yeast spliceosomal penta-snRNP. *Mol. Cell* 9:31-44.

Tanaka, K., Watakabe, A. and Shimura, Y. (1994) Polypurine sequences within a downstream exon function as a splicing factor. *Mol. Cell. Biol.* 14:1347-1354.

Thanaraj, T.A., Stamm, S., Clark, F., Riethoven, J.J., Le Texier, V. and Muilu, J. (2004) ASD: the Alternative Splicing Database. *Nucleic Acids Res.* 32 Database issue, D64-69.

Tsuji, H., Nomiyama, K., Murai, K., Akagi, K. and Fujishima, M. (1992) Comparison of the properties of ribonucleases in human liver tissue and serum. *Eur. J Clin. Chem. Clin. Biochem.* 30:339-341.

Umen, J.G. and Guthrie, C. (1995) The second catalytic step of pre-mRNA splicing. *RNA* 1:869-885.

Valcarcel, J., Gaur, R.K., Singh, R. and Green, M.R. (1996) Interaction of U2AF[65] RS region with pre-mRNA branch point and promotion of base pairing with U2 snRNA. *Science* 273:1706-1709.

Valcarcel, J., Singh, R., Zamore, P.D. and Green, M.R. (1993) The protein Sex-lethal antagonizes the splicing factor U2AF to regulate alternative splicing of transformer pre-mRNA. *Nature* 362:171-175.

van Nues, R. W. and Beggs, J.D. (2001) Functional contacts with a range of splicing proteins suggest a central role for Brr2p in the dynamic control of the order of events in spliceosomes of *Saccharomyces cerevisiae. Genetics* 157:1451-1467.

Venables, J.P. (2004) Aberrant and alternative splicing in cancer. *Cancer Res.* 64:7647-7654.

Villemaire, J., Dion, I., Elela, S.A. and Chabot, B. (2003) Reprogramming alternative pre-messenger RNA splicing through the use of protein-binding antisense oligonucleotides. *J Biol. Chem.* 278:50031-50039.

Vorlter, L.C. and Eckstein, F. (2000) Phosphorothioate modification of RNA for stereochemical and interference analyses. *Methods Enzymol.* 317:74-91.

Wallis, M.G., von Ahsen, U., Schroeder, R. and Famulok, M. (1995) A novel RNA motif for neomycin recognition. *Chem. & Biol.* 2:543-552.

Wang, Y. and Rando, R.R. (1995) Specific binding of aminoglycoside antibiotics to RNA. *Chem. & Biol.* 2:281-290.

Wassarman, D.A. and Steitz, J.A. (1992) Interactions of small nuclear RNA's with precursor messenger RNA during in vitro splicing. *Science* 257:1918-1925.

Watakabe, A., Tanaka, K. and Shimura, Y. (1993) The role of exon sequences in splice site selection. *Genes & Dev.* 7:407-418.

Will, C.L. and Luhrmann, R. (1997) Protein functions in pre-mRNA splicing. *Curr. Opin. Cell. Biol.* 9:320-328.

Wu, S., Romfo, C.M., Nilsen, T.W. and Green, M.R. (1999) Functional recognition of the 3' splice site AG by the splicing factor U2AF35. *Nature* 402:832-835.

Xerri, L., Parc, P., Brousset, P., Schlaifer, D., Hassoun, J., Reed, J.C., Krajewski, S. and Birnbaum, D. (1996) Predominant expression of the long isoform of Bcl-x (Bcl-xL) in human lymphomas. *Br. J Haematol.* 92:900-906.

Zamore, P.D., Patton, J.G. and Green, M.R. (1992) Cloning and domain structure of the mammalian splicing factor U2AF. *Nature* 355:609-614.

Zhao, Y. and Baranger, A.M. (2003) Design of an adenosine analogue that selectively improves the affinity of a mutant U1A protein for RNA. *J Am. Chem. Soc.* 125:2480-2488.

Zhuang, Y. and Weiner, A.M. (1986) A compensatory base change in U1 snRNA suppresses a 5' splice site mutation. Cell 46:827-835.

Zillmann, M., Zapp, M.L. and Berget, S.M. (1988) Gel electrophoretic isolation of splicing complexes containing U1 small nuclear ribonucleoprotein particles. *Mol. Cell. Biol.* 8:814-821.

Zimmermann, G.R., Jenison, R.D., Wick, C.L., Simorre, J.P. and Pardi, A. (1997) Interlocking structural motifs mediate molecular discrimination by a theophylline-binding RNA. *Nat. Struct. Biol.* 4:644-649.

Zimmermann, G.R., Shields, T.P., Jenison, R.D., Wick, C.L. and Pardi, A. (1998) A semiconserved residue inhibits complex formation by stabilizing interactions in the free state of a theophylline-binding RNA. *Biochemistry* 37:9186-9192.

Zimmermann, G.R., Wick, C.L., Shields, T.P., Jenison, R.D. and Pardi, A. (2000) Molecular interactions and metal binding in the theophylline-binding core of an RNA aptamer. *RNA* 6:659-667.

Zorio, D.A. and Blumenthal, T. (1999) Both subunits of U2AF recognize the 3' splice site in *Caenorhabditis elegans. Nature* 402:835-838.

Zuker, M. (1989) Computer prediction of RNA structure. *Methods Enzymol.* 180:262-288.

\* cited by examiner

A.

B.

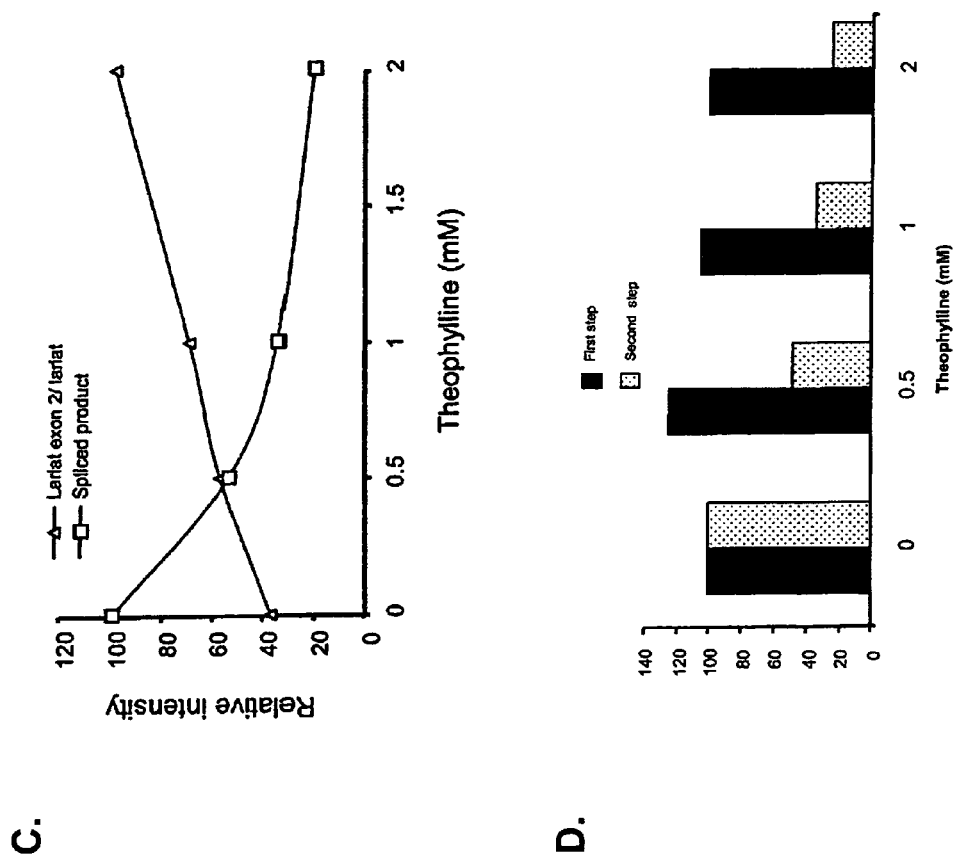
Figure 3 (con't.)

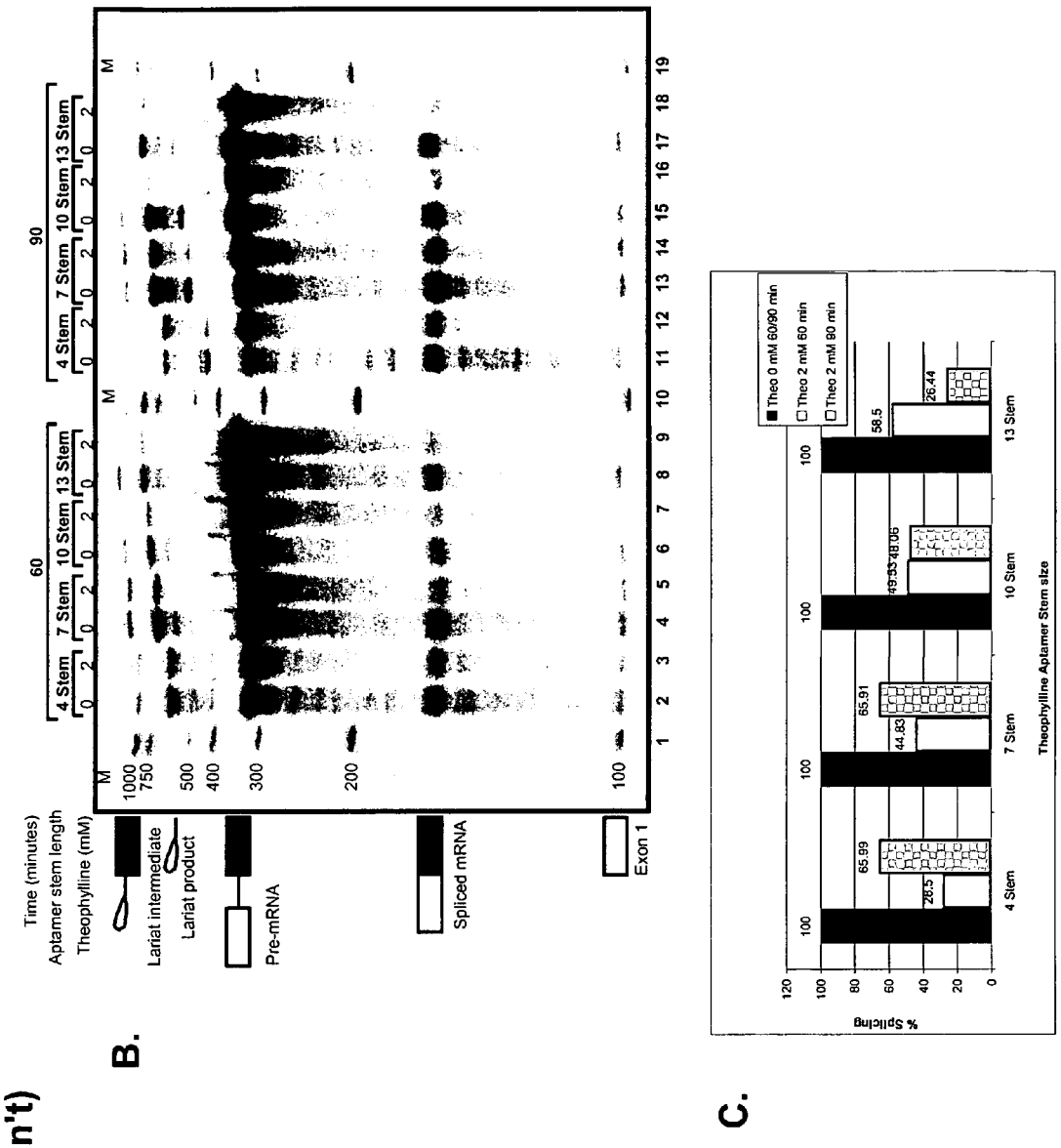
Figure 32 (con't)

SEQUENCE LISTING

```
<160> NUMBER OF SEQ ID NOS: 91

<210> SEQ ID NO 1
<211> LENGTH: 42
<212> TYPE: RNA
<213> ORGANISM: Artificial
<220> FEATURE:
<223> OTHER INFORMATION: Chemically synthesized riboswitch

<400> SEQUENCE: 1
acyyyyyyyy yyyyyyyaua ccagccgaaa ggcccuuggc ag                        42

<210> SEQ ID NO 2
<211> LENGTH: 48
<212> TYPE: RNA
<213> ORGANISM: Artificial
<220> FEATURE:
<223> OTHER INFORMATION: Chemically synthesized riboswitch

<400> SEQUENCE: 2
acyyyyyyyy yyyyyyyyy yyyauaccag ccgaaaggcc cuuggcag                   48
```

<210> SEQ ID NO 3
<211> LENGTH: 44
<212> TYPE: RNA
<213> ORGANISM: Artificial
<220> FEATURE:
<223> OTHER INFORMATION: Chemically synthesized riboswitch

<400> SEQUENCE: 3
acyyyyyyyy yyyyyyyyya uaccagccga aaggcccuug gcag                    44

<210> SEQ ID NO 4
<211> LENGTH: 47
<212> TYPE: RNA
<213> ORGANISM: Artificial
<220> FEATURE:
<223> OTHER INFORMATION: Chemically synthesized riboswitch

<400> SEQUENCE: 4
acuuuuuuuc uuuuuuuuuc cauaccagcc gaaaggcccu uggcagg                 47

<210> SEQ ID NO 5
<211> LENGTH: 48
<212> TYPE: RNA
<213> ORGANISM: Artificial
<220> FEATURE:
<223> OTHER INFORMATION: Chemically synthesized riboswitch

<400> SEQUENCE: 5
acuuuuuuuc uuuuuuuuuc cucauaccag ccgaaaggcc cuuggcag                48

<210> SEQ ID NO 6
<211> LENGTH: 52
<212> TYPE: RNA
<213> ORGANISM: Artificial
<220> FEATURE:
<223> OTHER INFORMATION: Chemically synthesized riboswitch

<400> SEQUENCE: 6
acuuuuuuuc uuuuuuuuuc cucauaccag ccgaaaggcc cuuggcagga gg           52

<210> SEQ ID NO 7
<211> LENGTH: 46
<212> TYPE: RNA
<213> ORGANISM: Artificial
<220> FEATURE:
<223> OTHER INFORMATION: Chemically synthesized riboswitch
<220> FEATURE:
<221> NAME/KEY: misc_feature
<222> LOCATION: (14)..(14)
<223> OTHER INFORMATION: complementary to nucleotide 46
<220> FEATURE:
<221> NAME/KEY: misc_feature
<222> LOCATION: (15)..(15)
<223> OTHER INFORMATION: complementary to nucleotide 45
<220> FEATURE:
<221> NAME/KEY: misc_feature
<222> LOCATION: (16)..(16)
<223> OTHER INFORMATION: complementary to nucleotide 44
<220> FEATURE:
<221> NAME/KEY: misc_feature
<222> LOCATION: (17)..(17)
<223> OTHER INFORMATION: complementary to nucleotide 43
<220> FEATURE:
<221> NAME/KEY: misc_feature
<222> LOCATION: (43)..(46)
<223> OTHER INFORMATION: n is a, c, g, or u

<400> SEQUENCE: 7
acyyyyyyyy yyyynnnnaua ccagccgaaa ggcccuuggc agnnnn                 46

```
<210> SEQ ID NO 8
<211> LENGTH: 46
<212> TYPE: RNA
<213> ORGANISM: Artificial
<220> FEATURE:
<223> OTHER INFORMATION: Chemically synthesized riboswitch
<220> FEATURE:
<221> NAME/KEY: misc_feature
<222> LOCATION: (14)..(14)
<223> OTHER INFORMATION: complementary to nucleotide 46
<220> FEATURE:
<221> NAME/KEY: misc_feature
<222> LOCATION: (15)..(15)
<223> OTHER INFORMATION: complementary to nucleotide 45
<220> FEATURE:
<221> NAME/KEY: misc_feature
<222> LOCATION: (16)..(16)
<223> OTHER INFORMATION: complementary to nucleotide 44
<220> FEATURE:
<221> NAME/KEY: misc_feature
<222> LOCATION: (17)..(17)
<223> OTHER INFORMATION: complementary to nucleotide 43
<220> FEATURE:
<221> NAME/KEY: misc_feature
<222> LOCATION: (43)..(46)
<223> OTHER INFORMATION: n is a, c, g, or u

<400> SEQUENCE: 8
acuuuuuuuu uuunnnnaua ccagccgaaa ggcccuuggc agnnnn            46

<210> SEQ ID NO 9
<211> LENGTH: 54
<212> TYPE: RNA
<213> ORGANISM: Artificial
<220> FEATURE:
<223> OTHER INFORMATION: Chemically synthesized riboswitch
<220> FEATURE:
<221> NAME/KEY: misc_feature
<222> LOCATION: (22)..(22)
<223> OTHER INFORMATION: complementary to nucleotide 54
<220> FEATURE:
<221> NAME/KEY: misc_feature
<222> LOCATION: (23)..(23)
<223> OTHER INFORMATION: complementary to nucleotide 53
<220> FEATURE:
<221> NAME/KEY: misc_feature
<222> LOCATION: (24)..(24)
<223> OTHER INFORMATION: complementary to nucleotide 52
<220> FEATURE:
<221> NAME/KEY: misc_feature
<222> LOCATION: (25)..(25)
<223> OTHER INFORMATION: complementary to nucleotide 51
<220> FEATURE:
<221> NAME/KEY: misc_feature
<222> LOCATION: (51)..(54)
<223> OTHER INFORMATION: n is a, c, g, or u

<400> SEQUENCE: 9
acyyyyyyyy yyyyyyyyyy ynnnnauacc agccgaaagg cccuuggcag nnnn    54

<210> SEQ ID NO 10
<211> LENGTH: 25
<212> TYPE: RNA
<213> ORGANISM: Artificial
<220> FEATURE:
<223> OTHER INFORMATION: Chemically synthesized theophylline-dependent
      aptamer

<400> SEQUENCE: 10
auaccagccg aaaggcccuu ggcag                                    25

<210> SEQ ID NO 11
```

```
<211> LENGTH: 38
<212> TYPE: RNA
<213> ORGANISM: Artificial
<220> FEATURE:
<223> OTHER INFORMATION: Chemically synthesized riboswitch sequence
      subject to optimization

<400> SEQUENCE: 11 acuuuuuuc cucauaccag ccgaaaggcc cuuggcag                                38

<210> SEQ ID NO 12
<211> LENGTH: 39
<212> TYPE: RNA
<213> ORGANISM: Artificial
<220> FEATURE:
<223> OTHER INFORMATION: Chemically synthesized riboswitch sequence
      subject to optimization

<400> SEQUENCE: 12
acuuuuuuuu ccucauacca gccgaaaggc ccuuggcag                              39

<210> SEQ ID NO 13
<211> LENGTH: 40
<212> TYPE: RNA
<213> ORGANISM: Artificial
<220> FEATURE:
<223> OTHER INFORMATION: Chemically synthesized riboswitch sequence
      subject to optimization

<400> SEQUENCE: 13
acuuuuuuuu uccucauacc agccgaaagg cccuuggcag                             40

<210> SEQ ID NO 14
<211> LENGTH: 41
<212> TYPE: RNA
<213> ORGANISM: Artificial
<220> FEATURE:
<223> OTHER INFORMATION: Chemically synthesized riboswitch sequence
      subject to optimization

<400> SEQUENCE: 14
acuuuuuuuu uuccucauac cagccgaaag gcccuuggca g                           41

<210> SEQ ID NO 15
<211> LENGTH: 42
<212> TYPE: RNA
<213> ORGANISM: Artificial
<220> FEATURE:
<223> OTHER INFORMATION: Chemically synthesized riboswitch sequence
      subject to optimization

<400> SEQUENCE: 15
acuuuuuuuu uuuccucaua ccagccgaaa ggcccuuggc ag                          42

<210> SEQ ID NO 16
<211> LENGTH: 33
<212> TYPE: RNA
<213> ORGANISM: Artificial
<220> FEATURE:
<223> OTHER INFORMATION: Chemically synthesized theophylline binding
      sequence
<220> FEATURE:
<221> NAME/KEY: misc_feature
<222> LOCATION: (5)..(10)
<223> OTHER INFORMATION: Required for theophylline binding
<220> FEATURE:
<221> NAME/KEY: misc_feature
<222> LOCATION: (21)..(29)
<223> OTHER INFORMATION: Required for theophylline binding
```

-continued

```
<400> SEQUENCE: 16
ggcgauacca gccgaaaggc ccuuggcagc guc                                33

<210> SEQ ID NO 17
<211> LENGTH: 24
<212> TYPE: RNA
<213> ORGANISM: Artificial
<220> FEATURE:
<223> OTHER INFORMATION: Chemically synthesized riboswitch

<400> SEQUENCE: 17
acccuguccc uuuuuuucc acag                                           24

<210> SEQ ID NO 18
<211> LENGTH: 62
<212> TYPE: RNA
<213> ORGANISM: Artificial
<220> FEATURE:
<223> OTHER INFORMATION: Chemically synthesized riboswitch

<400> SEQUENCE: 18
acccuuuccc uuuuuuucc ucucucucug gcgauaccag ccgaaaggcc cuuggcagcg    60
cc                                                                  62

<210> SEQ ID NO 19
<211> LENGTH: 51
<212> TYPE: RNA
<213> ORGANISM: Artificial
<220> FEATURE:
<223> OTHER INFORMATION: Chemically synthesized riboswitch

<400> SEQUENCE: 19
acuuuuuuuc uuuuuuuuuc agauaccagc cgaaaggccc uuggcagcug a            51

<210> SEQ ID NO 20
<211> LENGTH: 55
<212> TYPE: RNA
<213> ORGANISM: Artificial
<220> FEATURE:
<223> OTHER INFORMATION: Chemically synthesized riboswitch

<400> SEQUENCE: 20
acuuuuuuuc uuuuuuuuuc agggcgauac cagccgaaag gcccuuggca gcguc        55

<210> SEQ ID NO 21
<211> LENGTH: 22
<212> TYPE: RNA
<213> ORGANISM: Artificial
<220> FEATURE:
<223> OTHER INFORMATION: Chemically synthesized riboswitch

<400> SEQUENCE: 21 acuuuuuuc uuuuuuuuc ag                                              22

<210> SEQ ID NO 22
<211> LENGTH: 42
<212> TYPE: RNA
<213> ORGANISM: Artificial
<220> FEATURE:
<223> OTHER INFORMATION: Chemically synthesized riboswitch

<400> SEQUENCE: 22 acuuuuuuc cucauaccag ccgaaaggcc cuuggcagga gg                       42
```

```
<210> SEQ ID NO 23
<211> LENGTH: 44
<212> TYPE: RNA
<213> ORGANISM: Artificial
<220> FEATURE:
<223> OTHER INFORMATION: Chemically synthesized riboswitch

<400> SEQUENCE: 23
acuuuuuuuu uccucauacc agccgaaagg cccuuggcag gagg                44

<210> SEQ ID NO 24
<211> LENGTH: 46
<212> TYPE: RNA
<213> ORGANISM: Artificial
<220> FEATURE:
<223> OTHER INFORMATION: Chemically synthesized riboswitch

<400> SEQUENCE: 24
acuuuuuuuu uuuccucaua ccagccgaaa ggcccuuggc aggagg              46

<210> SEQ ID NO 25
<211> LENGTH: 52
<212> TYPE: RNA
<213> ORGANISM: Artificial
<220> FEATURE:
<223> OTHER INFORMATION: Chemically synthesized riboswitch

<400> SEQUENCE: 25
ggugauacca gucagcgucu ugcugacccu uggcagcacc uuuuuuuuuc ag       52

<210> SEQ ID NO 26
<211> LENGTH: 55
<212> TYPE: RNA
<213> ORGANISM: Artificial
<220> FEATURE:
<223> OTHER INFORMATION: Chemically synthesized riboswitch

<400> SEQUENCE: 26
ggugauacca gucagcgucu ugcugacccu uggcagcacc uuuuuuuuuu uucag    55

<210> SEQ ID NO 27
<211> LENGTH: 58
<212> TYPE: RNA
<213> ORGANISM: Artificial
<220> FEATURE:
<223> OTHER INFORMATION: Chemically synthesized riboswitch

<400> SEQUENCE: 27
ggugauacca gucagcgucu ugcugacccu uggcagcacc uuuuuuuuuu uuuucag  58

<210> SEQ ID NO 28
<211> LENGTH: 40
<212> TYPE: RNA
<213> ORGANISM: Artificial
<220> FEATURE:
<223> OTHER INFORMATION: Chemically synthesized riboswitch

<400> SEQUENCE: 28
gguggauggu gucagcgucu ugcugacccu uggcagcacc                    40

<210> SEQ ID NO 29
<211> LENGTH: 50
<212> TYPE: RNA
<213> ORGANISM: Artificial
<220> FEATURE:
<223> OTHER INFORMATION: Chemically synthesized riboswitch
```

```
<220> FEATURE:
<221> NAME/KEY: misc_feature
<222> LOCATION: (47)..(47)
<223> OTHER INFORMATION: 9-15 uracils

<400> SEQUENCE: 29
gucagcagau accagcaucg ucuugaugcc cuuggcagcu gcugacucag                50

<210> SEQ ID NO 30
<211> LENGTH: 18
<212> TYPE: DNA
<213> ORGANISM: Artificial
<220> FEATURE:
<223> OTHER INFORMATION: Chemically synthesized PCR primer

<400> SEQUENCE: 30
taatacgact cactatag                                                   18

<210> SEQ ID NO 31
<211> LENGTH: 54
<212> TYPE: DNA
<213> ORGANISM: Artificial
<220> FEATURE:
<223> OTHER INFORMATION: Chemically synthesized PCR primer

<400> SEQUENCE: 31
tcaacgtcga gacgctgcca agggcctttc ggctggtatc gccagagaga gagg           54

<210> SEQ ID NO 32
<211> LENGTH: 62
<212> TYPE: DNA
<213> ORGANISM: Artificial
<220> FEATURE:
<223> OTHER INFORMATION: Chemically synthesized PCR primer

<400> SEQUENCE: 32
ttgacgtcga cctcctgcca agggcctttc ggctggtatg aggaaaaaaa agaaaaaaa      60 gt                                                                    62

<210> SEQ ID NO 33
<211> LENGTH: 57
<212> TYPE: DNA
<213> ORGANISM: Artificial
<220> FEATURE:
<223> OTHER INFORMATION: Chemically synthesized PCR primer

<400> SEQUENCE: 33
ttgacgtcga cctgccaagg gcctttcggc tggtatggaa aaaaaagaa aaaaagt         57

<210> SEQ ID NO 34
<211> LENGTH: 61
<212> TYPE: DNA
<213> ORGANISM: Artificial
<220> FEATURE:
<223> OTHER INFORMATION: Chemically synthesized PCR primer

<400> SEQUENCE: 34
ttgacgtcga tcagctgcca agggcctttc ggctggtatc tgaaaaaaaa agaaaaaaag     60
t                                                                     61

<210> SEQ ID NO 35
<211> LENGTH: 34
<212> TYPE: DNA
<213> ORGANISM: Artificial
<220> FEATURE:
```

-continued

```
<223> OTHER INFORMATION: Chemically synthesized PCR primer

<400> SEQUENCE: 35
cccttggcag cgtctgagga caaactcttc gcgg                                34

<210> SEQ ID NO 36
<211> LENGTH: 40
<212> TYPE: DNA
<213> ORGANISM: Artificial
<220> FEATURE:
<223> OTHER INFORMATION: Chemically synthesized PCR primer

<400> SEQUENCE: 36
cctttcggct ggtatcgcca cgtcgacctg aaaaaaaaag                          40

<210> SEQ ID NO 37
<211> LENGTH: 19
<212> TYPE: DNA
<213> ORGANISM: Artificial
<220> FEATURE:
<223> OTHER INFORMATION: Chemically synthesized PCR primer

<400> SEQUENCE: 37
ggttaccagc cttcactgc                                                 19

<210> SEQ ID NO 38
<211> LENGTH: 19
<212> TYPE: DNA
<213> ORGANISM: Artificial
<220> FEATURE:
<223> OTHER INFORMATION: Chemically synthesized PCR primer

<400> SEQUENCE: 38
gtgtgaccga ccgtggtgc                                                 19

<210> SEQ ID NO 39
<211> LENGTH: 19
<212> TYPE: DNA
<213> ORGANISM: Artificial
<220> FEATURE:
<223> OTHER INFORMATION: Chemically synthesized PCR primer

<400> SEQUENCE: 39
tctaatacga ctcactata                                                 19

<210> SEQ ID NO 40
<211> LENGTH: 43
<212> TYPE: RNA
<213> ORGANISM: Artificial
<220> FEATURE:
<223> OTHER INFORMATION: Chemically synthesized riboswitch

<400> SEQUENCE: 40
acyyyyyyyy yyyyyyyyau accagccgaa aggcccuugg cag                      43

<210> SEQ ID NO 41
<211> LENGTH: 44
<212> TYPE: RNA
<213> ORGANISM: Artificial
<220> FEATURE:
<223> OTHER INFORMATION: Chemically synthesized riboswitch

<400> SEQUENCE: 41
acyyyyyyyy yyyyyyyya uaccagccga aaggcccuug gcag                      44
```

<210> SEQ ID NO 42
<211> LENGTH: 45
<212> TYPE: RNA
<213> ORGANISM: Artificial
<220> FEATURE:
<223> OTHER INFORMATION: Chemically synthesized riboswitch

<400> SEQUENCE: 42 acyyyyyyy yyyyyyyyy auaccagccg aaaggcccuu ggcag                    45

<210> SEQ ID NO 43
<211> LENGTH: 46
<212> TYPE: RNA
<213> ORGANISM: Artificial
<220> FEATURE:
<223> OTHER INFORMATION: Chemically synthesized riboswitch

<400> SEQUENCE: 43 acyyyyyyy yyyyyyyyy yauaccagcc gaaaggcccu uggcag                   46

<210> SEQ ID NO 44
<211> LENGTH: 47
<212> TYPE: RNA
<213> ORGANISM: Artificial
<220> FEATURE:
<223> OTHER INFORMATION: Chemically synthesized riboswitch

<400> SEQUENCE: 44 acyyyyyyy yyyyyyyyy yyauaccagc cgaaaggccc uuggcag                  47

<210> SEQ ID NO 45
<211> LENGTH: 48
<212> TYPE: RNA
<213> ORGANISM: Artificial
<220> FEATURE:
<223> OTHER INFORMATION: Chemically synthesized riboswitch

<400> SEQUENCE: 45 acyyyyyyy yyyyyyyyy yyyauaccag ccgaaaggcc cuuggcag                 48

<210> SEQ ID NO 46
<211> LENGTH: 49
<212> TYPE: RNA
<213> ORGANISM: Artificial
<220> FEATURE:
<223> OTHER INFORMATION: Chemically synthesized riboswitch

<400> SEQUENCE: 46 acyyyyyyy yyyyyyyyy yyyyauacca gccgaaaggc ccuuggcag                49

<210> SEQ ID NO 47
<211> LENGTH: 50
<212> TYPE: RNA
<213> ORGANISM: Artificial
<220> FEATURE:
<223> OTHER INFORMATION: Chemically synthesized riboswitch

<400> SEQUENCE: 47 acyyyyyyy yyyyyyyyy yyyyyauacc agccgaaagg cccuuggcag               50

<210> SEQ ID NO 48
<211> LENGTH: 51
<212> TYPE: RNA
<213> ORGANISM: Artificial
<220> FEATURE:
<223> OTHER INFORMATION: Chemically synthesized riboswitch

```
<400> SEQUENCE: 48
acyyyyyyyy yyyyyyyyyy yyyyyyauac cagccgaaag gcccuuggca g         51

<210> SEQ ID NO 49
<211> LENGTH: 52
<212> TYPE: RNA
<213> ORGANISM: Artificial
<220> FEATURE:
<223> OTHER INFORMATION: Chemically synthesized riboswitch

<400> SEQUENCE: 49
acyyyyyyyy yyyyyyyyyy yyyyyyyaua ccagccgaaa ggcccuuggc ag        52

<210> SEQ ID NO 50
<211> LENGTH: 53
<212> TYPE: RNA
<213> ORGANISM: Artificial
<220> FEATURE:
<223> OTHER INFORMATION: Chemically synthesized riboswitch

<400> SEQUENCE: 50
acyyyyyyyy yyyyyyyyyy yyyyyyyyau accagccgaa aggcccuugg cag       53

<210> SEQ ID NO 51
<211> LENGTH: 54
<212> TYPE: RNA
<213> ORGANISM: Artificial
<220> FEATURE:
<223> OTHER INFORMATION: Chemically synthesized riboswitch

<400> SEQUENCE: 51
acyyyyyyyy yyyyyyyyyy yyyyyyyyya uaccagccga aaggcccuug gcag      54

<210> SEQ ID NO 52
<211> LENGTH: 55
<212> TYPE: RNA
<213> ORGANISM: Artificial
<220> FEATURE:
<223> OTHER INFORMATION: Chemically synthesized riboswitch

<400> SEQUENCE: 52
acyyyyyyyy yyyyyyyyyy yyyyyyyyyy auaccagccg aaaggcccuu ggcag     55

<210> SEQ ID NO 53
<211> LENGTH: 56
<212> TYPE: RNA
<213> ORGANISM: Artificial
<220> FEATURE:
<223> OTHER INFORMATION: Chemically synthesized riboswitch

<400> SEQUENCE: 53
acyyyyyyyy yyyyyyyyyy yyyyyyyyyy yauaccagcc gaaaggcccu uggcag    56

<210> SEQ ID NO 54
<211> LENGTH: 57
<212> TYPE: RNA
<213> ORGANISM: Artificial
<220> FEATURE:
<223> OTHER INFORMATION: Chemically synthesized riboswitch

<400> SEQUENCE: 54
acyyyyyyyy yyyyyyyyyy yyyyyyyyyy yyauaccagc cgaaaggccc uuggcag   57

<210> SEQ ID NO 55
<211> LENGTH: 58
```

```
<212> TYPE: RNA
<213> ORGANISM: Artificial
<220> FEATURE:
<223> OTHER INFORMATION: Chemically synthesized riboswitch

<400> SEQUENCE: 55 acyyyyyyy yyyyyyyyy yyyyyyyyy yyyauaccag ccgaaaggcc cuuggcag         58

<210> SEQ ID NO 56
<211> LENGTH: 47
<212> TYPE: RNA
<213> ORGANISM: Artificial
<220> FEATURE:
<223> OTHER INFORMATION: Chemically synthesized riboswitch
<220> FEATURE:
<221> NAME/KEY: misc_feature
<222> LOCATION: (15)..(15)
<223> OTHER INFORMATION: complementary to nucleotide 47
<220> FEATURE:
<221> NAME/KEY: misc_feature
<222> LOCATION: (16)..(16)
<223> OTHER INFORMATION: complementary to nucleotide 46
<220> FEATURE:
<221> NAME/KEY: misc_feature
<222> LOCATION: (17)..(17)
<223> OTHER INFORMATION: complementary to nucleotide 45
<220> FEATURE:
<221> NAME/KEY: misc_feature
<222> LOCATION: (18)..(18)
<223> OTHER INFORMATION: complementary to nucleotide 44
<220> FEATURE:
<221> NAME/KEY: misc_feature
<222> LOCATION: (44)..(47)
<223> OTHER INFORMATION: n is a, c, g, or u

<400> SEQUENCE: 56 acyyyyyyy yyyynnnnau accagccgaa aggcccuugg cagnnnn                   47

<210> SEQ ID NO 57
<211> LENGTH: 48
<212> TYPE: RNA
<213> ORGANISM: Artificial
<220> FEATURE:
<223> OTHER INFORMATION: Chemically synthesized riboswitch
<220> FEATURE:
<221> NAME/KEY: misc_feature
<222> LOCATION: (16)..(16)
<223> OTHER INFORMATION: complementary to nucleotide 48
<220> FEATURE:
<221> NAME/KEY: misc_feature
<222> LOCATION: (17)..(17)
<223> OTHER INFORMATION: complementary to nucleotide 47
<220> FEATURE:
<221> NAME/KEY: misc_feature
<222> LOCATION: (18)..(18)
<223> OTHER INFORMATION: complementary to nucleotide 46
<220> FEATURE:
<221> NAME/KEY: misc_feature
<222> LOCATION: (19)..(19)
<223> OTHER INFORMATION: complementary to nucleotide 45
<220> FEATURE:
<221> NAME/KEY: misc_feature
<222> LOCATION: (45)..(48)
<223> OTHER INFORMATION: n is a, c, g, or u

<400> SEQUENCE: 57 acyyyyyyy yyyyynnnna uaccagccga aggcccuug gcagnnnn                   48

<210> SEQ ID NO 58
<211> LENGTH: 49
<212> TYPE: RNA
<213> ORGANISM: Artificial
<220> FEATURE:
```

<223> OTHER INFORMATION: Chemically synthesized riboswitch
<220> FEATURE:
<221> NAME/KEY: misc_feature
<222> LOCATION: (17)..(17)
<223> OTHER INFORMATION: complementary to nucleotide 49
<220> FEATURE:
<221> NAME/KEY: misc_feature
<222> LOCATION: (18)..(18)
<223> OTHER INFORMATION: complementary to nucleotide 48
<220> FEATURE:
<221> NAME/KEY: misc_feature
<222> LOCATION: (19)..(19)
<223> OTHER INFORMATION: complementary to nucleotide 47
<220> FEATURE:
<221> NAME/KEY: misc_feature
<222> LOCATION: (20)..(20)
<223> OTHER INFORMATION: complementary to nucleotide 46
<220> FEATURE:
<221> NAME/KEY: misc_feature
<222> LOCATION: (46)..(49)
<223> OTHER INFORMATION: n is a, c, g, or u

<400> SEQUENCE: 58
acyyyyyyyy yyyyyynnnn auaccagccg aaaggcccuu ggcagnnnn         49

<210> SEQ ID NO 59
<211> LENGTH: 50
<212> TYPE: RNA
<213> ORGANISM: Artificial
<220> FEATURE:
<223> OTHER INFORMATION: Chemically synthesized riboswitch
<220> FEATURE:
<221> NAME/KEY: misc_feature
<222> LOCATION: (18)..(18)
<223> OTHER INFORMATION: complementary to nucleotide 50
<220> FEATURE:
<221> NAME/KEY: misc_feature
<222> LOCATION: (19)..(19)
<223> OTHER INFORMATION: complementary to nucleotide 49
<220> FEATURE:
<221> NAME/KEY: misc_feature
<222> LOCATION: (20)..(20)
<223> OTHER INFORMATION: complementary to nucleotide 48
<220> FEATURE:
<221> NAME/KEY: misc_feature
<222> LOCATION: (21)..(21)
<223> OTHER INFORMATION: complementary to nucleotide 47
<220> FEATURE:
<221> NAME/KEY: misc_feature
<222> LOCATION: (47)..(50)
<223> OTHER INFORMATION: n is a, c, g, or u

<400> SEQUENCE: 59
acyyyyyyyy yyyyyyynnn nauaccagcc gaaaggcccu uggcagnnnn         50

<210> SEQ ID NO 60
<211> LENGTH: 51
<212> TYPE: RNA
<213> ORGANISM: Artificial
<220> FEATURE:
<223> OTHER INFORMATION: Chemically synthesized riboswitch
<220> FEATURE:
<221> NAME/KEY: misc_feature
<222> LOCATION: (19)..(19)
<223> OTHER INFORMATION: complementary to nucleotide 51
<220> FEATURE:
<221> NAME/KEY: misc_feature
<222> LOCATION: (20)..(20)
<223> OTHER INFORMATION: complementary to nucleotide 50
<220> FEATURE:
<221> NAME/KEY: misc_feature
<222> LOCATION: (21)..(21)
<223> OTHER INFORMATION: complementary to nucleotide 49
<220> FEATURE:
<221> NAME/KEY: misc_feature
<222> LOCATION: (22)..(22)
<223> OTHER INFORMATION: complementary to nucleotide 48
<220> FEATURE:
<221> NAME/KEY: misc_feature
<222> LOCATION: (48)..(51)
<223> OTHER INFORMATION: n is a, c, g, or u

<400> SEQUENCE: 60
acyyyyyyyy yyyyyyyynn nnauaccagc cgaaaggccc uuggcagnnn n    51

<210> SEQ ID NO 61
<211> LENGTH: 52
<212> TYPE: RNA
<213> ORGANISM: Artificial
<220> FEATURE:
<223> OTHER INFORMATION: Chemically synthesized riboswitch
<220> FEATURE:
<221> NAME/KEY: misc_feature
<222> LOCATION: (20)..(20)
<223> OTHER INFORMATION: complementary to nucleotide 52
<220> FEATURE:
<221> NAME/KEY: misc_feature
<222> LOCATION: (21)..(21)
<223> OTHER INFORMATION: complementary to nucleotide 51
<220> FEATURE:
<221> NAME/KEY: misc_feature
<222> LOCATION: (22)..(22)
<223> OTHER INFORMATION: complementary to nucleotide 50
<220> FEATURE:
<221> NAME/KEY: misc_feature
<222> LOCATION: (23)..(23)
<223> OTHER INFORMATION: complementary to nucleotide 49
<220> FEATURE:
<221> NAME/KEY: misc_feature
<222> LOCATION: (49)..(52)
<223> OTHER INFORMATION: n is a, c, g, or u

<400> SEQUENCE: 61
acyyyyyyyy yyyyyyyyyn nnnauaccag ccgaaaggcc cuuggcagnn nn    52

<210> SEQ ID NO 62
<211> LENGTH: 53
<212> TYPE: RNA
<213> ORGANISM: Artificial
<220> FEATURE:
<223> OTHER INFORMATION: Chemically synthesized riboswitch
<220> FEATURE:
<221> NAME/KEY: misc_feature
<222> LOCATION: (21)..(21)
<223> OTHER INFORMATION: complementary to nucleotide 53
<220> FEATURE:
<221> NAME/KEY: misc_feature
<222> LOCATION: (22)..(22)
<223> OTHER INFORMATION: complementary to nucleotide 52
<220> FEATURE:
<221> NAME/KEY: misc_feature
<222> LOCATION: (23)..(23)
<223> OTHER INFORMATION: complementary to nucleotide 51
<220> FEATURE:
<221> NAME/KEY: misc_feature
<222> LOCATION: (24)..(24)
<223> OTHER INFORMATION: complementary to nucleotide 50
<220> FEATURE:
<221> NAME/KEY: misc_feature
<222> LOCATION: (50)..(53)
<223> OTHER INFORMATION: n is a, c, g, or u

<400> SEQUENCE: 62
acyyyyyyyy yyyyyyyyy nnnnauacca gccgaaaggc ccuuggcagn nnn    53

<210> SEQ ID NO 63
<211> LENGTH: 54
<212> TYPE: RNA

```
<213> ORGANISM: Artificial
<220> FEATURE:
<223> OTHER INFORMATION: Chemically synthesized riboswitch
<220> FEATURE:
<221> NAME/KEY: misc_feature
<222> LOCATION: (22)..(22)
<223> OTHER INFORMATION: complementary to nucleotide 54
<220> FEATURE:
<221> NAME/KEY: misc_feature
<222> LOCATION: (23)..(23)
<223> OTHER INFORMATION: complementary to nucleotide 53
<220> FEATURE:
<221> NAME/KEY: misc_feature
<222> LOCATION: (24)..(24)
<223> OTHER INFORMATION: complementary to nucleotide 52
<220> FEATURE:
<221> NAME/KEY: misc_feature
<222> LOCATION: (25)..(25)
<223> OTHER INFORMATION: complementary to nucleotide 51
<220> FEATURE:
<221> NAME/KEY: misc_feature
<222> LOCATION: (51)..(54)
<223> OTHER INFORMATION: n is a, c, g, or u

<400> SEQUENCE: 63 acyyyyyyy yyyyyyyyy ynnnnauacc agccgaaagg cccuuggcag nnnn       54

<210> SEQ ID NO 64
<211> LENGTH: 55
<212> TYPE: RNA
<213> ORGANISM: Artificial
<220> FEATURE:
<223> OTHER INFORMATION: Chemically synthesized riboswitch
<220> FEATURE:
<221> NAME/KEY: misc_feature
<222> LOCATION: (23)..(23)
<223> OTHER INFORMATION: complementary to nucleotide 55
<220> FEATURE:
<221> NAME/KEY: misc_feature
<222> LOCATION: (24)..(24)
<223> OTHER INFORMATION: complementary to nucleotide 54
<220> FEATURE:
<221> NAME/KEY: misc_feature
<222> LOCATION: (25)..(25)
<223> OTHER INFORMATION: complementary to nucleotide 53
<220> FEATURE:
<221> NAME/KEY: misc_feature
<222> LOCATION: (26)..(26)
<223> OTHER INFORMATION: complementary to nucleotide 52
<220> FEATURE:
<221> NAME/KEY: misc_feature
<222> LOCATION: (52)..(55)
<223> OTHER INFORMATION: n is a, c, g, or u

<400> SEQUENCE: 64 acyyyyyyy yyyyyyyyy yynnnnauac cagccgaaag gcccuuggca gnnnn       55

<210> SEQ ID NO 65
<211> LENGTH: 56
<212> TYPE: RNA
<213> ORGANISM: Artificial
<220> FEATURE:
<223> OTHER INFORMATION: Chemically synthesized riboswitch
<220> FEATURE:
<221> NAME/KEY: misc_feature
<222> LOCATION: (24)..(24)
<223> OTHER INFORMATION: complementary to nucleotide 56
<220> FEATURE:
<221> NAME/KEY: misc_feature
<222> LOCATION: (25)..(25)
<223> OTHER INFORMATION: complementary to nucleotide 55
<220> FEATURE:
<221> NAME/KEY: misc_feature
<222> LOCATION: (26)..(26)
<223> OTHER INFORMATION: complementary to nucleotide 54
```

```
<220> FEATURE:
<221> NAME/KEY: misc_feature
<222> LOCATION: (27)..(27)
<223> OTHER INFORMATION: complementary to nucleotide 53
<220> FEATURE:
<221> NAME/KEY: misc_feature
<222> LOCATION: (53)..(56)
<223> OTHER INFORMATION: n is a, c, g, or u

<400> SEQUENCE: 65
acyyyyyyyy yyyyyyyyy yyynnnaua ccagccgaaa ggcccuuggc agnnnn        56

<210> SEQ ID NO 66
<211> LENGTH: 57
<212> TYPE: RNA
<213> ORGANISM: Artificial
<220> FEATURE:
<223> OTHER INFORMATION: Chemically synthesized riboswitch
<220> FEATURE:
<221> NAME/KEY: misc_feature
<222> LOCATION: (25)..(25)
<223> OTHER INFORMATION: complementary to nucleotide 57
<220> FEATURE:
<221> NAME/KEY: misc_feature
<222> LOCATION: (26)..(26)
<223> OTHER INFORMATION: complementary to nucleotide 56
<220> FEATURE:
<221> NAME/KEY: misc_feature
<222> LOCATION: (27)..(27)
<223> OTHER INFORMATION: complementary to nucleotide 55
<220> FEATURE:
<221> NAME/KEY: misc_feature
<222> LOCATION: (28)..(28)
<223> OTHER INFORMATION: complementary to nucleotide 54
<220> FEATURE:
<221> NAME/KEY: misc_feature
<222> LOCATION: (54)..(57)
<223> OTHER INFORMATION: n is a, c, g, or u

<400> SEQUENCE: 66
acyyyyyyyy yyyyyyyyy yyyynnnau accagccgaa aggcccuugg cagnnnn      57

<210> SEQ ID NO 67
<211> LENGTH: 58
<212> TYPE: RNA
<213> ORGANISM: Artificial
<220> FEATURE:
<223> OTHER INFORMATION: Chemically synthesized riboswitch
<220> FEATURE:
<221> NAME/KEY: misc_feature
<222> LOCATION: (26)..(26)
<223> OTHER INFORMATION: complementary to nucleotide 58
<220> FEATURE:
<221> NAME/KEY: misc_feature
<222> LOCATION: (27)..(27)
<223> OTHER INFORMATION: complementary to nucleotide 57
<220> FEATURE:
<221> NAME/KEY: misc_feature
<222> LOCATION: (28)..(28)
<223> OTHER INFORMATION: complementary to nucleotide 56
<220> FEATURE:
<221> NAME/KEY: misc_feature
<222> LOCATION: (29)..(29)
<223> OTHER INFORMATION: complementary to nucleotide 55
<220> FEATURE:
<221> NAME/KEY: misc_feature
<222> LOCATION: (55)..(58)
<223> OTHER INFORMATION: n is a, c, g, or u

<400> SEQUENCE: 67
acyyyyyyyy yyyyyyyyy yyyyynnna uaccagccga aaggcccuug gcagnnnn     58

<210> SEQ ID NO 68
```

<211> LENGTH: 59
<212> TYPE: RNA
<213> ORGANISM: Artificial
<220> FEATURE:
<223> OTHER INFORMATION: Chemically synthesized riboswitch
<220> FEATURE:
<221> NAME/KEY: misc_feature
<222> LOCATION: (27)..(27)
<223> OTHER INFORMATION: complementary to nucleotide 59
<220> FEATURE:
<221> NAME/KEY: misc_feature
<222> LOCATION: (28)..(28)
<223> OTHER INFORMATION: complementary to nucleotide 58
<220> FEATURE:
<221> NAME/KEY: misc_feature
<222> LOCATION: (29)..(29)
<223> OTHER INFORMATION: complementary to nucleotide 57
<220> FEATURE:
<221> NAME/KEY: misc_feature
<222> LOCATION: (30)..(30)
<223> OTHER INFORMATION: complementary to nucleotide 56
<220> FEATURE:
<221> NAME/KEY: misc_feature
<222> LOCATION: (56)..(59)
<223> OTHER INFORMATION: n is a, c, g, or u

<400> SEQUENCE: 68 acyyyyyyy yyyyyyyyy yyyyyynnnn auaccagccg aaaggcccuu ggcagnnnn        59

<210> SEQ ID NO 69
<211> LENGTH: 60
<212> TYPE: RNA
<213> ORGANISM: Artificial
<220> FEATURE:
<223> OTHER INFORMATION: Chemically synthesized riboswitch
<220> FEATURE:
<221> NAME/KEY: misc_feature
<222> LOCATION: (28)..(28)
<223> OTHER INFORMATION: complementary to nucleotide 60
<220> FEATURE:
<221> NAME/KEY: misc_feature
<222> LOCATION: (29)..(29)
<223> OTHER INFORMATION: complementary to nucleotide 59
<220> FEATURE:
<221> NAME/KEY: misc_feature
<222> LOCATION: (30)..(30)
<223> OTHER INFORMATION: complementary to nucleotide 58
<220> FEATURE:
<221> NAME/KEY: misc_feature
<222> LOCATION: (31)..(31)
<223> OTHER INFORMATION: complementary to nucleotide 57
<220> FEATURE:
<221> NAME/KEY: misc_feature
<222> LOCATION: (57)..(60)
<223> OTHER INFORMATION: n is a, c, g, or u

<400> SEQUENCE: 69 acyyyyyyy yyyyyyyyy yyyyyyynnn nauaccagcc gaaaggcccu uggcagnnnn        60

<210> SEQ ID NO 70
<211> LENGTH: 61
<212> TYPE: RNA
<213> ORGANISM: Artificial
<220> FEATURE:
<223> OTHER INFORMATION: Chemically synthesized riboswitch
<220> FEATURE:
<221> NAME/KEY: misc_feature
<222> LOCATION: (29)..(29)
<223> OTHER INFORMATION: complementary to nucleotide 61
<220> FEATURE:
<221> NAME/KEY: misc_feature
<222> LOCATION: (30)..(30)
<223> OTHER INFORMATION: complementary to nucleotide 60
<220> FEATURE:
<221> NAME/KEY: misc_feature

```
<222> LOCATION: (31)..(31)
<223> OTHER INFORMATION: complementary to nucleotide 59
<220> FEATURE:
<221> NAME/KEY: misc_feature
<222> LOCATION: (32)..(32)
<223> OTHER INFORMATION: complementary to nucleotide 58
<220> FEATURE:
<221> NAME/KEY: misc_feature
<222> LOCATION: (58)..(61)
<223> OTHER INFORMATION: n is a, c, g, or u

<400> SEQUENCE: 70
acyyyyyyyy yyyyyyyyyy yyyyyyyynn nnauaccagc cgaaaggccc uuggcagnnn    60 n                                                                    61

<210> SEQ ID NO 71
<211> LENGTH: 62
<212> TYPE: RNA
<213> ORGANISM: Artificial
<220> FEATURE:
<223> OTHER INFORMATION: Chemically synthesized riboswitch
<220> FEATURE:
<221> NAME/KEY: misc_feature
<222> LOCATION: (30)..(30)
<223> OTHER INFORMATION: complementary to nucleotide 62
<220> FEATURE:
<221> NAME/KEY: misc_feature
<222> LOCATION: (31)..(31)
<223> OTHER INFORMATION: complementary to nucleotide 61
<220> FEATURE:
<221> NAME/KEY: misc_feature
<222> LOCATION: (32)..(32)
<223> OTHER INFORMATION: complementary to nucleotide 60
<220> FEATURE:
<221> NAME/KEY: misc_feature
<222> LOCATION: (33)..(33)
<223> OTHER INFORMATION: complementary to nucleotide 59
<220> FEATURE:
<221> NAME/KEY: misc_feature
<222> LOCATION: (59)..(62)
<223> OTHER INFORMATION: n is a, c, g, or u

<400> SEQUENCE: 71
acyyyyyyyy yyyyyyyyyy yyyyyyyyyn nnnauaccag ccgaaaggcc cuuggcagnn    60 nn                                                                   62

<210> SEQ ID NO 72
<211> LENGTH: 47
<212> TYPE: RNA
<213> ORGANISM: Artificial
<220> FEATURE:
<223> OTHER INFORMATION: Chemically synthesized riboswitch
<220> FEATURE:
<221> NAME/KEY: misc_feature
<222> LOCATION: (15)..(15)
<223> OTHER INFORMATION: complementary to nucleotide 47
<220> FEATURE:
<221> NAME/KEY: misc_feature
<222> LOCATION: (16)..(16)
<223> OTHER INFORMATION: complementary to nucleotide 46
<220> FEATURE:
<221> NAME/KEY: misc_feature
<222> LOCATION: (17)..(17)
<223> OTHER INFORMATION: complementary to nucleotide 45
<220> FEATURE:
<221> NAME/KEY: misc_feature
<222> LOCATION: (18)..(18)
<223> OTHER INFORMATION: complementary to nucleotide 44
<220> FEATURE:
<221> NAME/KEY: misc_feature
<222> LOCATION: (44)..(47)
<223> OTHER INFORMATION: n is a, c, g, or u
```

```
<400> SEQUENCE: 72
acuuuuuuuu uuuunnnnau accagccgaa aggcccuugg cagnnnn                        47

<210> SEQ ID NO 73
<211> LENGTH: 48
<212> TYPE: RNA
<213> ORGANISM: Artificial
<220> FEATURE:
<223> OTHER INFORMATION: Chemically synthesized riboswitch
<220> FEATURE:
<221> NAME/KEY: misc_feature
<222> LOCATION: (16)..(16)
<223> OTHER INFORMATION: complementary to nucleotide 48
<220> FEATURE:
<221> NAME/KEY: misc_feature
<222> LOCATION: (17)..(17)
<223> OTHER INFORMATION: complementary to nucleotide 47
<220> FEATURE:
<221> NAME/KEY: misc_feature
<222> LOCATION: (18)..(18)
<223> OTHER INFORMATION: complementary to nucleotide 46
<220> FEATURE:
<221> NAME/KEY: misc_feature
<222> LOCATION: (19)..(19)
<223> OTHER INFORMATION: complementary to nucleotide 45
<220> FEATURE:
<221> NAME/KEY: misc_feature
<222> LOCATION: (45)..(48)
<223> OTHER INFORMATION: n is a, c, g, or u

<400> SEQUENCE: 73
acuuuuuuuu uuuuunnnna uaccagccga aaggcccuug gcagnnnn                       48

<210> SEQ ID NO 74
<211> LENGTH: 49
<212> TYPE: RNA
<213> ORGANISM: Artificial
<220> FEATURE:
<223> OTHER INFORMATION: Chemically synthesized riboswitch
<220> FEATURE:
<221> NAME/KEY: misc_feature
<222> LOCATION: (17)..(17)
<223> OTHER INFORMATION: complementary to nucleotide 49
<220> FEATURE:
<221> NAME/KEY: misc_feature
<222> LOCATION: (18)..(18)
<223> OTHER INFORMATION: complementary to nucleotide 48
<220> FEATURE:
<221> NAME/KEY: misc_feature
<222> LOCATION: (19)..(19)
<223> OTHER INFORMATION: complementary to nucleotide 47
<220> FEATURE:
<221> NAME/KEY: misc_feature
<222> LOCATION: (20)..(20)
<223> OTHER INFORMATION: complementary to nucleotide 46
<220> FEATURE:
<221> NAME/KEY: misc_feature
<222> LOCATION: (46)..(49)
<223> OTHER INFORMATION: n is a, c, g, or u

<400> SEQUENCE: 74
acuuuuuuuu uuuuuunnnn auaccagccg aaaggcccuu ggcagnnnn                      49

<210> SEQ ID NO 75
<211> LENGTH: 50
<212> TYPE: RNA
<213> ORGANISM: Artificial
<220> FEATURE:
<223> OTHER INFORMATION: Chemically synthesized riboswitch
<220> FEATURE:
<221> NAME/KEY: misc_feature
<222> LOCATION: (18)..(18)
<223> OTHER INFORMATION: complementary to nucleotide 50
```

```
<220> FEATURE:
<221> NAME/KEY: misc_feature
<222> LOCATION: (19)..(19)
<223> OTHER INFORMATION: complementary to nucleotide 49
<220> FEATURE:
<221> NAME/KEY: misc_feature
<222> LOCATION: (20)..(20)
<223> OTHER INFORMATION: complementary to nucleotide 48
<220> FEATURE:
<221> NAME/KEY: misc_feature
<222> LOCATION: (21)..(21)
<223> OTHER INFORMATION: complementary to nucleotide 47
<220> FEATURE:
<221> NAME/KEY: misc_feature
<222> LOCATION: (47)..(50)
<223> OTHER INFORMATION: n is a, c, g, or u

<400> SEQUENCE: 75
acuuuuuuuu uuuuuuunnn nauaccagcc gaaaggcccu uggcagnnnn          50

<210> SEQ ID NO 76
<211> LENGTH: 51
<212> TYPE: RNA
<213> ORGANISM: Artificial
<220> FEATURE:
<223> OTHER INFORMATION: Chemically synthesized riboswitch
<220> FEATURE:
<221> NAME/KEY: misc_feature
<222> LOCATION: (19)..(19)
<223> OTHER INFORMATION: complementary to nucleotide 51
<220> FEATURE:
<221> NAME/KEY: misc_feature
<222> LOCATION: (20)..(20)
<223> OTHER INFORMATION: complementary to nucleotide 50
<220> FEATURE:
<221> NAME/KEY: misc_feature
<222> LOCATION: (21)..(21)
<223> OTHER INFORMATION: complementary to nucleotide 49
<220> FEATURE:
<221> NAME/KEY: misc_feature
<222> LOCATION: (22)..(22)
<223> OTHER INFORMATION: complementary to nucleotide 48
<220> FEATURE:
<221> NAME/KEY: misc_feature
<222> LOCATION: (48)..(51)
<223> OTHER INFORMATION: n is a, c, g, or u

<400> SEQUENCE: 76
acuuuuuuuu uuuuuuunn nnauaccagc cgaaaggccc uuggcagnnn n          51

<210> SEQ ID NO 77
<211> LENGTH: 52
<212> TYPE: RNA
<213> ORGANISM: Artificial
<220> FEATURE:
<223> OTHER INFORMATION: Chemically synthesized riboswitch
<220> FEATURE:
<221> NAME/KEY: misc_feature
<222> LOCATION: (20)..(20)
<223> OTHER INFORMATION: complementary to nucleotide 52
<220> FEATURE:
<221> NAME/KEY: misc_feature
<222> LOCATION: (21)..(21)
<223> OTHER INFORMATION: complementary to nucleotide 51
<220> FEATURE:
<221> NAME/KEY: misc_feature
<222> LOCATION: (22)..(22)
<223> OTHER INFORMATION: complementary to nucleotide 50
<220> FEATURE:
<221> NAME/KEY: misc_feature
<222> LOCATION: (23)..(23)
<223> OTHER INFORMATION: complementary to nucleotide 49
<220> FEATURE:
<221> NAME/KEY: misc_feature
<222> LOCATION: (49)..(52)
```

```
<223> OTHER INFORMATION: n is a, c, g, or u

<400> SEQUENCE: 77
acuuuuuuuu uuuuuuuuun nnnauaccag ccgaaaggcc cuuggcagnn nn          52

<210> SEQ ID NO 78
<211> LENGTH: 53
<212> TYPE: RNA
<213> ORGANISM: Artificial
<220> FEATURE:
<223> OTHER INFORMATION: Chemically synthesized riboswitch
<220> FEATURE:
<221> NAME/KEY: misc_feature
<222> LOCATION: (21)..(21)
<223> OTHER INFORMATION: complementary to nucleotide 53
<220> FEATURE:
<221> NAME/KEY: misc_feature
<222> LOCATION: (22)..(22)
<223> OTHER INFORMATION: complementary to nucleotide 52
<220> FEATURE:
<221> NAME/KEY: misc_feature
<222> LOCATION: (23)..(23)
<223> OTHER INFORMATION: complementary to nucleotide 51
<220> FEATURE:
<221> NAME/KEY: misc_feature
<222> LOCATION: (24)..(24)
<223> OTHER INFORMATION: complementary to nucleotide 50
<220> FEATURE:
<221> NAME/KEY: misc_feature
<222> LOCATION: (50)..(53)
<223> OTHER INFORMATION: n is a, c, g, or u

<400> SEQUENCE: 78
acuuuuuuuu uuuuuuuuuu nnnnauacca gccgaaaggc ccuuggcagn nnn         53

<210> SEQ ID NO 79
<211> LENGTH: 54
<212> TYPE: RNA
<213> ORGANISM: Artificial
<220> FEATURE:
<223> OTHER INFORMATION: Chemically synthesized riboswitch
<220> FEATURE:
<221> NAME/KEY: misc_feature
<222> LOCATION: (22)..(22)
<223> OTHER INFORMATION: complementary to nucleotide 54
<220> FEATURE:
<221> NAME/KEY: misc_feature
<222> LOCATION: (23)..(23)
<223> OTHER INFORMATION: complementary to nucleotide 53
<220> FEATURE:
<221> NAME/KEY: misc_feature
<222> LOCATION: (24)..(24)
<223> OTHER INFORMATION: complementary to nucleotide 52
<220> FEATURE:
<221> NAME/KEY: misc_feature
<222> LOCATION: (25)..(25)
<223> OTHER INFORMATION: complementary to nucleotide 51
<220> FEATURE:
<221> NAME/KEY: misc_feature
<222> LOCATION: (51)..(54)
<223> OTHER INFORMATION: n is a, c, g, or u

<400> SEQUENCE: 79
acuuuuuuuu uuuuuuuuuu unnnnauacc agccgaaagg cccuuggcag nnnn        54

<210> SEQ ID NO 80
<211> LENGTH: 55
<212> TYPE: RNA
<213> ORGANISM: Artificial
<220> FEATURE:
<223> OTHER INFORMATION: Chemically synthesized riboswitch
<220> FEATURE:
<221> NAME/KEY: misc_feature
```

```
<222> LOCATION: (23)..(23)
<223> OTHER INFORMATION: complementary to nucleotide 55
<220> FEATURE:
<221> NAME/KEY: misc_feature
<222> LOCATION: (24)..(24)
<223> OTHER INFORMATION: complementary to nucleotide 54
<220> FEATURE:
<221> NAME/KEY: misc_feature
<222> LOCATION: (25)..(25)
<223> OTHER INFORMATION: complementary to nucleotide 53
<220> FEATURE:
<221> NAME/KEY: misc_feature
<222> LOCATION: (26)..(26)
<223> OTHER INFORMATION: complementary to nucleotide 52
<220> FEATURE:
<221> NAME/KEY: misc_feature
<222> LOCATION: (52)..(55)
<223> OTHER INFORMATION: n is a, c, g, or u

<400> SEQUENCE: 80
acuuuuuuuu uuuuuuuuuu uunnnnauac cagccgaaag gcccuuggca gnnnn        55

<210> SEQ ID NO 81
<211> LENGTH: 56
<212> TYPE: RNA
<213> ORGANISM: Artificial
<220> FEATURE:
<223> OTHER INFORMATION: Chemically synthesized riboswitch
<220> FEATURE:
<221> NAME/KEY: misc_feature
<222> LOCATION: (24)..(24)
<223> OTHER INFORMATION: complementary to nucleotide 56
<220> FEATURE:
<221> NAME/KEY: misc_feature
<222> LOCATION: (25)..(25)
<223> OTHER INFORMATION: complementary to nucleotide 55
<220> FEATURE:
<221> NAME/KEY: misc_feature
<222> LOCATION: (26)..(26)
<223> OTHER INFORMATION: complementary to nucleotide 54
<220> FEATURE:
<221> NAME/KEY: misc_feature
<222> LOCATION: (27)..(27)
<223> OTHER INFORMATION: complementary to nucleotide 53
<220> FEATURE:
<221> NAME/KEY: misc_feature
<222> LOCATION: (53)..(56)
<223> OTHER INFORMATION: n is a, c, g, or u

<400> SEQUENCE: 81
acuuuuuuuu uuuuuuuuuu uuunnnnaua ccagccgaaa ggcccuuggc agnnnn       56

<210> SEQ ID NO 82
<211> LENGTH: 57
<212> TYPE: RNA
<213> ORGANISM: Artificial
<220> FEATURE:
<223> OTHER INFORMATION: Chemically synthesized riboswitch
<220> FEATURE:
<221> NAME/KEY: misc_feature
<222> LOCATION: (25)..(25)
<223> OTHER INFORMATION: complementary to nucleotide 57
<220> FEATURE:
<221> NAME/KEY: misc_feature
<222> LOCATION: (26)..(26)
<223> OTHER INFORMATION: complementary to nucleotide 56
<220> FEATURE:
<221> NAME/KEY: misc_feature
<222> LOCATION: (27)..(27)
<223> OTHER INFORMATION: complementary to nucleotide 55
<220> FEATURE:
<221> NAME/KEY: misc_feature
<222> LOCATION: (28)..(28)
<223> OTHER INFORMATION: complementary to nucleotide 54
<220> FEATURE:
```

```
<221> NAME/KEY: misc_feature
<222> LOCATION: (54)..(57)
<223> OTHER INFORMATION: n is a, c, g, or u

<400> SEQUENCE: 82
acuuuuuuuu uuuuuuuuuu uuuunnnnau accagccgaa aggcccuugg cagnnnn            57

<210> SEQ ID NO 83
<211> LENGTH: 58
<212> TYPE: RNA
<213> ORGANISM: Artificial
<220> FEATURE:
<223> OTHER INFORMATION: Chemically synthesized riboswitch
<220> FEATURE:
<221> NAME/KEY: misc_feature
<222> LOCATION: (26)..(26)
<223> OTHER INFORMATION: complementary to nucleotide 58
<220> FEATURE:
<221> NAME/KEY: misc_feature
<222> LOCATION: (27)..(27)
<223> OTHER INFORMATION: complementary to nucleotide 57
<220> FEATURE:
<221> NAME/KEY: misc_feature
<222> LOCATION: (28)..(28)
<223> OTHER INFORMATION: complementary to nucleotide 56
<220> FEATURE:
<221> NAME/KEY: misc_feature
<222> LOCATION: (29)..(29)
<223> OTHER INFORMATION: complementary to nucleotide 55
<220> FEATURE:
<221> NAME/KEY: misc_feature
<222> LOCATION: (55)..(58)
<223> OTHER INFORMATION: n is a, c, g, or u

<400> SEQUENCE: 83
acuuuuuuuu uuuuuuuuuu uuuuunnnna uaccagccga aaggcccuug gcagnnnn           58

<210> SEQ ID NO 84
<211> LENGTH: 59
<212> TYPE: RNA
<213> ORGANISM: Artificial
<220> FEATURE:
<223> OTHER INFORMATION: Chemically synthesized riboswitch
<220> FEATURE:
<221> NAME/KEY: misc_feature
<222> LOCATION: (27)..(27)
<223> OTHER INFORMATION: complementary to nucleotide 59
<220> FEATURE:
<221> NAME/KEY: misc_feature
<222> LOCATION: (28)..(28)
<223> OTHER INFORMATION: complementary to nucleotide 58
<220> FEATURE:
<221> NAME/KEY: misc_feature
<222> LOCATION: (29)..(29)
<223> OTHER INFORMATION: complementary to nucleotide 57
<220> FEATURE:
<221> NAME/KEY: misc_feature
<222> LOCATION: (30)..(30)
<223> OTHER INFORMATION: complementary to nucleotide 56
<220> FEATURE:
<221> NAME/KEY: misc_feature
<222> LOCATION: (56)..(59)
<223> OTHER INFORMATION: n is a, c, g, or u

<400> SEQUENCE: 84
acuuuuuuuu uuuuuuuuuu uuuuuunnnn auaccagccg aaaggcccuu ggcagnnnn          59

<210> SEQ ID NO 85
<211> LENGTH: 60
<212> TYPE: RNA
<213> ORGANISM: Artificial
<220> FEATURE:
<223> OTHER INFORMATION: Chemically synthesized riboswitch
```

```
<220> FEATURE:
<221> NAME/KEY: misc_feature
<222> LOCATION: (28)..(28)
<223> OTHER INFORMATION: complementary to nucleotide 60
<220> FEATURE:
<221> NAME/KEY: misc_feature
<222> LOCATION: (29)..(29)
<223> OTHER INFORMATION: complementary to nucleotide 59
<220> FEATURE:
<221> NAME/KEY: misc_feature
<222> LOCATION: (30)..(30)
<223> OTHER INFORMATION: complementary to nucleotide 58
<220> FEATURE:
<221> NAME/KEY: misc_feature
<222> LOCATION: (31)..(31)
<223> OTHER INFORMATION: complementary to nucleotide 57
<220> FEATURE:
<221> NAME/KEY: misc_feature
<222> LOCATION: (57)..(60)
<223> OTHER INFORMATION: n is a, c, g, or u

<400> SEQUENCE: 85
acuuuuuuuu uuuuuuuuuu uuuuuuunnn nauaccagcc gaaaggcccu uggcagnnnn      60

<210> SEQ ID NO 86
<211> LENGTH: 61
<212> TYPE: RNA
<213> ORGANISM: Artificial
<220> FEATURE:
<223> OTHER INFORMATION: Chemically synthesized riboswitch
<220> FEATURE:
<221> NAME/KEY: misc_feature
<222> LOCATION: (29)..(29)
<223> OTHER INFORMATION: complementary to nucleotide 61
<220> FEATURE:
<221> NAME/KEY: misc_feature
<222> LOCATION: (30)..(30)
<223> OTHER INFORMATION: complementary to nucleotide 60
<220> FEATURE:
<221> NAME/KEY: misc_feature
<222> LOCATION: (31)..(31)
<223> OTHER INFORMATION: complementary to nucleotide 59
<220> FEATURE:
<221> NAME/KEY: misc_feature
<222> LOCATION: (32)..(32)
<223> OTHER INFORMATION: complementary to nucleotide 58
<220> FEATURE:
<221> NAME/KEY: misc_feature
<222> LOCATION: (58)..(61)
<223> OTHER INFORMATION: n is a, c, g, or u

<400> SEQUENCE: 86
acuuuuuuuu uuuuuuuuuu uuuuuuunn nnauaccagc cgaaaggccc uuggcagnnn      60 n                                                                    61

<210> SEQ ID NO 87
<211> LENGTH: 62
<212> TYPE: RNA
<213> ORGANISM: Artificial
<220> FEATURE:
<223> OTHER INFORMATION: Chemically synthesized riboswitch
<220> FEATURE:
<221> NAME/KEY: misc_feature
<222> LOCATION: (30)..(30)
<223> OTHER INFORMATION: complementary to nucleotide 62
<220> FEATURE:
<221> NAME/KEY: misc_feature
<222> LOCATION: (31)..(31)
<223> OTHER INFORMATION: complementary to nucleotide 61
<220> FEATURE:
<221> NAME/KEY: misc_feature
<222> LOCATION: (32)..(32)
<223> OTHER INFORMATION: complementary to nucleotide 60
<220> FEATURE:
```

```
<221> NAME/KEY: misc_feature
<222> LOCATION: (33)..(33)
<223> OTHER INFORMATION: complementary to nucleotide 59
<220> FEATURE:
<221> NAME/KEY: misc_feature
<222> LOCATION: (59)..(62)
<223> OTHER INFORMATION: n is a, c, g, or u

<400> SEQUENCE: 87
acuuuuuuuu uuuuuuuuuu uuuuuuuuun nnnauaccag ccgaaaggcc cuuggcagnn      60 nn                                                                    62

<210> SEQ ID NO 88
<211> LENGTH: 55
<212> TYPE: RNA
<213> ORGANISM: Artificial
<220> FEATURE:
<223> OTHER INFORMATION: Chemically synthesized riboswitch
<220> FEATURE:
<221> NAME/KEY: misc_feature
<222> LOCATION: (23)..(23)
<223> OTHER INFORMATION: complementary to nucleotide 55
<220> FEATURE:
<221> NAME/KEY: misc_feature
<222> LOCATION: (24)..(24)
<223> OTHER INFORMATION: complementary to nucleotide 54
<220> FEATURE:
<221> NAME/KEY: misc_feature
<222> LOCATION: (25)..(25)
<223> OTHER INFORMATION: complementary to nucleotide 53
<220> FEATURE:
<221> NAME/KEY: misc_feature
<222> LOCATION: (26)..(26)
<223> OTHER INFORMATION: complementary to nucleotide 52
<220> FEATURE:
<221> NAME/KEY: misc_feature
<222> LOCATION: (52)..(55)
<223> OTHER INFORMATION: n is a, c, g, or u

<400> SEQUENCE: 88
acyyyyyyyy yyyyyyyyyy yynnnauac cagccgaaag gcccuuggca gnnnn           55

<210> SEQ ID NO 89
<211> LENGTH: 56
<212> TYPE: RNA
<213> ORGANISM: Artificial
<220> FEATURE:
<223> OTHER INFORMATION: Chemically synthesized riboswitch
<220> FEATURE:
<221> NAME/KEY: misc_feature
<222> LOCATION: (24)..(24)
<223> OTHER INFORMATION: complementary to nucleotide 56
<220> FEATURE:
<221> NAME/KEY: misc_feature
<222> LOCATION: (25)..(25)
<223> OTHER INFORMATION: complementary to nucleotide 55
<220> FEATURE:
<221> NAME/KEY: misc_feature
<222> LOCATION: (26)..(26)
<223> OTHER INFORMATION: complementary to nucleotide 54
<220> FEATURE:
<221> NAME/KEY: misc_feature
<222> LOCATION: (27)..(27)
<223> OTHER INFORMATION: complementary to nucleotide 53
<220> FEATURE:
<221> NAME/KEY: misc_feature
<222> LOCATION: (53)..(56)
<223> OTHER INFORMATION: n is a, c, g, or u

<400> SEQUENCE: 89
acyyyyyyyy yyyyyyyyyy yyynnnauа ccagccgaaa ggcccuuggc agnnnn          56
```

```
<210> SEQ ID NO 90
<211> LENGTH: 57
<212> TYPE: RNA
<213> ORGANISM: Artificial
<220> FEATURE:
<223> OTHER INFORMATION: Chemically synthesized riboswitch
<220> FEATURE:
<221> NAME/KEY: misc_feature
<222> LOCATION: (25)..(25)
<223> OTHER INFORMATION: complementary to nucleotide 57
<220> FEATURE:
<221> NAME/KEY: misc_feature
<222> LOCATION: (26)..(26)
<223> OTHER INFORMATION: complementary to nucleotide 56
<220> FEATURE:
<221> NAME/KEY: misc_feature
<222> LOCATION: (27)..(27)
<223> OTHER INFORMATION: complementary to nucleotide 55
<220> FEATURE:
<221> NAME/KEY: misc_feature
<222> LOCATION: (28)..(28)
<223> OTHER INFORMATION: complementary to nucleotide 54
<220> FEATURE:
<221> NAME/KEY: misc_feature
<222> LOCATION: (54)..(57)
<223> OTHER INFORMATION: n is a, c, g, or u

<400> SEQUENCE: 90
acyyyyyyyy yyyyyyyyyy yyyynnnnau accagccgaa aggcccuugg cagnnnn         57

<210> SEQ ID NO 91
<211> LENGTH: 58
<212> TYPE: RNA
<213> ORGANISM: Artificial
<220> FEATURE:
<223> OTHER INFORMATION: Chemically synthesized riboswitch
<220> FEATURE:
<221> NAME/KEY: misc_feature
<222> LOCATION: (26)..(26)
<223> OTHER INFORMATION: complementary to nucleotide 58
<220> FEATURE:
<221> NAME/KEY: misc_feature
<222> LOCATION: (27)..(27)
<223> OTHER INFORMATION: complementary to nucleotide 57
<220> FEATURE:
<221> NAME/KEY: misc_feature
<222> LOCATION: (28)..(28)
<223> OTHER INFORMATION: complementary to nucleotide 56
<220> FEATURE:
<221> NAME/KEY: misc_feature
<222> LOCATION: (29)..(29)
<223> OTHER INFORMATION: complementary to nucleotide 55
<220> FEATURE:
<221> NAME/KEY: misc_feature
<222> LOCATION: (55)..(58)
<223> OTHER INFORMATION: n is a, c, g, or u

<400> SEQUENCE: 91
acyyyyyyyy yyyyyyyyyy yyyyynnnna uaccagccga aaggcccuug gcagnnnn         58
```

ARTIFICIAL RIBOSWITCH FOR CONTROLLING PRE-MRNA SPLICING

RELATED APPLICATIONS

The present application claims priority to U.S. Provisional Application No. 60/686,838, filed Jun. 1, 2005, the disclosure of which is incorporated by reference herein in its entirety.

GOVERNMENT INTEREST

This invention was made with government support in part by the Department of Defense, Grant Number BC023235. The government may have certain rights in this invention.

BACKGROUND

The vast majority of structural genes in higher eukaryotes contain intervening sequences (introns) whose precise removal from the mRNA precursors (pre-mRNAs) is essential for proper gene expression. Excision of introns from nuclear pre-mRNAs is catalyzed by the spliceosome, perhaps the most complex ribonucleoprotein (RNP) assembly in the cell (Nilsen, 2003). A number of RNA-RNA and RNA-protein interactions involving five small nuclear RNAs (U1, U2, U4, U5 and U6) and many snRNP and non-snRNP proteins mediate the removal of introns and joining of exons (Kramer, 1996; Moore et al., 1993; Newman, 1994; Nilsen, 2003; Will and Luhrmann, 1997).

Pre-mRNAs are spliced in a two-step pathway involving two sequential transesterification reactions. In the first step, pre-mRNA is cleaved at the 5' splice site simultaneously generating two splicing intermediates: a linear first exon RNA, and an intron-second exon RNA in a lariat configuration. In the second step, the 3'-hydroxyl group of the last nucleotide in the first exon makes a nucleophilic attack at the phosphodiester bond separating the intron and the second exon (3' splice site) enabling the joining of two exons and the release of the intron as a lariat (Kramer, 1996; Moore et al., 1993; Newman, 1994; Nilsen, 2003; Will and Luhrmann, 1997).

In higher eukaryotes, three distinct sequences direct the splicing reaction: the 5' splice site (/GURAGY), the branch-point sequence (BPS) (YNYURAC), and the 3' splice site (Y AG/), where a slash (/) denotes a splice site, N denotes any nucleotide, R denotes purine, Y denotes pyrimidine, and underlining indicates the conserved nucleotide. During the early stages of the spliceosome assembly the 5' and the 3' end of the intron are recognized by intermolecular base pairing between U1 snRNA and the 5' splice site (Seraphin et al., 1988; Siliciano and Guthrie, 1988; Zhuang and Weiner, 1986) and by the binding of U2AF to the poly(Y) tract/3' ss AG (Merendino et al., 1999; Ruskin et al., 1988; Wu et al., 1999; Zamore et al., 1992; Zorio and Blumenthal, 1999), respectively. Later in the spliceosome assembly, U1 snRNA-5' splice site base pairing is disrupted and the 5' splice site is bound by U6 snRNA (Kandels-Lewis and Seraphin, 1993; Konforti et al., 1993; Lesser and Guthrie, 1993; Sawa and Abelson, 1992; Sawa and Shimura, 1992; Sontheimer and Steitz, 1993; Wassarman and Steitz, 1992). The branchpoint adenosine is selected in part by intermolecular base pairing between the BPS and U2 snRNA, and the RS domain of U2AF65 stabilizes this interaction (Gaur et al., 1995; Valcarcel et al., 1996). Recently, a one-step assembly of the spliceosome has also been reported (Malca et al., 2003; Stevens et al., 2002).

Pre-mRNAs can also undergo alternative splicing to generate variant mRNAs with diverse and often antagonistic functions (Black, 2003; Clayerie, 2001; Graveley, 2001; Smith and Valcarcel, 2000). Alternative splicing of pre-mRNA is now recognized as the most important source of protein diversity in vertebrates (Maniatis and Tasic, 2002; Mironov et al., 1999; Roberts and Smith, 2002; Thanaraj et al., 2004). It has been estimated that 35-60% of human genes generate transcripts that are alternatively spliced (Johnson et al., 2003; Mironov et al., 1999), and 70-90% of alternative splicing decisions result into the generation of proteins with diverse functions ranging from sex determination to apoptosis (Black, 2003; Kan et al., 2001; Modrek et al., 2001). Importantly, the defective regulation of splice variant expression has been identified as the cause of several genetic disorders (Dredge et al., 2001; Faustino and Cooper, 2003; Garcia-Blanco et al., 2004; Hull et al., 1993; Nissim-Rafinia and Kerem, 2002; Pagani and Baralle, 2004; Phillips and Cooper, 2000), and certain forms of cancer have been linked to unbalanced isoform expression from genes involved in cell cycle regulation or angiogenesis (Krajewska et al., 1996a; Krajewska et al., 1996b; Novak et al., 2001; Steinman et al., 2004; Venables, 2004; Xerri et al., 1996). Therefore, development of tools that could control pre-mRNA splicing may have far-reaching effects in biotechnology and medicine.

Initial efforts aimed at controlling pre-mRNA splicing exploited the intrinsic property of nucleic acids to bind specific complementary pre-mRNA sequence and inhibit/modulate splicing (Dominski and Kole, 1993). However, susceptibility of antisense oligonucleotides to nuclease digestion, off-target effects, and problems associated with the delivery and localization led to the realization that better methods are needed (Heidenreich et al., 1995). Bifunctional molecules that act like an antisense oligonucleotide, but carry the binding site for a known splicing factor have proved to be useful in reprogramming pre-mRNA splicing (Cartegni and Krainer, 2003; Eperon and Muntoni, 2003; Skordis et al., 2003; Villemaire et al., 2003). Although bifunctional molecules have overcome some of the problems associated with antisense-based approach, the need to include various chemical modifications limit their utility.

Notably, all of the above mentioned approaches function in a constitutive manner, i.e., an antisense oligonucleotide or a bifunctional molecule directed to inhibit the splicing will continue to do so as long as the oligonucleotide is available. Given that splicing of many pre-mRNAs is regulated in a tissue or development specific manner (Black, 2003; Lopez, 1998), to be able to switch off/on the splicing would be of broad application in gene-based therapy and functional genomics. Although a recently reported small molecule-based approach, which could activate splicing by simultaneously binding to a protein containing the splicing activation domain and a second protein bound to the pre-mRNA has the potential to act as a splicing switch, expression of heterologous proteins and maintaining small molecule-protein interplay makes this approach complicated (Graveley, 2005).

Accordingly, there is a need to develop novel approaches to regulate RNA splicing or alternative RNA splicing in a condition-specific manner.

SUMMARY

One aspect of the present invention relates to artificial riboswitches that specifically regulate the splicing of their cognate pre-mRNA in the presence of a condition that may affect or bind to the riboswitches. For example, one embodiment of the invention relates to artificial riboswitches that show affinity to, or are regulated by, theophylline (Jenison et al., 1994), wherein the theophylline-dependent or theophylline binding riboswitches regulate RNA splicing in the presence of theophylline.

Another aspect of the present invention relates to methods of regulating (e.g., inhibiting or inducing) the splicing of a pre-mRNA (e.g., AdML-Theo29AG, SEQ ID NO: 6) in a theophylline-dependent manner, wherein the 3' splice site AG is embedded within the theophylline binding aptamer. In one embodiment, the BPS-to-3' splice distance as well as the location of the 3' splice site AG within the aptamer is designed such that it confers theophylline-dependent control of RNA splicing. In a preferred embodiment, the distance between BPS and 3' splice site AG is between 21 to 39 nucleotides (e.g., 29) starting from the C of the BPS and ending with the G of the 3' splice site. In another preferred embodiment, the pre-mRNA splicing can be regulated in vitro, in vivo, or ex vivo. It is noted that theophylline mediated control of pre-mRNA splicing is specific. First, theophylline specifically blocks the step II of the splicing. Second, a small molecule ligand similar in shape and size of theophylline has no effect on the splicing of pre-mRNAs modulated by theophylline. Third, theophylline fails to exert any influence on the splicing of a pre-mRNA that does not contain its binding site (aptamer). Finally, theophylline-dependent modulation of pre-mRNA splicing is functionally relevant.

Another aspect of the present invention relates to methods of optimizing the BPS-to-3' splice distance so that theophylline can effectively modulate the pre-mRNA splicing. The method comprises the steps of generating riboswitches of various distance between the BPS and the 3' splice (AG), measuring the effect of theophylline on RNA splicing in a pre-mRNA containing the riboswitches.

Another aspect of the present invention relates to methods of modifying theophylline-dependent aptamers so that the aptamers' affinity to theophylline can be modified (e.g., improved). The method comprises the steps of modifying nucleotides in a theophylline-dependent aptamer, designing pre-mRNA embedding the modified aptamer, and determining the level of RNA splicing.

Another aspect of the present invention relates to methods of identifying aptamers that bind to theophylline, preferably at physiological $Mg^{2+}$ concentration. The method comprises the steps of designing an aptamer and testing the aptamer's affinity to theophylline.

Another aspect of the present invention relates to methods of developing theophylline-dependent bifunctional molecules which can regulate pre-mRNA splicing. The method comprises the steps of designing a bifunctional molecule, where the molecule comprises an antisense domain to an exonic splicing enhancer and a theophylline aptamer; wherein the binding of the antisense domain to the exonic splicing enhance reduces RNA splicing and the introduction of theophylline to a splicing reaction inhibits the binding of the antisense domain to the exonic splicing enhancer. In one embodiment, the stability of a bifunctional molecule may be improved by using phosphorothioate or 2' modified nucleotides.

Another aspect of the present invention relates to bimolecular allosteric hammerhead molecules, which are able to regulate pre-mRNA splicing in a theophylline-dependent manner.

Another aspect of the present invention relates to methods of identifying theophylline-like compounds or test agents. In one embodiment, the method comprises the steps of providing a pre-mRNA containing a theophylline-dependent aptamer wherein the splicing of the pre-mRNA is regulated in the presence of theophylline; contacting a test agent with the pre-mRNA; and determining the level of pre-mRNA splicing in the presence of the agent relative to the absence of the agent. In another embodiment, the method comprises the steps of providing a cell or a subject containing a pre-mRNA comprising a theophylline-dependent aptamer wherein the splicing of the pre-mRNA is regulated in the presence of theophylline, contacting the cell or the subject with a test agent, and determining the level of pre-mRNA splicing in the presence of the agent relative to the absence of the agent.

Another aspect of the present invention relates to methods of modulating RNA splicing in a subject using theophylline and a theophylline-dependent riboswitch. The method comprises the steps of introducing into a subject a pre-mRNA containing a theophylline-dependent riboswitch, contact the subject with theophylline, examining the modulation of pre-mRNA splicing in the presence of theophylline.

Another aspect of the present invention relates to methods of placing or inserting a theophylline aptamer into the 5' splice site and determining whether a theophylline-dependent riboswitch would modulate the 5' splice site choice in the presence of theophylline. Another aspect of the present invention relates to methods of modulating RNA splicing comprising the steps of inserting a theophylline aptamer into the 5' splice site and modulating pre-mRNA splicing in the presence of theophylline.

Another aspect of the present invention relates to methods of placing or inserting a theophylline aptamer into the BPS and determining whether a theophylline-dependent riboswitch would modulate pre-mRNA splicing in the presence of theophylline. Another aspect of the present invention relates to methods of modulating RNA splicing comprising the steps of inserting a theophylline aptamer into the BPS and modulating pre-mRNA splicing in the presence of theophylline.

Another aspect of the present invention relates to methods of treating a disease associated with abnormal RNA splicing or a fragment of mutated gene using a theophylline dependent aptamer. In one embodiment, a vector containing the complementary sequence of a theophylline dependent aptamer is introduced into a cell or a subject. The vector may be transcribed to a pre-mRNA and the splicing of the pre-mRNA is dependent on the presence of theophylline. Theophylline or a theophylline-like agent is contacted with or administered to the cell or subject and regulates the splicing of the pre-mRNA. Consequently, abnormal RNA splicing is corrected or inhibited in the presence of theophylline.

DETAILED DESCRIPTION

One aspect of the present invention relates to artificial riboswitches that specifically regulate the splicing of its cognate pre-mRNA in the presence of a condition (e.g., a ligand or a molecule) that triggers the modulation of RNA splicing.

The term "riboswitch" used herein refers to a fragment of nucleic acids inserted by or linked with an aptamer such that the binding of an aptamer-specific ligand or molecule to the aptamer would affect the activity of the fragment. One example of a riboswitch contains a sequence 3' to the BPS, which comprises a poly pyrimidine sequence, the 3' splice site, and an aptamer that is inserted or linked to the 3' splice site region in a way that the pre-mRNA splicing is affected or modulated in the presence of a ligand or molecule specific to the aptamer. Another example of a riboswitch contains a sequence 5' to the BPS, wherein the sequence comprises an aptamer that is associated with (e.g., inserted or linked to) to the 5' splice site in a way that the pre-mRNA splicing is affected or modulated in the presence of a ligand or molecule specific to the aptamer. Yet another example of a riboswitch contains a modified BPS, wherein an aptamer is associated with (e.g., inserted or linked to) the BPS in such a way that pre-mRNA splicing is affected or modulated in the presence of a ligand or molecule specific to the aptamer.

The "aptamer" used herein refers to a fragment (or a domain) of nucleic acid sequence that selectively binds to a ligand or molecule. The introduction of a ligand to a ligand-specific aptamer causes conformational changes within the aptamer and influences nucleic acids adjacent to the aptamer.

Figure 1:
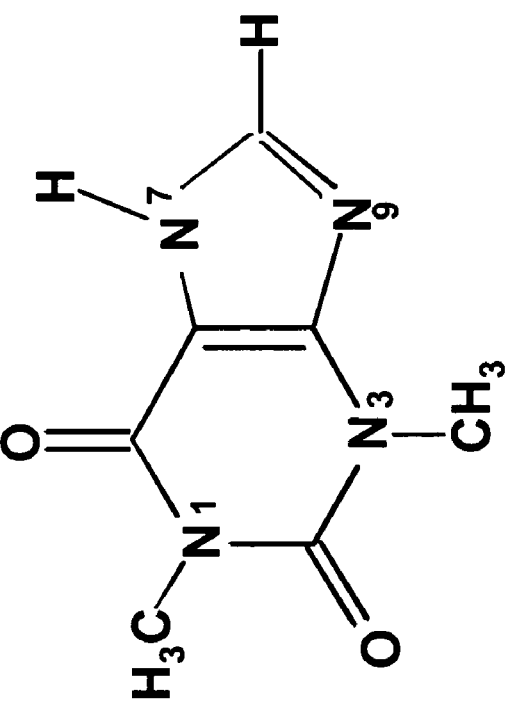
FIG. 1. (A) Structure of theophylline. (B) Sequence and secondary structure of the theophylline binding RNA (SEQ ID NO: 16). The original aptamer numbering is shown (Zimmermann et al., 1997). The residues that are required for theophylline binding are enclosed in the box.
Figure 1:
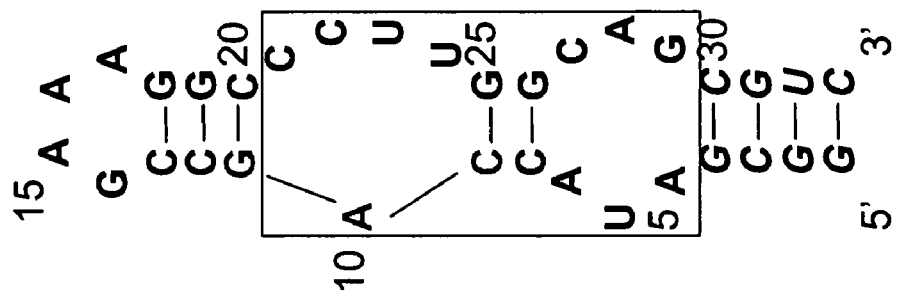

In one embodiment of the present invention, a riboswitch contains a theophylline-dependent aptamer with a nucleic acid sequence of AUACCAGCCGAAAGGCCCUUGGCAG (SEQ ID NO: 10) and a ligand is theophylline (FIGS. 1(A) & (B)). For modulating mRNA splicing, a ligand or molecule specific to an aptamer should meet some or all of the following criteria. First, it should be able to bind its ligand-binding aptamer with high affinity. Second, ligand-aptamer interaction should not require the assistance of any other factor. Third, the ligand-binding site (the aptamer) should be unstructured and only upon the binding of ligand should the aptamer undergo a conformational change or rearrangement. Fourth, the ligand-aptamer binding must be preserved under the conditions that support pre-mRNA splicing. Finally, the ligand should not affect the splicing of a substrate that does not contain its binding site.

A number of ligands such as tobramycin (Wang and Rando, 1995), neomycin (Wallis et al., 1995), ATP (Sassanfar and Szostak, 1993), FMN (Burgstaller and Famulok, 1994) and theophylline (Jenison et al., 1994) have been shown to bind RNAs that were evolved by in vitro selection (Joyce, 1994). All of these ligands meet some of the above mentioned criteria (e.g., the first three requirements). However, since both ATP and FMN are cellular components, and ATP is required for in vitro splicing, a system based on these two molecules might interfere with splicing regulation. To assess the suitability of ligands, the splicing of pre-mRNA not having ligand-dependent aptamer (e.g., AdML-21AG pre-mRNA (Chua and Reed, 2001)) is examined in the presence of these ligands. As a result, theophylline (FIG. 1) exerts no effect on the splicing of AdML-21AG pre-mRNA (see FIG. 8). Accordingly, a preferred ligand is theophylline (FIG. 1(A)) and a preferred aptamer is a theophylline-dependent aptamer (FIG. 1(B)).

Accordingly, examples of riboswitches include but are not limited to, for instance:

1) AC(Y)$_n$AUACCAGCCGAAAGGCCCUUGGCAG, n ranges from 15 to 31 (SEQ ID NOs: 1, 40-55);

2) AC(Y)$_n$AUACCAGCCGAAAGGCCCUUGGCAG, n=21 (SEQ ID NO: 2);

3) AC(Y)$_n$AUACCAGCCGAAAGGCCCUUGGCAG, n=17 (SEQ ID NO: 3);

4) ACUUUUUUUCUUUUUUUUUCCAUACCAGCC-GAAAGGCCCUUGGCAGG (SEQ ID NO: 4);

5) ACUUUUUUUCUUUUUUUUUCCUCAUACCAGCC-GAAAGGCCCUUGGCAG (SEQ ID NO: 5);

6) ACUUUUUUUCUUUUUUUUUCCUCAUACCAGC-CGAAAGGCCCUUGGCAGGA GG (SEQ ID NO: 6);

7) AC(Y)nN$_1$N$_2$N$_3$N$_4$AUACCAGCCGAAAGGCCCUU-GGCAGN'$_4$N$_3$N'$_2$N'$_1$, n ranges from 11 to 27, N$_1$-N$_4$ each denote any nucleotide, N'$_1$-N'$_4$ are complementary to N$_1$-N$_4$, respectively (SEQ ID NOs: 7, 56-71);

8) AC(U)$_n$NNNNAUACCAGCCGAAAGGCCCUUGGCA-GN'N'N'N', n ranges from 11 to 27, N is any nucleotide, N' is complementary to N (SEQ ID NOs: 8, 72-87);

9) AC(Y)$_n$NNNNAUACCAGCCGAAAGGCCCUUGGC-AGN'N'N'N', n ranges from 19 to 23, N is any nucleotide, N' is complementary to N (SEQ ID NOs: 9, 88-91).

As shown below, theophylline mediated inhibition of AdML-Theo29AG (SEQ ID NO: 6) splicing is highly specific: First, theophylline inhibits the splicing of AdML-Theo29AG by blocking the step II of the splicing. Second, a molecule similar in shape and size to theophylline failed to elicit any effect on its splicing. Third, the splicing of a pre-mRNA that does not contain appropriately placed theophylline-binding aptamer remained unaffected in the presence of theophylline. Finally, insertion of theophylline aptamer 8 and 10 nucleotides downstream of the 3' or 5' splice site, respectively failed to elicit any effect on the splicing.

However, the introduction or insertion of theophylline-dependent aptamer at the 3' splice site does not necessarily confer theophylline-dependent regulation of pre-mRNA splicing. Distance as well as the location of 3' splice site AG plays an important role in conferring theophylline-dependent regulation of splicing. To investigate whether formation of RNA-theophylline complex affects pre-mRNA splicing, a derivative of AdML Par pre-mRNA (Gozani et al., 1994) designated AdML-Theo39AG, that has a theophylline aptamer sequence 3' adjacent to the poly (Y) tract was used (FIG. 2, whereas the 3' splice site G is 39 nucleotides away from C marked as 1). AdML-Theo39AG is isogeneic to AdML Par (Gozani et al., 1994) except that AdML-Theo39AG contains a long uninterrupted poly(Y) tract followed by theophylline binding sequence, and the AG dinucleotide at the 3' terminus of AdML Par has been deleted (compare AdML par and AdML-Theo39AG pre-mRNAs, FIGS. 2A-B).

To analyze in vitro splicing, $^{32}$P-labeled RNAs were incubated in HeLa nuclear extract under standard conditions that support splicing (Gaur et al., 1995). After incubation, the splicing reaction was terminated and products were fractionated by electrophoresis on a 13% denaturing polyacrylamide gel. The wild type substrate, as expected, underwent both steps of the splicing reaction with normal kinetics, as evidenced by the presence of lariat containing RNAs and spliced mRNA (FIG. 2C; lanes 3-5). Surprisingly, the splicing of AdML-Theo39AG substrate gave rise to the accumulation of lariat-exon 2, suggesting that splicing was strongly affected at the second step (FIG. 2C, compare lanes 3-5 with lanes 7-9).

To rule out the possibility that the observed step II splicing inhibition in AdML-Theo39AG might be due to a higher order structure formed by the presence of aptamer sequence, a derivative of human β-globin pre-mRNA (Hβ-Theo41AG) in which the 3' splice site AG is engineered to be the part of the theophylline binding sequence was constructed. The in vitro splicing of Hβ-Theo41AG pre-mRNA also resulted in the inhibition of the step II of the splicing.

It has been previously shown that pre-mRNA derivatives bearing mutations of the splice sites (Aebi et al., 1986; Lamond et al., 1987; Newman et al., 1985; Ruskin and Green, 1985; Seraphin and Rosbash, 1990) or the branchpoint (Freyer et al., 1987; Gaur et al., 1997; Hornig et al., 1986; Query et al., 1994) can undergo the first step of the splicing, giving rise to a lariat-exon 2 intermediate that is blocked for the second step. To examine whether mutation of the splice sites or branch point might be the cause of step II splicing inhibition, AdML-Theo39AG substrate was subjected to reverse transcription and PCR. The amplified DNA was cloned into pCR2.1 vector using a TA cloning kit according to the instructions provided by the manufacturer (Invitrogen). Sequencing of 20 randomly selected clones revealed no mutations, suggesting that a mutation of the splice sites or the branchpoint is not the cause of step II splicing inhibition.

Figure 2:
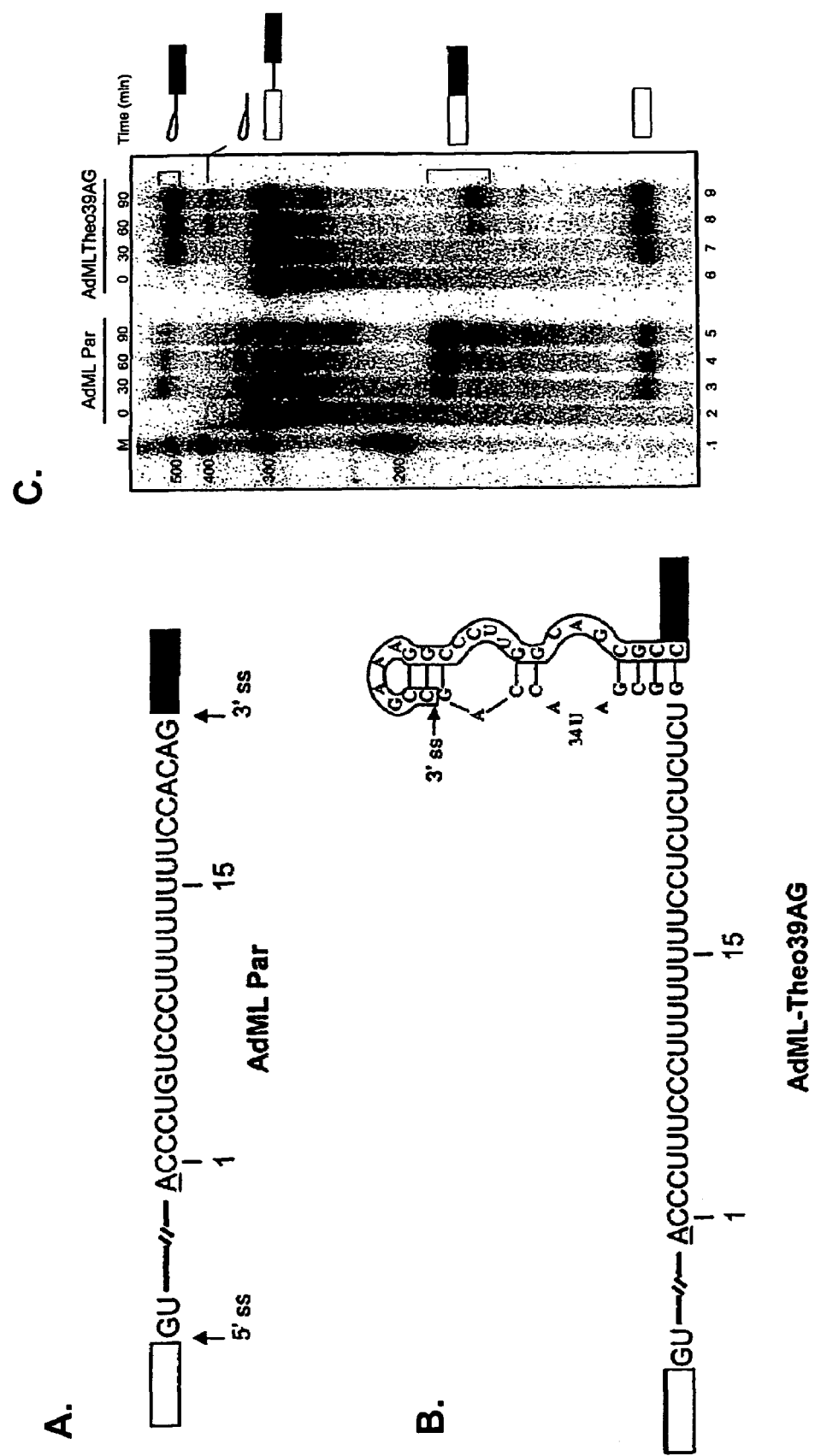
FIG. 2. BPS-to-theophylline aptamer distance affects the second step of the splicing. (A) and (B), diagrams of AdML Par (SEQ ID NO: 17) and AdML-Theo39AG (SEQ ID NO: 18) pre-mRNAs, respectively. Underlined A represents the branchpoint. The boxed residues in theophylline aptamer represent exon 2. (C), Splicing time course with the AdML Par and AdML-Theo39AG substrates. $^{32}$P-Labeled pre-mRNAs were incubated in HeLa nuclear extract at 30° C. for the times indicated above each lane (see materials and methods section for experimental details). Total RNA isolated from each sample was fractionated on a 13% polyacrylamide denaturing gel. The bands corresponding to intermediates and spliced products are indicated. M, Century™-plus RNA size marker (Ambion).

To further investigate why AdML-Theo39AG pre-mRNA failed to undergo the second step of the splicing, we examined the 3' half of the intron. As illustrated in FIG. 2, the sequence encompassing the BPS-to-AG and poly(Y)-to-AG in AdML Par and AdML-Theo39AG indicate striking differences. In AdML Par the 3' ss AG is located 23 nucleotides downstream of the BPS, whereas in AdML-Theo39AG this distance is 39 nucleotides (compare FIGS. 2 A and B). In addition, the poly(Y)-to-AG distance in AdML Par and AdML-Theo39AG is 4 and 11 nucleotides, respectively. Furthermore, in AdML-Theo39AG the sequence between the poly(Y) tract and 3' ss AG contains several purines. It has been previously proposed that a long BPS-to-AG distance and the presence of purine residues preceding the 3' ss AG not only affect not only the efficiency of the second step of the splicing, but also the selection of the correct 3' splice site (Chua and Reed, 2001; Luukkonen and Seraphin, 1997; Patterson and Guthrie, 1991).

To determine whether the aforementioned reasons could be the cause of step II splicing inhibition, an AdML derivative with BPS-to-AG distance of 29 nucleotides and the sequence between the poly(Y) tract and AG bearing the substitutions of cytidine for guanosine was synthesized (FIG. 3A; AdML-Theo-29AG). The in vitro splicing results of this pre-mRNA presented in FIG. 3B demonstrate that lowering of the BPS-to-AG distance has indeed rescued the step II splicing inhibition. Quantification of this data indicates that unlike AdML-Theo-39AG where less than 10% of the pre-mRNA is converted into the spliced product, ~26% of AdML-Theo-29AG pre-mRNA is converted into mRNA (compare lanes 7-9, FIG. 2C with lanes 2-4, FIG. 3B). Remarkably, theophylline could efficiently inhibit the step II of the splicing in a dose dependent manner, as evidenced by the decrease in the amount of the second step products, i.e., lariat and mRNA (FIG. 3B, compare lanes 2-5 with lanes 6-17). This conclusion is further supported by the fact that in the presence of theophylline, splicing of AdML-Theo-29AG pre-mRNA resulted in the accumulation of the lariat-exon 2 (FIG. 3C). Quantification of the results presented in FIG. 3D indicate that 0.5 mM theophylline was able to inhibit the splicing of AdML-Theo-29AG by ~50%, and at 2.0 mM theophylline, ~75% inhibition was achieved. To rule out the possibility that the observed results are substrate specific, a derivative of MINX pre-mRNA (Zillmann et al., 1988) (MINX-Theo28AG) carrying the high affinity theophylline binding aptamer between the poly (Y) tract and 3' splice site AG was synthesized. The in vitro splicing of MINX-Theo28AG pre-mRNA indicates that theophylline-RNA interaction could efficiently inhibit the step II of the splicing, confirming the generality of this approach. Accordingly, the BPS-to-AG distance plays a role in theophylline-dependent modulation of RNA splicing.

Although lowering of BPS-to-AG distance from 39 to 29 nucleotides has relieved step II splicing inhibition in the absence of theophylline, yet compared to the parent substrate the efficiency of the second step of splicing of AdML-Theo-29AG remains low (FIG. 2C, compare lanes 3-5 with FIG. 3B, lanes 2-5). To assess whether further lowering of BPS-to-AG distance would improve the step II splicing efficiency, two substrates, AdML-Theo-27AG and AdML-Theo-Stem21AG, were constructed following standard PCR-based cloning (see materials and methods). In AdML-Theo-27AG, the BPS-to-AG distance is 27 nucleotides, and the lower stem of theophylline aptamer contains only a single base-pair (FIG. 4A). On the other hand, the BPS-to-AG distance in AdML-Theo-Stem21AG is 21 nucleotides, but the proximal AG is no longer located within the theophylline binding pocket (FIG. 5A).

Figure 3:
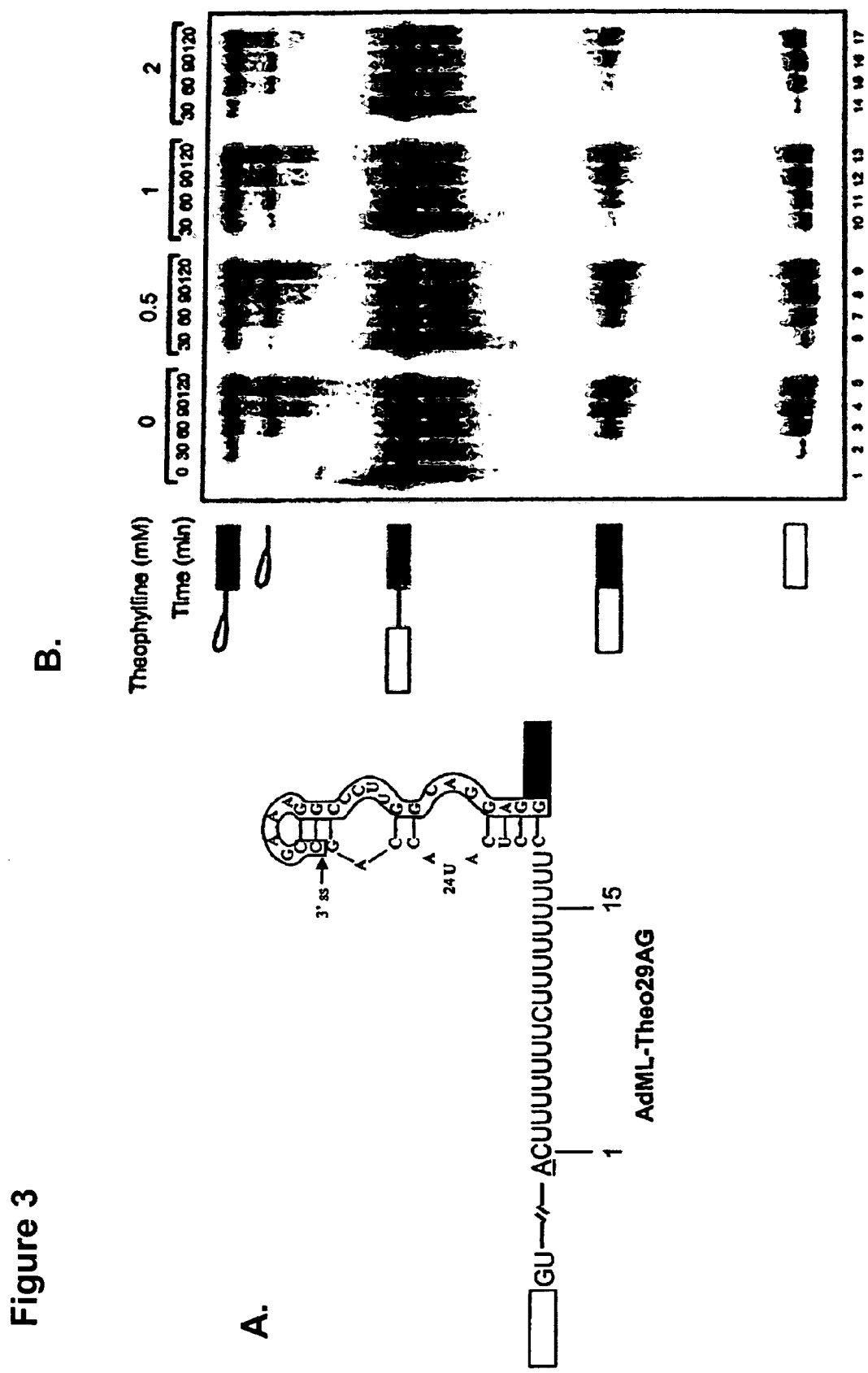
FIG. 3. Lowering of BPS-to-AG distance rescues step II of the splicing and confers theophylline-dependent regulation of splicing. (A) Schematic representation of AdML-Theo29AG pre-mRNA (SEQ ID NO: 6). (B), Splicing time course with the AdML-Theo29AG substrate. $^{32}$P-Labeled AdML-Theo29AG pre-mRNA was subjected to in vitro splicing in the absence (lanes 1-5) or with indicated concentration of theophylline (lanes 6-17). The extracted RNA was fractionated on a 13% polyacrylamide denaturing gel. The bands corresponding to intermediates and spliced products are indicated on left (C), Theophylline inhibits the splicing of AdML-Theo29AG pre-mRNA by blocking the step II of the splicing. The amount of the first (lariat-exon 2, triangles) and second step product (mRNA, squares) is plotted as a function of theophylline concentration. (D), Histogram depicting the effect of theophylline on the first and the second step of AdML-Theo29AG splicing at 120 min time point (from B). The first step splicing efficiency was calculated as the ratio of the first step products (lariat-exon 2 and first exon) to the total (pre-mRNA, lariat-exon 2, first exon and mRNA) and normalized to the control (no theophylline). The step II efficiency was calculated as the ratio of spliced mRNA to the total and normalized to the control.
Figure 4:
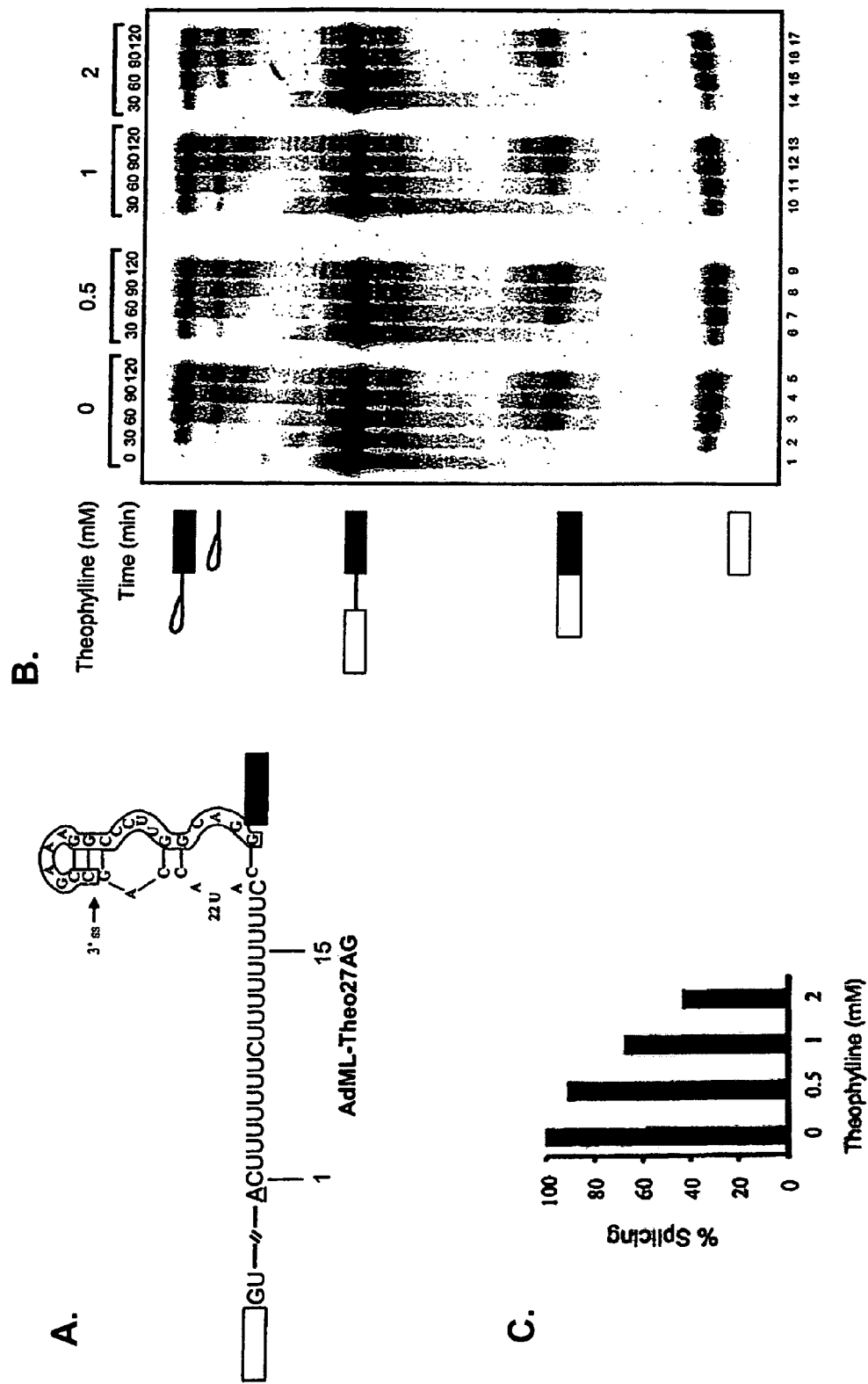
FIG. 4. BPS-to-AG distance as well as the location of AG within the aptamer determines theophylline-dependent regulation of splicing. (A) Schematic representation of AdML-Theo27AG pre-mRNA (SEQ ID NO: 4). (B), Splicing time course with the AdML-Theo27AG substrate. $^{32}$P-Labeled AdML-Theo27AG pre-mRNA was subjected to in vitro splicing in the absence (lanes 1-5) or with indicated concentration of theophylline (lanes 6-17) as described in FIG. 2. The extracted RNA was fractionated on a 13% denaturing polyacrylamide gel. The position of the pre-mRNA, splicing intermediates, and spliced products is indicated on left. (C), Histogram representing the effect of theophylline on the splicing efficiency of AdML-Theo27AG pre-mRNA at 120 min time point (from B). The splicing efficiency was calculated as described in FIG. 3.

The in vitro splicing of AdML-Theo-27AG pre-mRNA demonstrates that lowering of BPS-to-AG distance by 2 nucleotides not only failed to improve the efficiency of the second step of splicing any further (FIGS. 3B and 4B, compare lanes 2-5), but also this pre-mRNA responded less efficiently to theophylline dependent step II splicing inhibition (FIGS. 3D and 4C). In contrast, lowering of BPS-to-AG distance to 21 nucleotides significantly improved the splicing efficiency of AdML-Theo-Stem21AG (compare FIGS. 3B and 4B, lanes 2-5 with FIG. 5B, lanes 1-4). However, like AdML-Theo-27AG, AdML-Theo-Stem21 AG pre-mRNA responded poorly to theophylline dependent splicing inhibition; while 0.5 mM theophylline was able to inhibit the splicing of AdML-Theo-29AG by more than 50%, a 4-fold higher concentration of theophylline could only result in ~40-50% inhibition of AdML-Theo-27AG and AdML-Theo-Stem21AG splicing (FIGS. 3D, 4C-5C).

These results can be explained in terms of the location of the 3' ss AG. In AdML-Theo-29AG, the AG proximal to the BPS is "buried" inside the theophylline-RNA complex, which makes its accessibility to the spliceosome as a 3' acceptor site difficult. This interpretation is in general agreement with the NMR structure of theophylline in complex with its aptamer, which revealed that A28 (the adenine of 3' ss AG) participates in multiple interactions involving G29 and G43 (FIG. 3A) (Zimmermann et al., 1997). These interactions not only add to the stability of RNA-ligand complex, but also likely interfere in the recognition and activation of AG as a 3' ss signal. In the case of AdML-Theo-27AG, although the AG is located inside the theophylline-binding pocket, the deletion of three base pairs in the lower stem apparently compromises with the stability of RNA-theophylline complex. On the other hand, in AdML-Theo-Stem21AG the presence of proximal AG outside the theophylline-binding pocket enables its recognition as the 3' splice site relatively easier. Consequently, the BPS-to aptamer distance as well as the location of AG within the aptamer plays a critical role in conferring theophylline-dependent regulation of pre-mRNA splicing.

The selection and activation of AG as a 3' splice site is a complex phenomenon in which several step II splicing factors make functionally important contacts near the 3' end of the intron (Chiara et al., 1997; van Nues and Beggs, 2001 and references there in). The results presented in the previous section strongly suggest that sequestering of the AG within the theophylline-RNA complex prevent such protein-RNA contact(s). If that is true, then relocation of theophylline aptamer to a position that has no apparent contribution in the selection and activation of AG will have no effect on the splicing.

Figure 6:
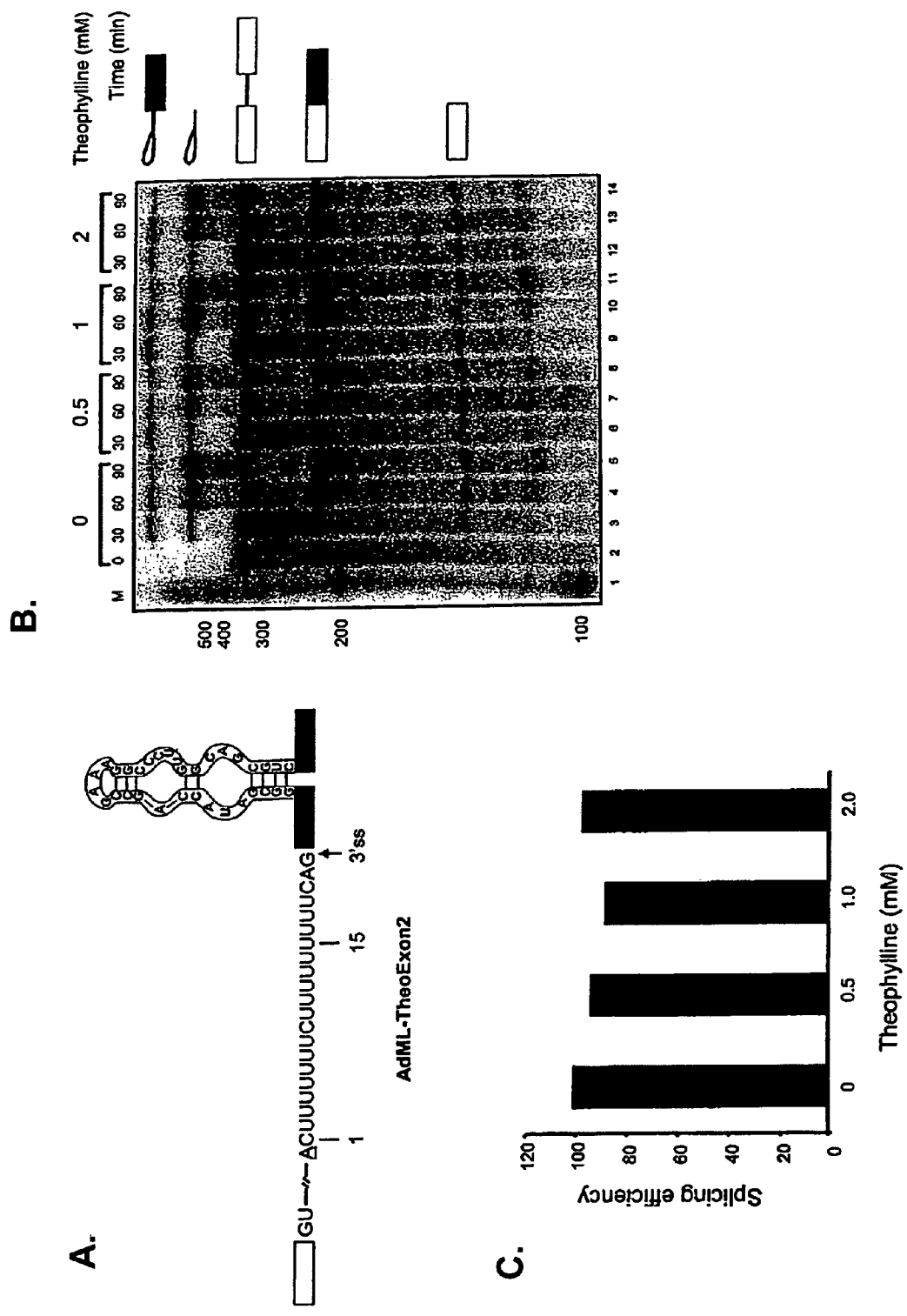
FIG. 6. Theophylline-dependent inhibition of the second step of the splicing is functionally relevant. (A) Schematic representation of AdML-TheoExon 2 pre-mRNA (SEQ ID NO: 20). (B), Splicing time course with the AdML-TheoExon 2 substrate. $^{32}$P-Labeled AdML-TheoExon2 pre-mRNA was subjected to in vitro splicing in the absence (lanes 2-5) or with indicated concentration of theophylline (lanes 6-14) as described in FIG. 2. The extracted RNA was fractionated on a 13% polyacrylamide denaturing gel. The position of the pre-mRNAs, splicing intermediates, and spliced products is indicated on right. M, Century™-plus RNA size marker (Ambion). (C), Histogram representing the effect of theophylline on the splicing efficiency of AdML-TheoExon 2 pre-mRNA at 120 min time point (from B) as described in FIG. 4.

To test this hypothesis, we decided to synthesize an AdML pre-mRNA derivative, termed AdML-TheoExon 2, in which the theophylline-binding site was moved eight nucleotides downstream of the 3' ss (FIG. 6). The in vitro splicing results presented in FIG. 6B demonstrate that AdML-TheoExon 2 pre-mRNA underwent both steps of the splicing with normal kinetics, and unlike AdML-Theo29AG, addition of theophylline had no effect on the outcome of either step of the splicing (compare FIG. 3B, lanes 6-17 with FIG. 6B, lane 6-14). The splicing of AdML-Theo+10*pre-mRNA in which theophylline aptamer was inserted 10 nucleotides downstream of the 5' splice site also remained unaltered in the presence of theophylline (data not shown). Thus, only the functionally important elements of pre-mRNA could be the target of theophylline-dependent control of pre-mRNA splicing.

It has been previously shown that in vitro, spliceosome assembly on pre-mRNA can proceed through one-step assembly (Malca et al., 2003; Stevens et al., 2002), or via a coordinated assembly of complexes E→A→B→C with the catalytic steps of splicing occurring in the complex C (Reed and Palandjian, 1997). In addition, the efficiency of the spliceosome assembly and the intermediate steps can be monitored by native gel electrophoresis (Konarska and Sharp, 1986).

Figure 7:
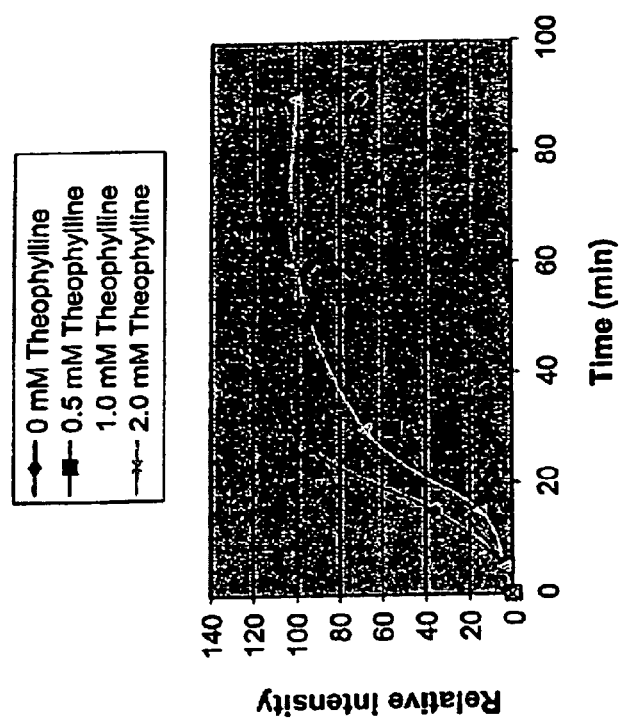
FIG. 7. Analysis of the effect of theophylline on spliceosomal complexes. (A) AdML-Theo29AG pre-mRNA (SEQ ID NO: 6) was incubated in HeLa nuclear extract under the conditions that support pre-mRNA splicing for the times indicated above each lane at 30° C. in the absence (lanes 1-6) or presence (lanes 7-24) of theophylline. The complexes were separated on a 2% agarose gel. The bands representing complex H, A, B and C are marked on the left. (B), The relative intensity of the splicing complex C formed in the absence or presence of theophylline as a function of time is indicated.
Figure 7:
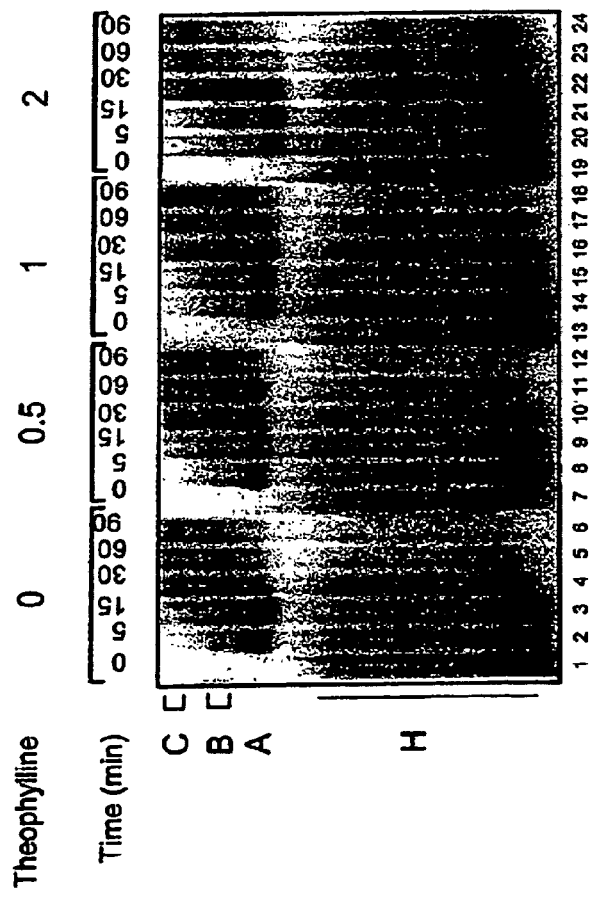

To investigate the effect of theophylline on spliceosome assembly, $^{32}$P-labeled AdML-Theo-29AG pre-mRNA was incubated under splicing conditions in the absence or presence of theophylline. Aliquots were removed at various time points, followed by the separation of complexes on native agarose gels according to the published protocol (Das and Reed, 1999). In the absence of theophylline, complex A was detected as early as 5 min and converted into B/C complex thereafter. Complex B/C appeared after 5 min and peaked between 15-30 min, and after 30 min declined steadily. In the presence of theophylline, the kinetics of complexes A and B/C formation is not very different; complex A appeared at 5 min and decreased thereafter. However, the amount of complexes B/C steadily accumulated (FIG. 7A, compare lanes 4-6 with lanes 9-12, 15-18 and 21-24). In addition, complex H, which almost completely disappeared after 30 min in the absence of theophylline, also accumulated even after 60-90 min of incubation (FIG. 7A, compare lanes 5-6 with lanes 22-24). Quantitation of these results presented in FIG. 7B indicate that theophylline-dependent inhibition of the step II of splicing leads to the accumulation of complex C, which is consistent with previously published reports in which mutation of the 3' splice site (Gozani et al., 1994) or the addition of boric acid, both of which specifically inhibit step II of the splicing, led to the accumulation of complexes B/C (Shomron and Ast, 2003; Shomron et al., 2002).

It is noted that the theophylline-mediated control of pre-mRNA splicing is highly specific. The extraordinary ability with which the splicing regulators discriminate between a specific and a non-specific RNA target play a critical role in the precise regulation of pre-mRNA splicing. For example, both U2AF65 (Zamore et al., 1992) and Sxl (Sakamoto et al., 1992) are poly(Y) tract binding proteins and yet, they utilize different mechanisms (Banerjee et al., 2003; Singh et al., 2000; Singh et al., 1995) for recognizing polypyrimidine tracts and perform different functions; while U2AF65 is a splicing activator, Sxl is a repressor of splicing (Valcarcel et al., 1993). Thus, before theophylline could be employed as a splicing regulator its specificity must be established. First, theophylline should not affect the splicing of a substrate, which does not contain its binding site. Second, molecules that are similar in size and shape to theophylline should not inhibit the splicing of the pre-mRNA that contains theophylline-binding sequence.

To address the first issue, we examine the splicing of AdML-21AG (Chua and Reed, 2001), a pre-mRNA that does not contain the binding site for theophylline, but otherwise is identical to AdML-Theo-29AG (Compare FIGS. 3A and 8A). The results shown in FIGS. 8B and C demonstrate that the splicing of AdML-21AG pre-mRNA remained virtually unaffected even at the maximum tested dose of theophylline.

Figure 9:
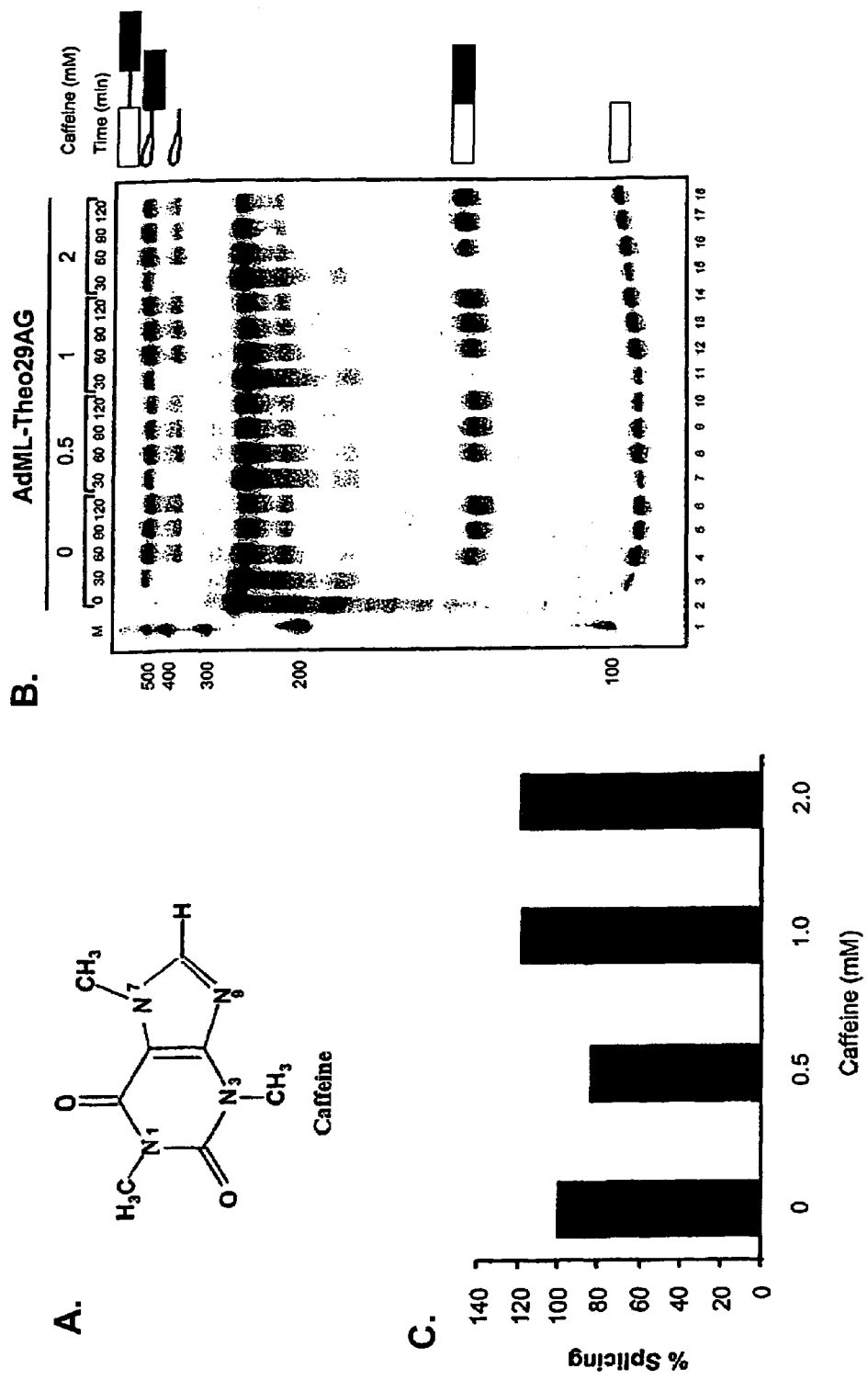
FIG. 9. Splicing of AdML-Theo29AG pre-mRNA (SEQ ID NO: 6) remained unaffected in the presence of Caffeine. (A) Structure of caffeine. (B), Splicing time course with the AdML-Theo29AG pre-mRNA. $^{32}$P-Labeled AdML-Theo29AG pre-mRNA was subjected to in vitro splicing in the absence (lanes 2-6) or with increasing concentration of theophylline (lanes 7-18) as described in FIG. 2. The extracted RNA was fractionated on a 13% polyacrylamide denaturing gel. The position of the pre-mRNAs, splicing intermediates, and spliced products is indicated on right. (C), Histogram representing the effect of caffeine on the splicing efficiency of AdML-29AG pre-mRNA at 120 min time point (from B) as described in FIG. 4.

The second issue was addressed by examining the splicing of AdML-Theo-29AG in the presence of caffeine (FIG. 9). Caffeine differs from theophylline only by a methyl group at the N-7 position in the imidazole ring, yet binds to theophylline aptamer with 10,000-fold lower affinity (FIG. 9A) (Jenison et al., 1994). Uniformly labeled AdML-Theo-29AG was incubated in HeLa nuclear extract in the absence or with increasing concentrations of caffeine, and the products of the splicing reaction were analyzed by denaturing 13% PAGE. The splicing gel of FIG. 9B shows that even at 2.0 mM concentration, caffeine failed to elicit any noticeable effect on the splicing of AdML-Theo-29AG pre-mRNA. In contrast, a similar concentration of theophylline was able to inhibit the splicing of AdML-Theo-29 AG by more than 70% (compare FIGS. 3B, lanes 6-17 and 9B, lanes 7-18). Collectively these results suggest that theophylline-mediated inhibition of AdML-Theo29AG splicing is highly specific.

Figure 10:
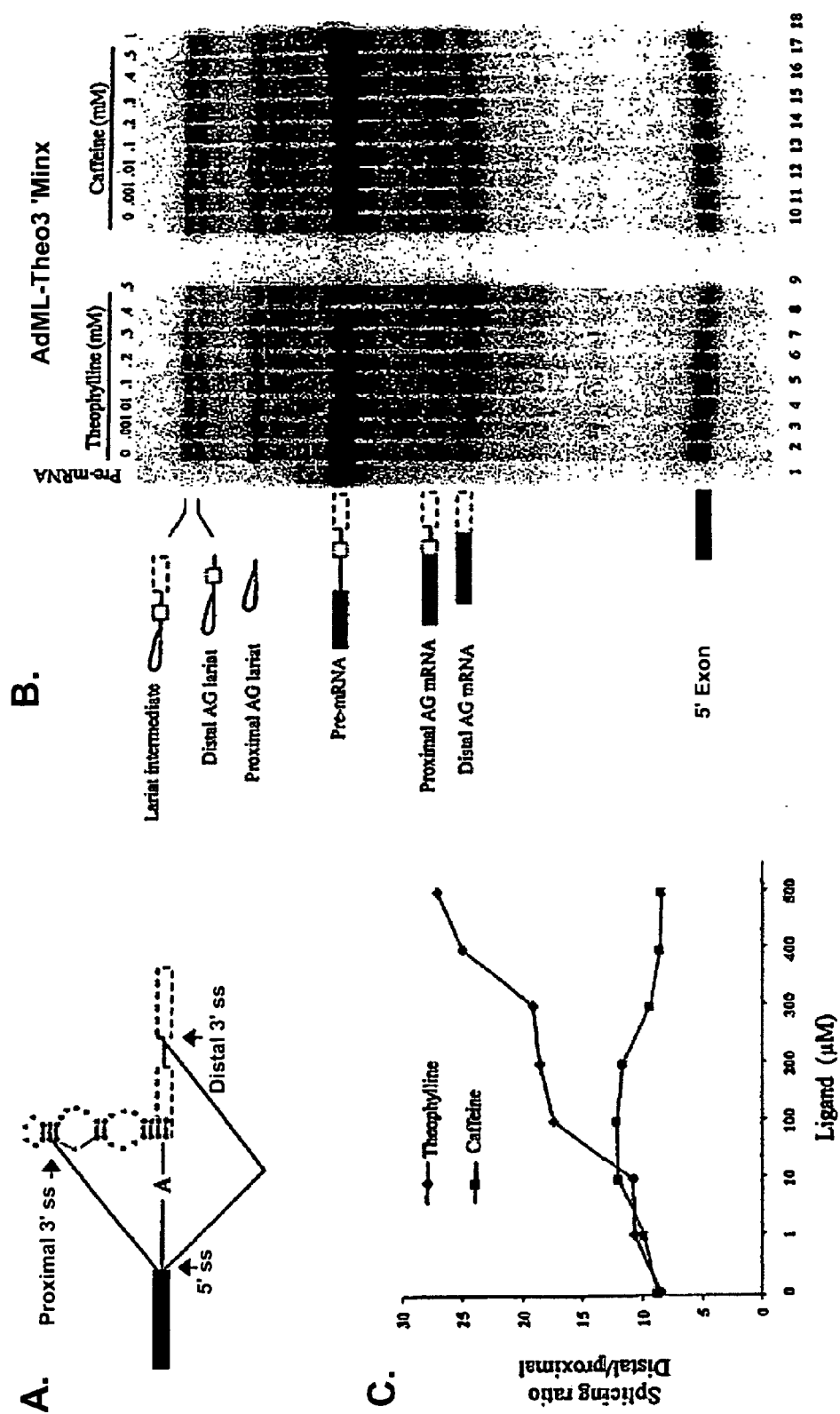
FIG. 10. Theophylline mediated regulation of alternative pre-mRNA splicing. (A) Schematic representation of AdML-Theo 3' Minx pre-mRNA. (B) In vitro splicing of AdML-Theo 3' Minx pre-mRNA. (C) Graphical representation of the ratio of distal to proximal 3' splice as a function of theophylline/caffeine.

Alternative splicing plays an important role in the regulation of gene expression in higher eukaryotes. Alternative splicing is normally regulated by the regulatory proteins, which bind to the specific regions of pre-mRNA and enhance or repress the ability of the spliceosome to recognize the splice sites flanking the regulated exon (Black, 2003; Graveley, 2001). To demonstrate that RNA-small molecule interaction could also regulate alternative splicing, a model pre-mRNA in which two 3' splice sites competing for a common 5' splice site was generated following standard molecular biology techniques (FIG. 10, AdML-Theo-3'Minx). In AdML-Theo-3'Minx pre-mRNA, the proximal 3' ss AG is embedded within the theophylline-binding sequence, while the distal 3' splice site is unmodified. It was contemplated that the binding of theophylline to its target will repress the recognition of the proximal 3' splice site thereby, redirecting the splicing machinery to activate the distal 3' splice site. To test this, uniformly labeled AdML-Theo-3'Minx pre-mRNA (~10 fmol) was incubated in HeLa nuclear extract in the absence or presence of theophylline. In the control splicing, theophylline was replaced by caffeine. As illustrated in FIG. 10, in the absence of theophylline both proximal as well as distal 3' splice sites were utilized to the same degree (FIG. 10, lane 2). Importantly, the addition of theophylline, but not caffeine, to the splicing reaction increased the ratio of distal to proximal 3' splice site. Quantitation of the data revealed that 0.5 mM theophylline increased the ratio of distal to proximal 3' splice site by ~3-fold as compared to the control (FIG. 10C). These results indicate that theophylline-RNA interaction can influence 3' splice site switch.

Figure 32:
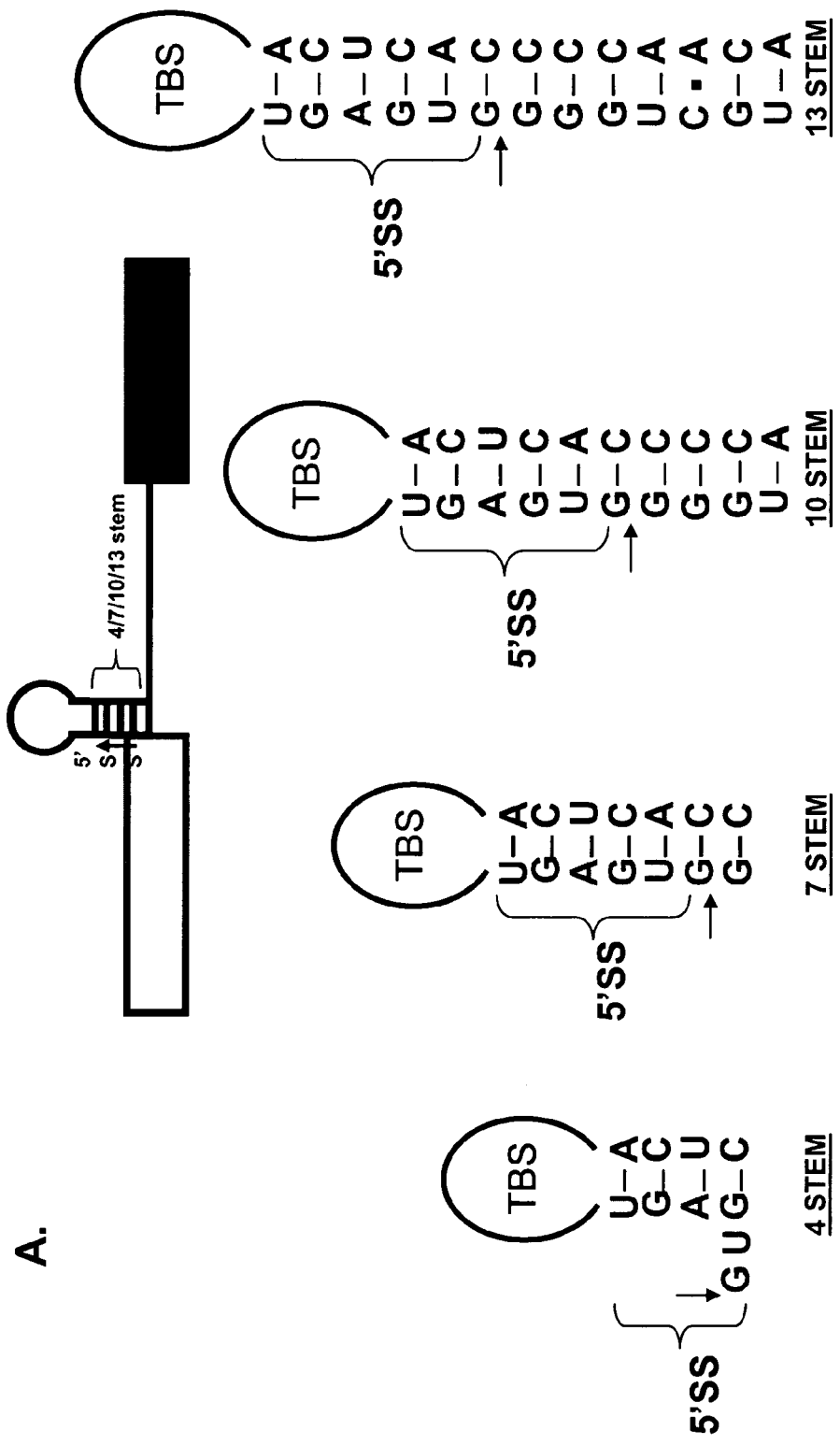
FIG. 32. Theophylline inhibits pre-mRNA splicing of a substrate whose 5' splice site (ss) is embedded within the theophylline binding aptamer. (A), Construction of theophylline responsive pre-mRNA substrates. The pre-mRNAs were generated by in vitro run-off transcription using BamHI digested plasmids. (B), $^{32}$P-labeled AdMLTheo54Mut (4 nucleotide lower aptamer), AdMLTheo57Mut (7 nucleotide lower aptamer), AdMLTheo510Mut (10 nucleotide lower aptamer), and AdMLTheo513Mut (13 nucleotide lower aptamer) pre-mRNAs were subjected to in vitro splicing in the absence or presence of theophylline by incubating in HeLa nuclear extract. (C), Quantification of data from (B). Splicing efficiency was calculated and normalized as the ratio of spliced mRNA to pre-mRNA.
Figure 33:
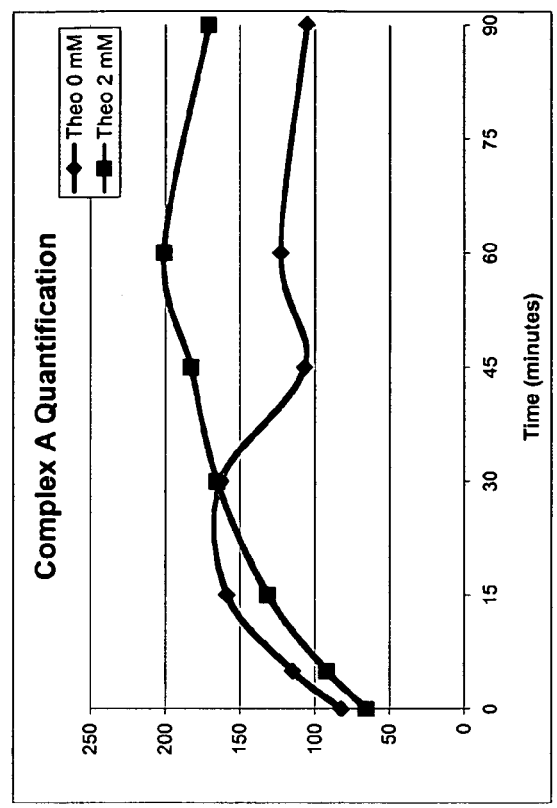
FIG. 33. Theophylline inhibits pre-mRNA splicing by blocking spliceosome assembly. (A), $^{32}$P-labeled AdMLTheo510Mut was subjected to a spliceosome assembly assay in the absence or presence of 2 mM theophylline. Bands representing splicing complex H, A, and B/C are marked on the left. (B), Effect of theophylline on the relative intensity of splicing complex A formation of AdMLTheo510Mut.
Figure 33:
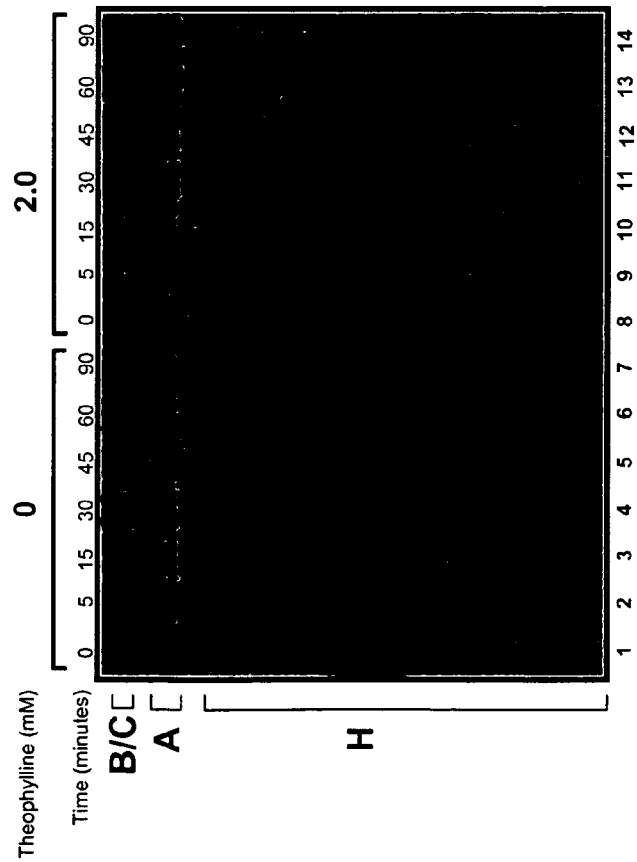
Figure 34:
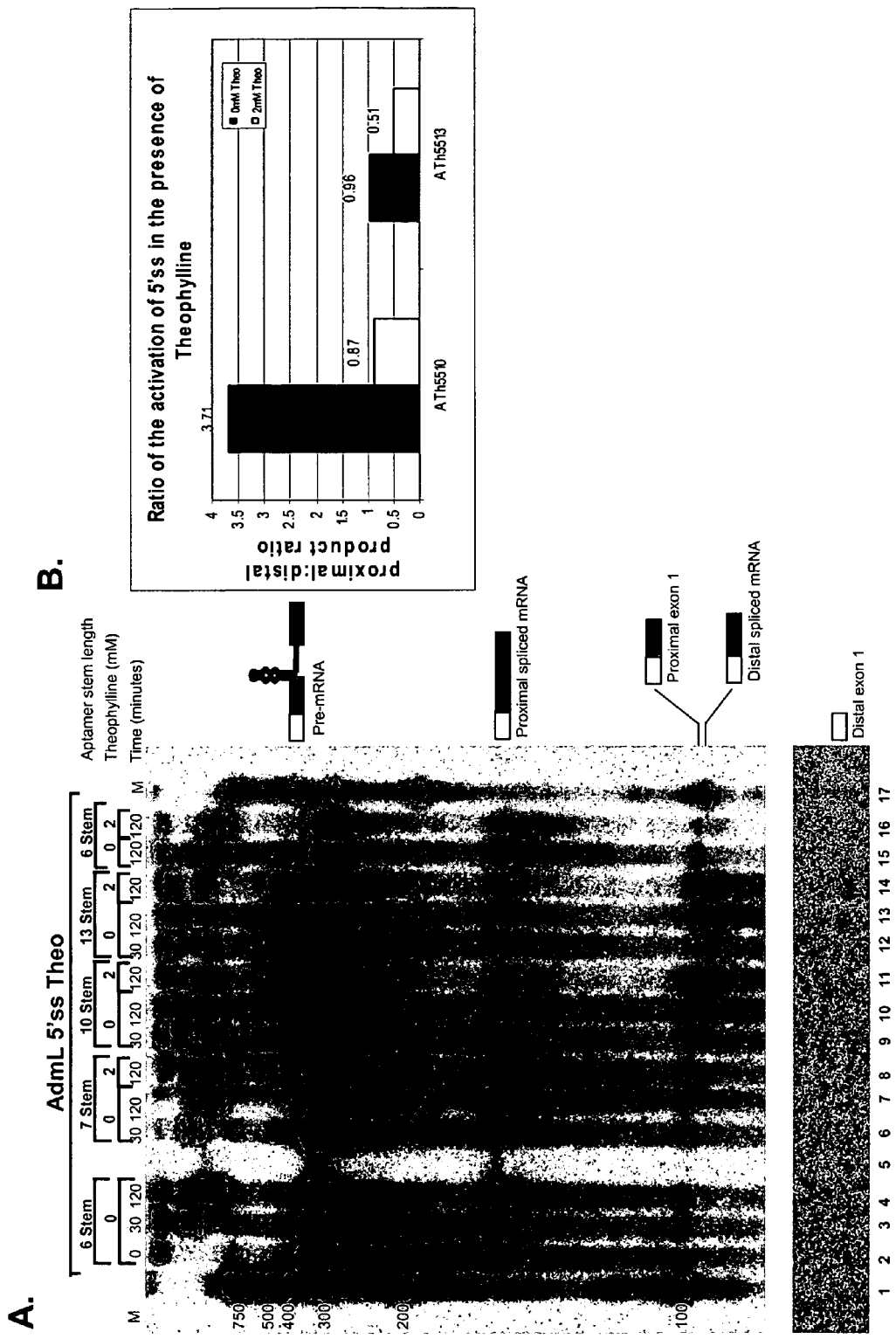
FIG. 34. Theophylline-mediated sequestering of 5' ss can promote alternative splicing. (A), $^{32}$P-labeled AdML Theo 5' ss was subjected to in vitro splicing in the absence or presence of 2 mM theophylline. (B), Effect of theophylline on activation of distal 5' ss using AdMLTheo510 and AdML513 substrates at 120 minutes.
Figure 35:
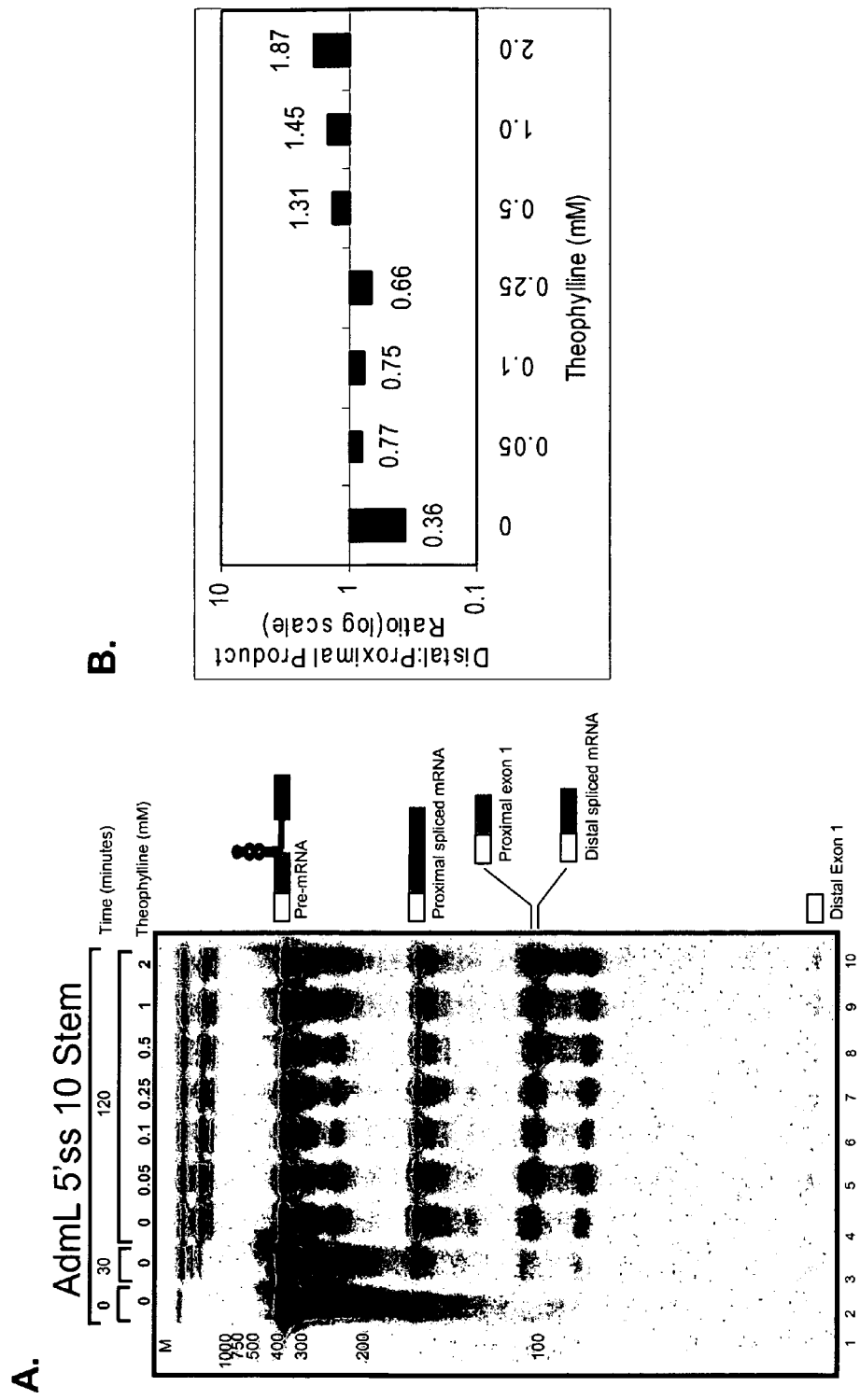
FIG. 35. Theophylline can induce alternative splicing in a dose-dependent manner. (A), $^{32}$P-labeled AdML Theo 5' ss with 10 nucleotide stem was subjected to in vitro splicing in the presence of varying concentrations of theophylline. (B), Effect of theophylline on the activation of distal 5' ss AdM-LTheo510 splicing at 120 minutes.

Similar experiments were run using pre-mRNA substrates wherein the 5' ss rather than the 3' ss was embedded within the theophylline binding aptamer. Plasmids encoding three 5' ss embedded AdML pre-mRNA derivatives (AdMLTheo54Mut, AdMLTheo57Mut, AdMLTheo510Mut, and AdMLTheo513Mut) were constructed using a standard PCR based approach (FIG. 32A). The length of the lower aptamer stem in these substrates varied from 4 to 13 nucleotides. To prevent the activation of a cryptic 5' ss, the GU's (potential 5' ss) upstream of the authentic 5' ss were mutated to GC. In a splicing assay, theophylline was found to inhibit splicing of each of these 5' ss embedded substrates (FIGS. 32B and C). The proximal to distal product ratio decreased in the presence of theophylline in the 10- and 13-nucleotide lower aptamer substrates (FIGS. 34A and B). Theophylline induced alternative splicing in a dose-dependent manner (FIGS. 35A and B). In a subsequent spliceosome assembly assay, theophylline was found to inhibit spliceosome assembly (FIGS. 33A and B).

Controlling gene expression in living cells through theophylline-RNA interaction. In the in vitro splicing assay, theophylline-RNA interaction has been shown to regulate pre-mRNA splicing. To determine if such an approach could also regulate gene expression in living cells, a splicing reporter was constructed in which the cDNA of AdML-Theo29AG pre-mRNA was inserted into the 5' UTR of green fluorescence protein (GFP) cDNA. It was contemplated that theophylline mediated inhibition of AdML-Theo29AG splicing will prevent the export of GFP mRNA which will be mirrored by the lack of GFP expression. The reporter plasmid was constructed by standard molecular cloning approach. In brief, a PCR amplified DNA fragment containing the entire AdML-Theo29AG sequence was cloned into the EcoRI/Sal I digested expression vector (pEGFP-N1, Invitrogen). The resulting reporter plasmid, pAdML-Theo29AG-EGFP, contains the cDNA of AdML-Theo29AG pre-mRNA fused 5' to the GFP coding sequence.

Figure 11:
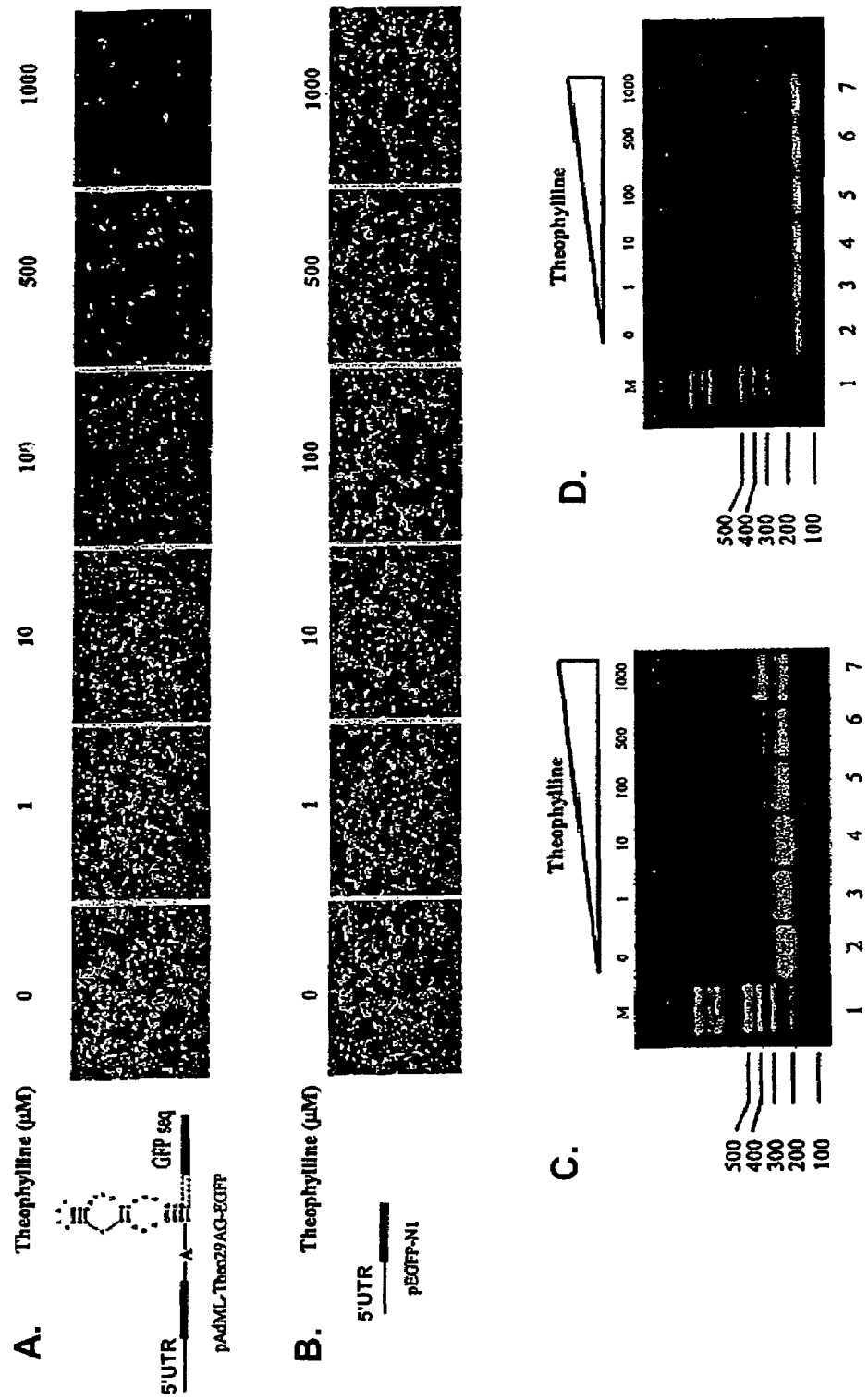
FIG. 11. Theophylline-mediated regulation of pre-mRNA in living cells.

To examine theophylline-mediated regulation of AdML-Theo29AG splicing, HEK293 cells were transfected with pAdML-Theo29AG-EGFP reporter using polyfectin following manufacturer's instructions (Qiagen). Cells were grown and maintained in a humidified atmosphere at 37° C. under 5% CO2 in Dulbecco's Modified Eagle Medium (Cellgro) supplemented with 10% fetal bovine serum and antibiotics (100 µg/ml streptomycin and 100 U/ml penicillin). For transfection, cells ($3\times10^4$, per well) were seeded in a 24 well plate and incubated for 24 h (50-80% confluency) at which time pAdML-Theo29AG-EGFP or pEGFP-N1 was introduced. After 10 hours of incubation, cells were treated with buffer or theophylline (0 to 1M) and incubation was continued up to 48 hours. The GFP expression was visualized with a fluorescence microscope and cells were photographed with color CCD camera (Olympus). We observed that the cells, which were transfected with pAdML-Theo29AG-EGFP and treated with theophylline showed a dose dependent decrease in GFP expression (FIG. 11A). In contrast, theophylline treatment had virtually no effect on levels of GFP expression of cells that were transfected with the control plasmid, pEGFP-N1 (FIG. 11B).

An RT-PCR assay was performed to confirm that theophylline-mediated reduction of GFP expression is due to the inhibition of AdML-Theo29AG-EGFP splicing and not the result of mRNA degradation. Total RNA was isolated (from $3\times10^4$ cells) using trizol reagent. In a total volume of 20 µl, 5 µg of total RNA was reverse transcribed (RT) using vector specific reverse primer (GFPR, 5'-GTCGCCGTCCAGCTCGAC-CAGG-3') according to manufacturer's instructions (Invitrogen Kit). Next, an aliquot (2 µl) of RT product was subjected to PCR amplification in a 50 µl reaction using 2.5 units of Taq polymerase, vector specific forward (GFPF, 5'-GCGCTAC-CGGACTCAGATCTCG-3') and reverse primer (GFPR, 5'-GTCGCCGTCCAGCTCGACCAGG-3'). The amplified product was analyzed on a 2% agarose gel. As shown in FIG. 11C, theophylline repressed the splicing of AdML-Theo29AG-EGFP pre-mRNA. Unlike the untreated control, which generated ~250 bp fragment, theophylline treated cell yielded a PCR product corresponding to the size of unspliced RNA (~350-bp). Significantly, there is a direct correlation between the intron retention and the concentration of theophylline (FIG. 11C, cf lanes 2-7). Notably, the RT-PCR of RNA from the cells transfected with control vector yielded a smaller DNA fragment (FIG. 11D, this vector did not contain AdML-TheoAG29 pre-mRNA). These results indicate that theophylline-RNA interaction can regulate the splicing of a target gene both in vitro as well as in vivo.

As mentioned above, another aspect of the present invention relates to the optimization of the BPS-to-3' splice (AG) distance. It has been reported that the preferred distance for an AG to serve as the site for second transesterification step has been proposed to be 19 to 23 nucleotides downstream from the BPS (Chua and Reed, 2001). Thus, preferred pre-mRNA for theophylline-dependent splicing includes the one in which BPS-to-AG distance is 19 to 23 nucleotides and AG is located within the theophylline binding pocket. The sequences subject to the optimization include:

1) ACUUUUUUUCCUCAUACCAGCCGAAAGGCCCU-UGGCAG (SEQ ID NO: 11);

2) ACUUUUUUUUCCUCAUACCAGCCGAAAGGCCC-UUGGCAG (SEQ ID NO: 12);

3) ACUUUUUUUUUCCUCAUACCAGCCGAAAGGCC-CUUGGCAG (SEQ ID NO: 13);

4) ACUUUUUUUUUUCCUCAUACCAGCCGAAAGGC-CCUUGGCAG (SEQ ID NO: 14); and

5) ACUUUUUUUUUUUCCUCAUACCAGCCGAAAG-GCCCUUGGCAG (SEQ ID NO: 15).

To test this, a series of pre-mRNAs will be synthesized in which the BPS-to-AG distance will be varied from 19 to 23 nt. Plasmids encoding these pre-mRNAs (FIG. 12, AdML-Theo19, 21 and 23-AG) will be constructed by inserting oligonucleotides into the Hind III and Sal I sites of pAdML-Theo29AG to replace the sequences from the BPS to the entire theophylline-binding sequence. Linearized plasmids will be used to transcribe pre-mRNAs. Next, $^{32}$P-labeled pre-mRNAs (~10 fmol) will be subjected to in vitro splicing in the absence or presence of theophylline as described in FIG. 3. The pre-mRNA, which in the absence of theophylline completes both steps of the splicing with normal kinetics, and whose splicing is specifically inhibited by the addition of theophylline will be used in future experiments.

Another aspect of the present invention relates to the modification of theophylline-dependent aptamers to improve their affinity for theophylline, preferably in physiological relevant concentration of divalent metal ions (e.g., $Mg^{2+}$). As described above, theophylline achieves partial modulation of RNA splicing (FIG. 3). This could most likely be due to the differential metal ion requirements for the binding of theophylline to its cognate RNA and in vitro splicing reaction. While 5.0 mM $Mg^{2+}$ (Jenison et al., 1994; Zimmermann et al., 2000) has been reported to be optimum for the high affinity RNA binding of theophylline, ~3.0 mM $Mg^{2+}$ has been found to be optimum for in vitro splicing (Krainer et al., 1984). Although the observed ~70% repression of splicing is sufficient to influence splice site switch, in many cases a complete repression may be desirable. Moreover, it would be even preferable, especially for in vivo applications, if this could be achieved by using physiological relevant concentrations of $Mg^{2+}$ (e.g., ~3.0 mM).

To achieve high affinity theophylline-aptamer binding at physiological $Mg^{2+}$ concentrations, the RNA affinity of theophylline will be increased by introducing modifications in the existing aptamer. A large body of evidence suggests that modified nucleotides stabilize RNA structures by affecting thermodynamic and kinetic parameters (Bevers et al., 1999; Proctor et al., 2004). As a parallel approach, we will employ in vitro selection to screen new aptamers that may bind to theophylline with high affinity and specificity at ~3.0 mM $Mg^{2+}$.

Figure 13:
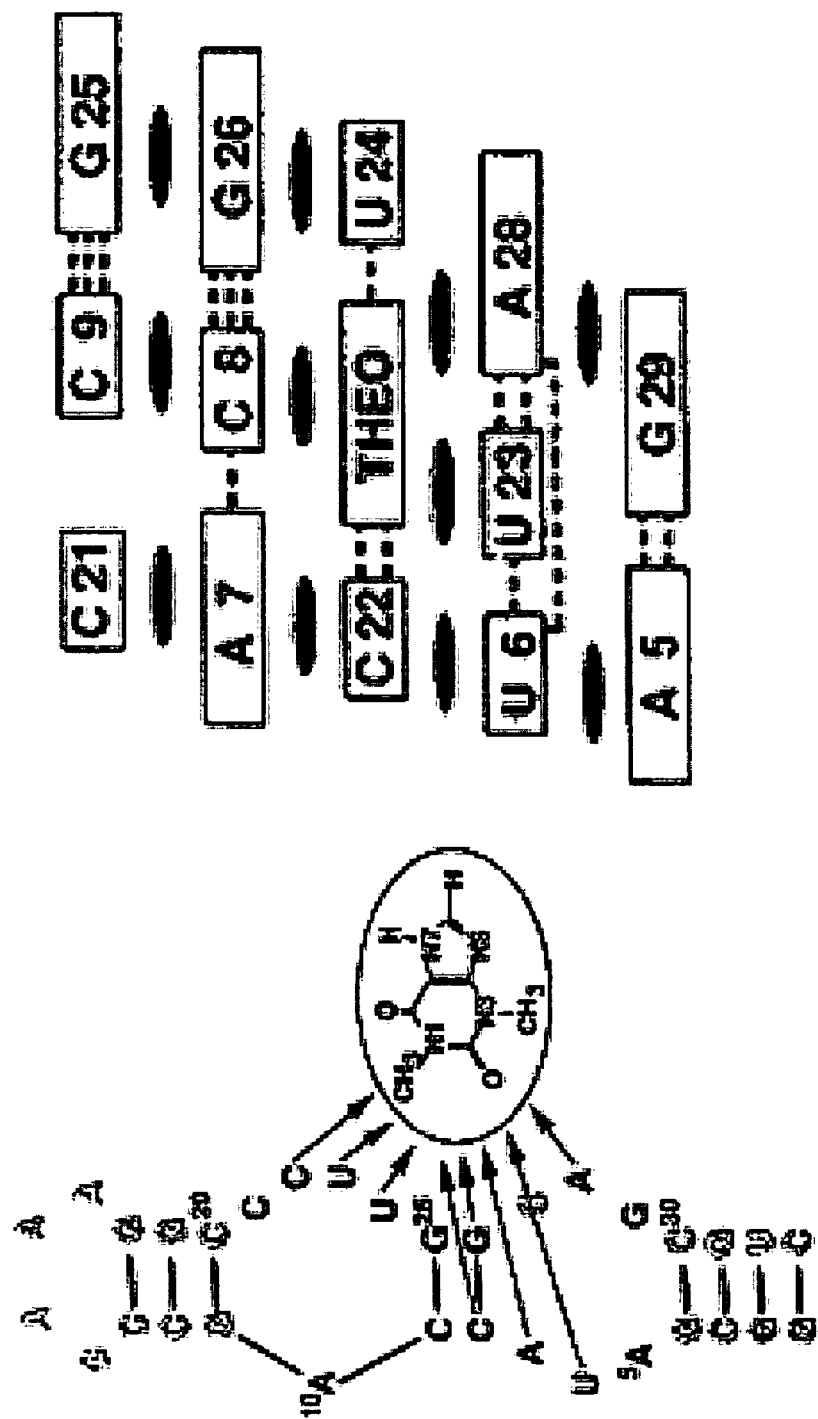
FIG. 13. Sequence and secondary structure of theophylline-binding RNA (SEQ ID NO: 16). Right panel shows the schematic representation of the base triples and stacking interactions in the core of the RNA-theophylline complex. Dashes lines: hydrogen bonds; ovals: stacking interactions. (See also Zimmermann et al., Nat. Struct. Biol. 4, 644-649 (1999)).
Figure 14:
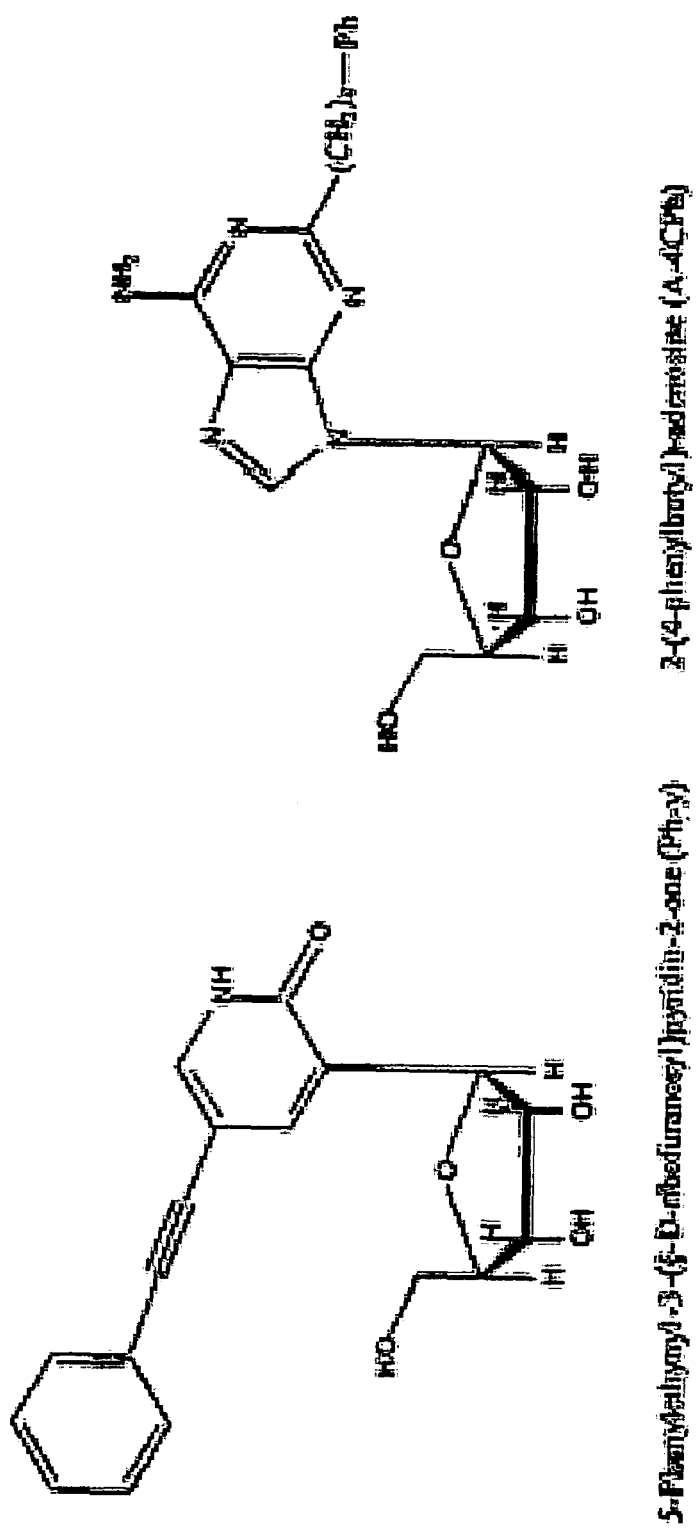
FIG. 14. Structure of proposed modified nucleotides.

The NMR structure of theophylline-aptamer complex indicates that a number of stacking interactions make important contribution towards stabilization of the RNA-theophylline complex (Zimmermann et al., 1997). For example, a "base-zipper" which forms one side of the binding pocket and consists of residues U6, C22, A7, and C21 plays an important role in the stabilization of theophylline-RNA complex (FIG. 13). Likewise, on the other side of the core, G26 intercalates between the bases U24 and G25 (FIG. 13). Additional interactions between A5 and U6, and A28 and G29 have been proposed to stabilize this complex (FIG. 13). This model predicts that an increase in the hydrophobicity of U6, U23 or U24 residues should increase the stability of theophylline-RNA complex. Indeed, replacement of U24 by an unnatural base, 5-phenylethynyl-3-(β-D-ribofuranosyl)pyridin-2-one (Ph-y) (FIG. 14) has been shown to significantly improve the stability of theophylline aptamer (Endo et al., 2004). Likewise, an adenosine analog, 2-(4-phenylbutyl)-adenosine (A-4cPh) in which a phenyl group is linked to the adenine base has been shown to increase the affinity of a mutant U1A protein for U1 snRNA (FIG. 14) (Zhao and Baranger, 2003). Thus, it is conceivable that insertion of these modifications into the theophylline aptamer may improve its affinity for theophylline.

Figure 12:
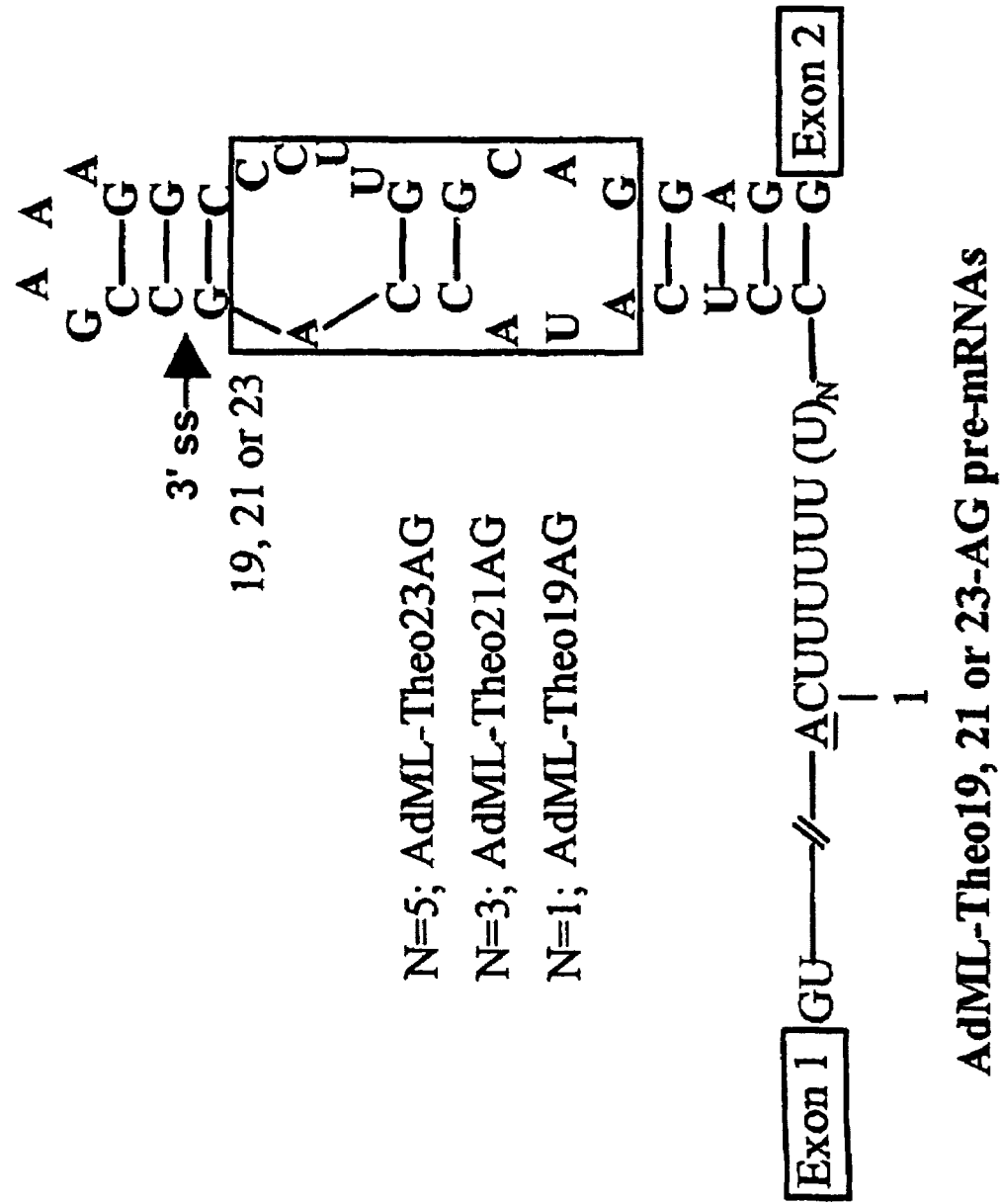
FIG. 12. AdML-Theo19 (SEQ ID NO: 22), AdML-Theo21 (SEQ ID NO: 23), and AdML-Theo23 (SEQ ID NO: 24) pre-mRNAs.

In addition, one embodiment of the invention relates to a systematic analysis of the effect of these modified nucleotides on the RNA affinity of theophylline. For example, a series of theophylline aptamers bearing the substitution of Ph-y for U6, U23 or U24 will be synthesized by in vitro transcription following the published protocol (Endo et al., 2004). Because Ph-y can be incorporated into the RNA only if the template contains an unnatural base (2-amino-6-(2-thienyl) purine) opposite the site of Ph-y incorporation, T7 transcription templates containing 2-amino-6-(2-thienyl) purine at predetermined site will be synthesized as described in the literature (Endo et al., 2004). The aptamers with A-4cPh modification at position A5, A7, A10 or A28 will be synthesized following standard RNA synthesis protocol by substituting A4cPh phosphoramidite for adenosine phosphoramidite (Zhao and Baranger, 2003). Since the phenyl groups in Ph-y and A4cPh do not occupy the positions, which have been proposed to be involved in the base-triple interactions (Zimmermann et al., 1997), these modifications may not interfere in the binding of theophylline. Once the RNA aptamers with the desired modifications are synthesized, our next goal will be to determine the binding affinity of theophylline for modified aptamers. We will use equilibrium filtration technique to estimate RNA affinity of theophylline (Jenison et al., 1994). Among the sets of Ph-y and A-4cPh modified aptamers that provide tight binding (better than the wild type aptamer) will be subjected to double substitution to determine if a further increase in the binding affinity can be achieved. In other words, if determined that from the sets of Ph-y and A4cPh modified aptamers U23 and A7 modifications, respectively resulted into improved binding of theophylline, then an aptamer bearing both U23 and A7 modifications will be synthesized and tested for its ability to bind theophylline. The aptamer with highest binding affinity will be used to construct AdML derivative following Moore and Sharp approach (Moore and Sharp, 1992). First, we will construct pre-mRNAs as shown in FIG. 12. However, if they turn out to be less effective, then we will substitute the modified aptamer for the aptamer in AdML-Theo29AG. Finally, the splicing of the assembled pre-mRNAs will be examined in the absence or with increasing concentrations of theophylline. If found that theophylline can achieve a complete or improved inhibition of the splicing, that would suggest that the preexisting RNA structural information can be used to increase the binding affinity of theophylline.

Figure 15:
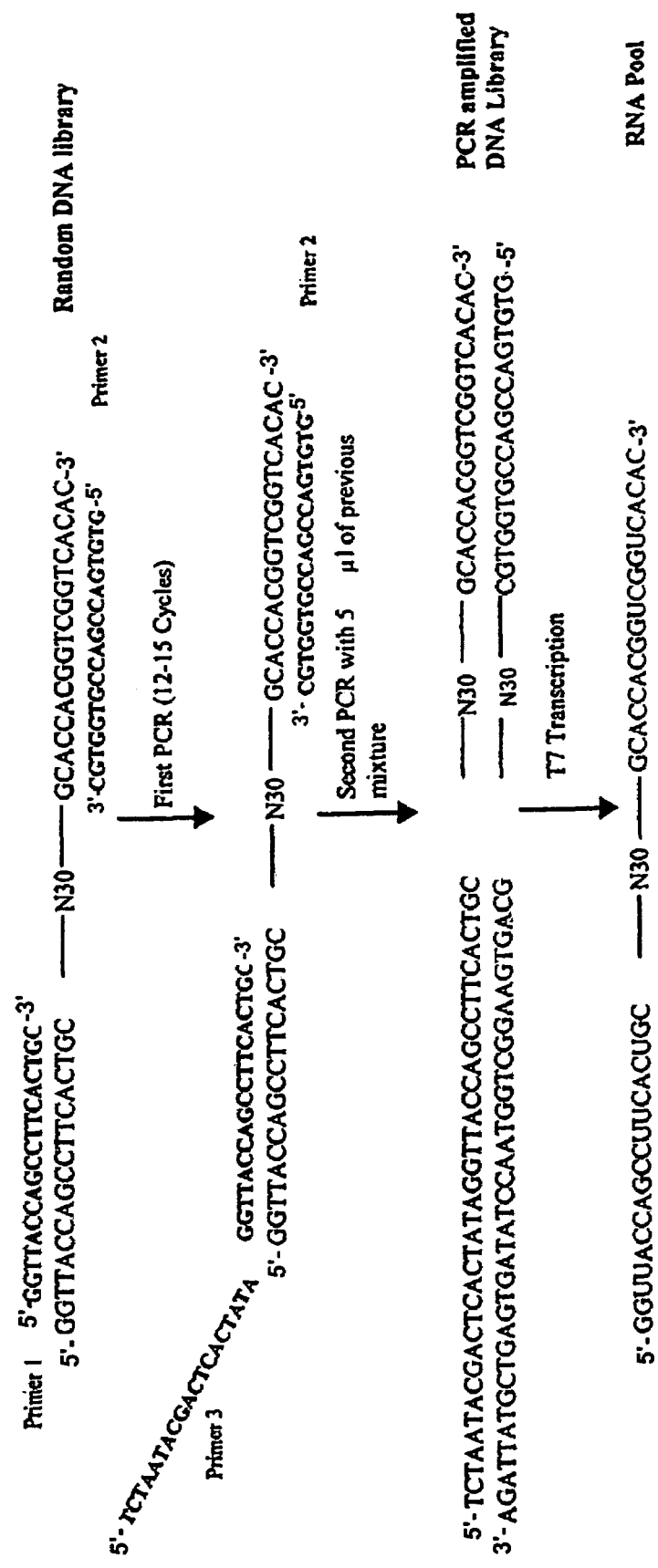
FIG. 15. Schematic representation of the steps in the in vitro selection of anti-theophylline aptamer.

Another embodiment of present invention relates to methods of designing/screening/isolating aptamers that bind to theophylline at physiological $Mg^{2+}$ concentration. It has been reported that in vitro selection can be used to isolate RNA aptamers, which can specifically bind to a trans-activation-responsive (TAR) RNA at physiological magnesium condition (3.0 mM) (Duconge and Toulme, 1999). If an anti-TAR aptamer could bind to a polyanionic target with high affinity (Kd ~30 nM) and specificity, it is conceivable that SELEX (Joyce, 1994) might also evolve an aptamer that would bind to theophylline with high affinity at physiological $Mg^{2+}$ concentration. The isolation of aptamers will be carried out according to the published protocol (Jenison et al., 1994) except that selection will be performed in the buffer containing 3.0 mM $Mg^{2+}$. Briefly, the RNA populations (pool of ~$10^{12}$ molecules) will be generated by in vitro transcription from a DNA template containing a random cassette of 30 nucleotides (FIG. 15). Because the coupling efficiency of dG and dT monomers is higher than dA and dC, a pre-made mixture of dA:dG:dC:dT, 1.5:1.15:1.25:1 will be used for the synthesis of random pool. This will prevent the overrepresentation of dG and dT in the random DNA library (Huang and Szostak, 2003; Marshall and Ellington, 2000).

Prior to in vitro selection, 12-15 cycles of PCR will be performed with ~0.2-0.4 µmol of gel purified DNA library with forward (primer 1, SEQ ID NO: 37) and reverse (primer 2, SEQ ID NO: 38) primers which will bind to the constant segments (FIG. 15). The initial DNA pool will be subjected to the second PCR amplification with the forward primer containing the T7 promoter sequence (primer 3, SEQ ID NO: 39) and the same reverse primer used in the previous PCR. RNAs will be generated by in vitro transcription using PCR amplified library and T7 RNA polymerase. Before the actual selection, the starting pool will be heat denatured to disrupt potentially higher order structures. Next, the RNA pool will be allowed to pass through the underivatized Sepharose column followed by the column containing theophylline-linked Sepharose, which will be prepared following published report (Jenison et al., 1994). The bound RNAs will be eluted by theophylline and then converted to cDNAs for further amplification by PCR. To increase the stringency of the selection process, "counter SELEX" step will be included: after washing, bound RNAs will first be eluted with 0.1 M caffeine. Unlike previously reported protocol, where 0.1 M theophylline was used for elution (Jenison et al., 1994), buffers with step-wise increase of theophylline concentration will be used. Initially, we will start with buffers containing 10-20 µM theophylline. The rational for using low concentrations of theophylline is to isolate only those RNA molecules that bind to theophylline with extremely high-affinity. If 10-20 µM theophylline failed to elute detectable amounts of RNAs, elution buffer containing increasing concentrations of theophylline (a step-wise increase) will be used. Each RNA population isolated from increasing concentrations of theophylline will be subjected to reverse transcription and PCR amplification separately. After 8-10 rounds of selection, the double-strand complementary DNA populations derived from each set will be cloned and sequenced. Finally the binding affinity of each class of aptamers will be estimated (Jenison et al., 1994).

Once a class of high affinity theophylline aptamer is identified, we will determine the minimal sequence that may be sufficient for the binding of theophylline. To this end, sequence/motif that is common among the candidate aptamers will be identified, and mfold program will be used to generate the secondary structure (Zuker, 1989). With this information in hand, aptamers bearing the deletion of non-consensus sequences will be synthesized and evaluated for their affinity for theophylline. The aptamer(s) that bind to theophylline with high affinity (preferably in low nM range) at physiological $Mg^{2+}$ will be used to generate AdML derivatives essentially as described above. The new anti-theophylline aptamer will not only be of direct use in the proposed studies, but also be of general interest for generating theophylline dependent allosteric ribozymes and in the construction of highly sensitive biosensor for monitoring theophylline in biological samples.

Another aspect of the present invention relates to method of developing theophylline-dependent bifunctional molecules which can regulate pre-mRNA splicing. It has been demonstrated that a system based on theophylline-RNA aptamer binding could be manipulated to regulate pre-mRNA splicing. However, such an approach may not be applicable for reprogramming the splicing of an endogenous gene. With the aim of developing a versatile approach, which not only modulates pre-mRNA splicing like an antisense RNA, but also has the mechanism to switch on/off the binding of antisense RNA, it is contemplated that if an antisense oligonucleotide directed to bind an exonic splicing enhancer (ESE) were part of theophylline aptamer then the resulting bifunctional molecule would be modular in nature: The binding of antisense domain to the ESE will repress the splicing of targeted pre-mRNA, whereas the addition of theophylline to the splicing reaction will induce a conformational rearrangement which will displace antisense RNA from its target. Thus, the bifunctional molecule will function like an allosteric enzyme whose activity can be controlled by an effector.

Figure 16:
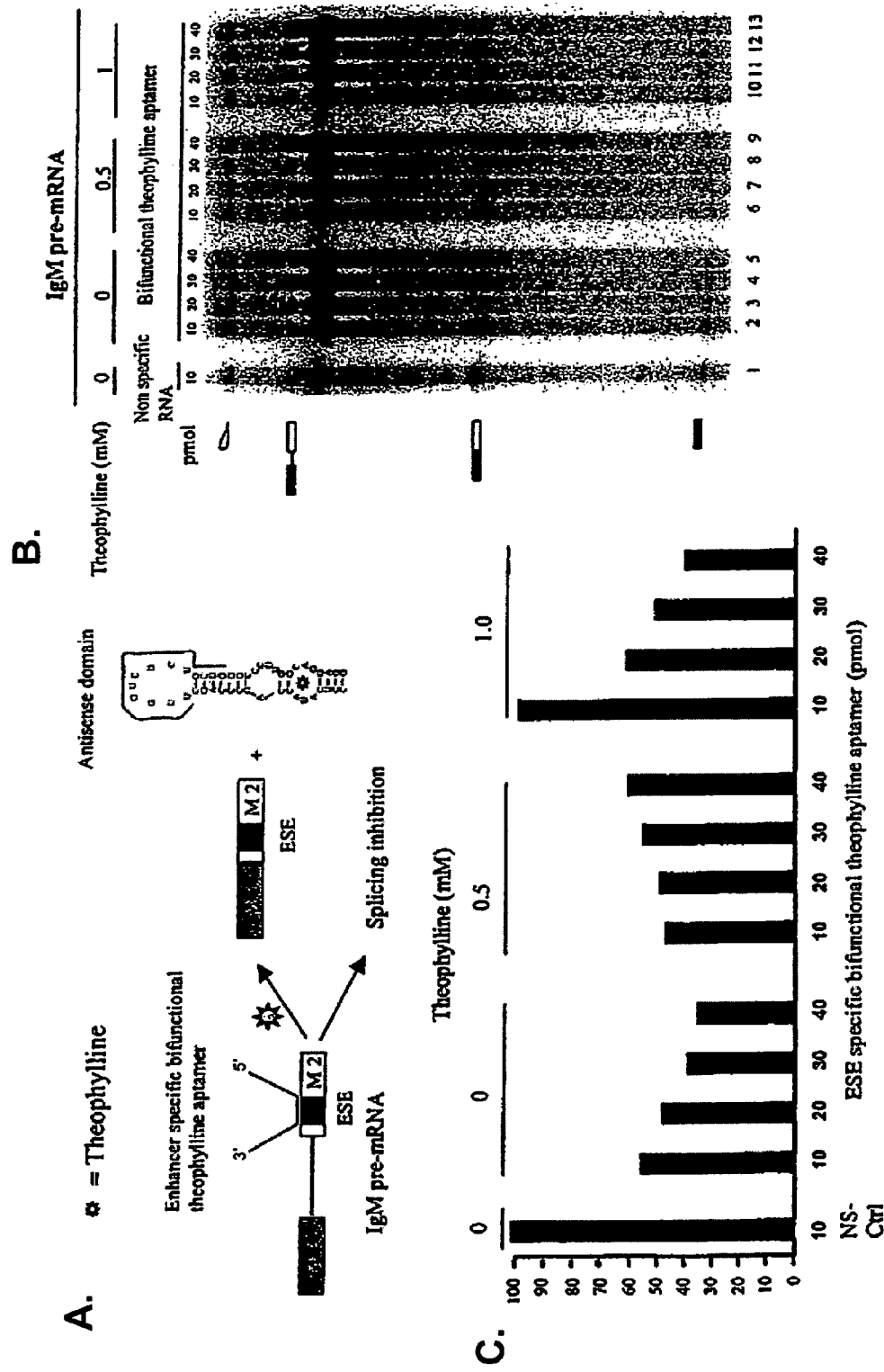
FIG. 16. Bifunctional theophylline aptamer can regulate pre-mRNA splicing in the theophylline-dependent manner. (A) Model explaining the hypothesis. (B) in vitro splicing of IgM pre-mRNA. (C) Histogram qualifying the data in (B). NS control indicates non-specific control. An asterisk (*) indicates that similar size bands were also reported by Graveley et al., RNA 7, 806-18 (2001).

To test this, we designed a bifunctional theophylline aptamer in which the non-conserved portion of the aptamer is complementary to the ESE present in the alternative exon M2 of the mouse IgM gene (FIG. 16). The IgM pre-mRNA is a well-characterized substrate and its ESE is essential for the splicing of the preceding intron between exon M1 and M2 (Tanaka et al., 1994; Watakabe et al., 1993). To prevent non-specific binding, $^{32}$P-labeled IgM pre-mRNA and bifunctional aptamer were denatured for 1 minute at 90° C. followed by incubation for 10 min at 30° C. Next, the splicing mixture with or without theophylline was added, and reaction mixture incubated at 30° C. for 2 hours. After which the products of the splicing reaction were separated on a 13% denaturing polyacrylamide gel. FIG. 16 shows that in contrast to a non-specific control (lane 1), the addition of 10 pmole of enhancer specific bifunctional aptamer was able to inhibit the splicing by ~50%. However, addition of theophylline and bifunctional aptamer together resulted in restoration of splicing (FIG. 16, compare lanes 2 and 10, and histogram in panel C), suggesting that a theophylline induced conformation change has displaced the bifunctional aptamer from the enhancer.

It is noted that the bifunctional aptamer did not elicit a complete inhibition of splicing. Although increasing the concentration of bifunctional aptamer did improve splicing repression (FIG. 16, lane 2-5), but the efficiency of theophylline-mediated restoration of splicing was also compromised, suggesting that excess bifunctional aptamer likely titrated out theophylline. The observed incomplete repression of splicing might also be the result of nucleases-assisted degradation of bifunctional aptamer. Incubation of $^{32}$P-labeled bifunctional aptamer in HeLa nuclear extract confirmed that significant portion of the RNA is degraded (not shown). We also observed that theophylline-mediated reversal of splicing repression is impressive, but requires 1.0 mM theophylline. A possible explanation to this observation could be that the free energy of theophylline-aptamer binding may be insufficient to disrupt the Watson-Crick base-paring interactions between the antisense domain and ESE. High affinity binding of theophylline to its aptamer requires 5.0 mM $Mg^{2+}$ (Jenison et al., 1994), and under in vitro splicing conditions at ~3.0 mM $Mg^{2+}$ apparently weak interaction between theophylline and aptamer might have resulted into incomplete reversal of splicing inhibition. This may also be true for incomplete inhibition of AdML-Theo29AG splicing (FIG. 3).

Another aspect of the present invention relates to methods of improving the stability of bifunctional theophylline aptamer against nucleases. The high affinity theophylline aptamer identified will serve as the starting molecule to generate nuclease resistant bifunctional aptamer. A number of chemical modifications have been shown to increase the stability of both DNA and RNA against nucleases (Kurreck, 2003). Modifications that have been shown to improve the stability of antisense RNAs will be tested to identify those that show maximum serum stability without compromising with the affinity for theophylline.

For example, a bifunctional aptamer may be modified to improve stability by using phosphorothioate. One of the most important chemical modifications that have been widely used in classical antisense approach is the replacement of the phosphodiester backbone with phosphorothioate (PS) linkage (Kurreck, 2003; Vortler and Eckstein, 2000). Excellent water solubility, reduced cleavage by nuclease, relative ease of synthesis, and improved bioavailability of P-S modified oligonucleotides make them an attractive tool for antisense research. The phosphorothioate substituted bifunctional aptamer will be synthesized by standard in vitro transcription except that NTPs will be replaced by NTPaS. The resulting bifunctional aptamer will be tested for nuclease sensitivity by incubating in HeLa nuclear extract. Splicing assay will be performed with IgM pre-mRNA.

Another example of improving the stability of a bifunctional aptamer is to use 2'-modified nucleotides. The presence of 2' hydroxyl group in RNA makes it more susceptible to cleavage by nucleases (Eder et al., 1991; Shaw et al., 1991; Tsuji et al., 1992). Interestingly, modifications such as 2'-O-methyl (Monia et al., 1993), 2'-deoxy-2'-fluoropyrimidines (Kawasaki et al., 1993) and 2'-O-methoxyethyl (2'-OMOE) (Chen et al., 2002) have been shown to increase the stability of RNA. Among them, 2'-deoxy-2'-fluoropyrimidine has gained considerable attention. Compared to unmodified RNAs, 2'-fluoro, 2'-deoxy-substituted RNAs are significantly more stable ($10^3$-$10^5$-fold), and therefore more commonly used for the preparation of aptamers, ribozymes and antisense molecules for therapeutic application (Heidenreich et al., 1994; Kubik M F, 1997; Pieken et al., 1991). In addition to having resistance to nucleases, 2'-deoxy, 2'-fluoronucleosides prefer to adopt C3'-endo conformation, as in the case of ribonucleosides (Aurup et al., 1992; Guschlbauer, 1980). Furthermore, the commercial availability of 2'-deoxy, 2'-fluoronucleosides both as a 5' triphosphate and phosphoramidite, allow the synthesis of 2'-fluoro substituted RNAs by chemical and enzymatic methods.

Pardi and coworkers (Zimmermann et al., 2000) have shown that all but one 2' hydroxyl group (U24) of theophylline binding aptamer can be converted to the 2'-deoxy without having a noticeable effect on its affinity for theophylline. Thus, it is reasonable to assume that replacement of uridines (except U24) by 2'-deoxy, 2'-fluorouridine may not have any negative effect on RNA affinity of theophylline. Bifunctional aptamer will be synthesized in which the 2'-deoxy-2,-fluorouridine will be substituted for uridine (except U24), and the four terminal phosphodiester linkages will be replaced by P-S group; a report published by Eckstein and coworkers suggests that such a combination significantly improves the stability of hammerhead ribozymes (Heidenreich et al., 1994).

Another aspect of the present invention relates to a novel bimolecular allosteric hammerhead molecule, which should be able to regulate pre-mRNA splicing in theophylline-dependent manner. In other words, theophylline-dependent bimolecular hammerhead ribozymes may be engineered to regulate pre-mRNA splicing. It has been demonstrated that hammerhead ribozyme can be made to induce or suppress RNA cleavage in theophylline-dependent fashion by appending theophylline aptamer to a non-essential stem region (Soukup and Breaker, 1999a; Soukup and Breaker, 1999b; Soukup et al., 2000). It has also been shown that both hammerhead ribozyme (Kuwabara et al., 1998; Kuznetsova et al., 2004) and theophylline aptamer (Zimmermann et al., 1998; Zimmermann et al., 2000) could be assembled into their native conformations by using two RNA oligonucleotides. These properties of theophylline aptamer and hammerhead ribozyme will be exploited to generate an effector dependent hammerhead ribozyme, which will regulate the splicing of a target pre-mRNA without cleaving the pre-mRNA.

Figure 17:
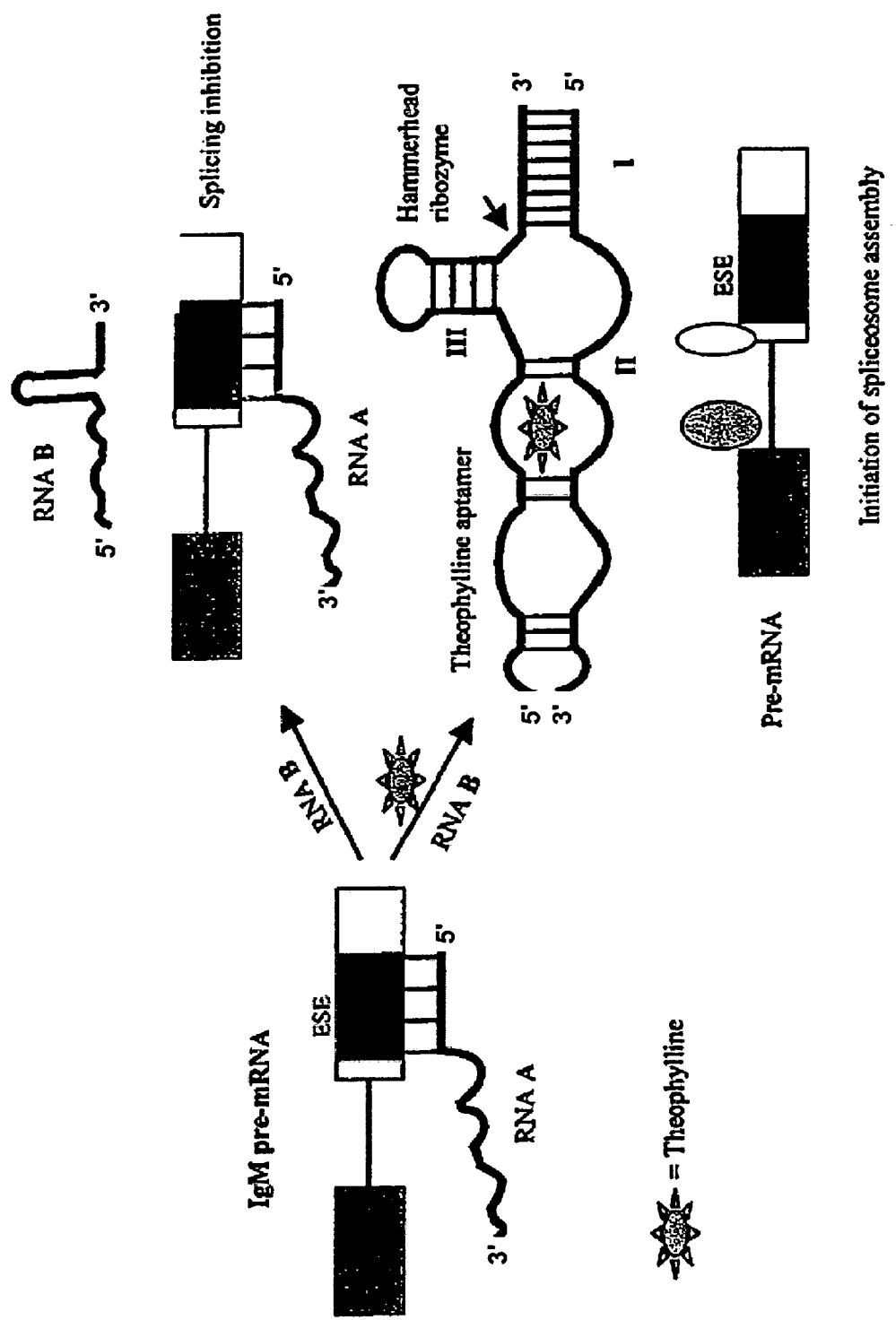
FIG. 17. Model describing bifunctional hammerhead ribozyme based regulation of pre-mRNA splicing.

The theophylline-dependent bimolecular hammerhead ribozyme approach is outlined in FIG. 17. RNA A is the lower half of the theophylline-dependent hammerhead ribozyme in which the 5' portion of stem I is complementary to ESE. The IgM pre-mRNA and RNA A will be incubated in nuclear extract under splicing conditions. This will repress the splicing of IgM pre-mRNA. This assumption is supported by the data presented in FIG. 16. The addition of both RNA B and theophylline, but not individually, to the splicing reaction will lead to the assembly of the active hammerhead ribozyme, and restoration of splicing. Since the assembly of the active ribozyme has been reported to be dependent on the presence of theophylline (Soukup and Breaker, 1999a; Soukup et al., 2000), the addition of either RNA B or theophylline to the splicing reaction may not revert inhibition. The prerequisite for theophylline-dependent assembly of hammerhead ribozyme is the disruption of RNA A-ESE duplex, and an extended duplex might prove to be problematic. Thus, initial experiments will be aimed at optimization of the length of the antisense domain of RNA A. The ideal antisense domain should be long enough to achieve repression, but be displaced in the presence of theophylline and RNA B. We will start with 8 nucleotides, which was originally employed to generate theophylline dependent allosteric ribozyme (Soukup and Breaker, 1999a). If determined that 8 nucleotides failed to provide splicing repression, we will increase the length to 10, 12 and 15 nucleotides.

To test the utility of the proposed approach, the splicing of IgM pre-mRNA will be examined. $^{32}$P-labeled pre-mRNA and RNA A will be annealed. After 15-20 minutes, theophylline, RNA B, HeLa nuclear extract and other components of the splicing mix will be added followed by incubation at 30° C. for 2 hours. Control reactions without RNA B or theophylline will also be performed. Although ~200 µM theophylline has been reported to be optimum for the assembly of active ribozyme, for the proposed assay the optimum concentration will be determined (0.1-1 mM will be tested). The products of the splicing reaction will be analyzed. It is expected that the splicing reaction performed in the presence of RNA A will not yield the spliced RNA. In contrast, the reaction carried out in the presence of RNA A, RNA B and theophylline will result into mRNA.

Another aspect of the present invention relates to methods of modulating RNA splicing in a subject using theophylline and theophylline-dependent riboswitch. The experiments described in the application demonstrate that the aptamer selected in vitro could retain its target recognition property in a cell free system or when expressed inside the living cells. If theophylline-RNA interaction could control a 3' splice site switch in a model pre-mRNA (FIG. 10), it is reasonable to expect that it might also regulate the alternative splicing of a physiologically relevant trans-gene in a subject (e.g., a model organism). However, before undertaking experiments in transgenic animals, it will be prudent to test theophylline modulation with cultured cells or extracts prepared from such cells.

Figure 18:
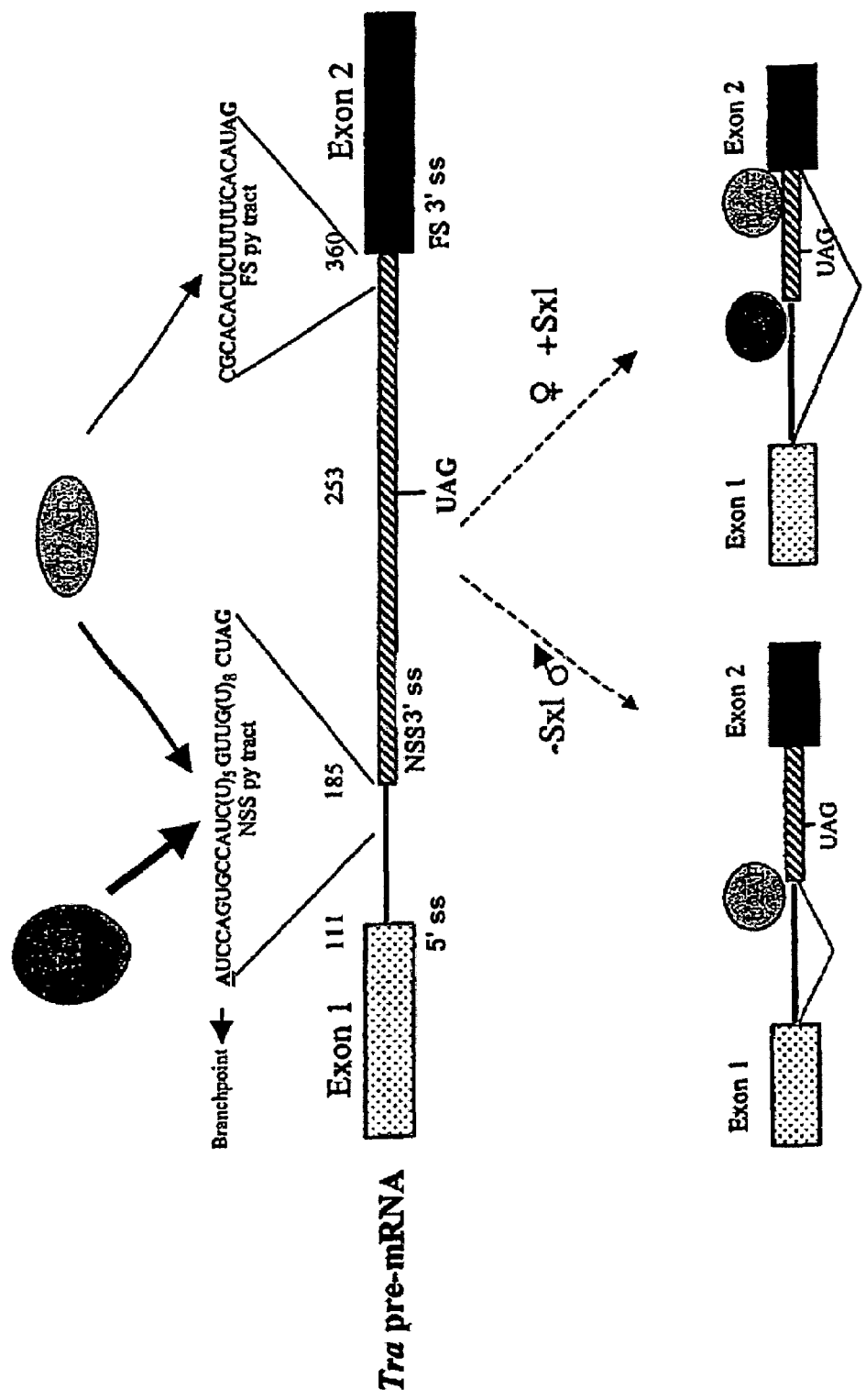
FIG. 18. Model for the regulation of tra pre-mRNA splicing by Sex-lethal protein. Line: non-sex-specific intron; striped box: female specific portion of tra intron; NSS: non-sex specific; FS: female specific.

In one embodiment, *Drosophila* cells are used for the test. *Drosophila* sexual differentiation involves a hierarchy of alternative splicing events, which are the best-characterized examples of alternative splicing regulation (Black, 2003; Cline and Meyer, 1996; Lopez, 1998). The *Drosophila* protein sex-lethal (Sxl), which is the master sex-switch in somatic cells and only expressed in female flies, regulates the alternative splicing of transformer (tra) pre-mRNA (Boggs et al., 1987; Granadino et al., 1997; Inoue et al., 1990; Sosnowski et al., 1989; Valcarcel et al., 1993). Experiments in transgenic flies and with nuclear extracts prepared from HeLa as well as *Drosophila* cells have demonstrated that Sxl protein blocks the binding of general splicing factor U2AF to NSS 3' ss and thereby diverting it to activate the lower affinity female specific (FS) 3' splice site (Inoue et al., 1990; Sosnowski et al., 1989; Valcarcel et al., 1993) (FIG. 18). In contrast, lack of Sxl expression in male flies leaves U2AF to bind to the NSS Py tract, enabling the synthesis of a truncated non-functional protein (FIG. 18). Our hypothesis is that if the AG of NSS 3' splice site were to be the part of a high-affinity theophylline-binding site, then binding of theophylline to its cognate sequence would sequester NSS 3' splice site thus, allowing the activation of female specific 3' splice site.

Figure 19:
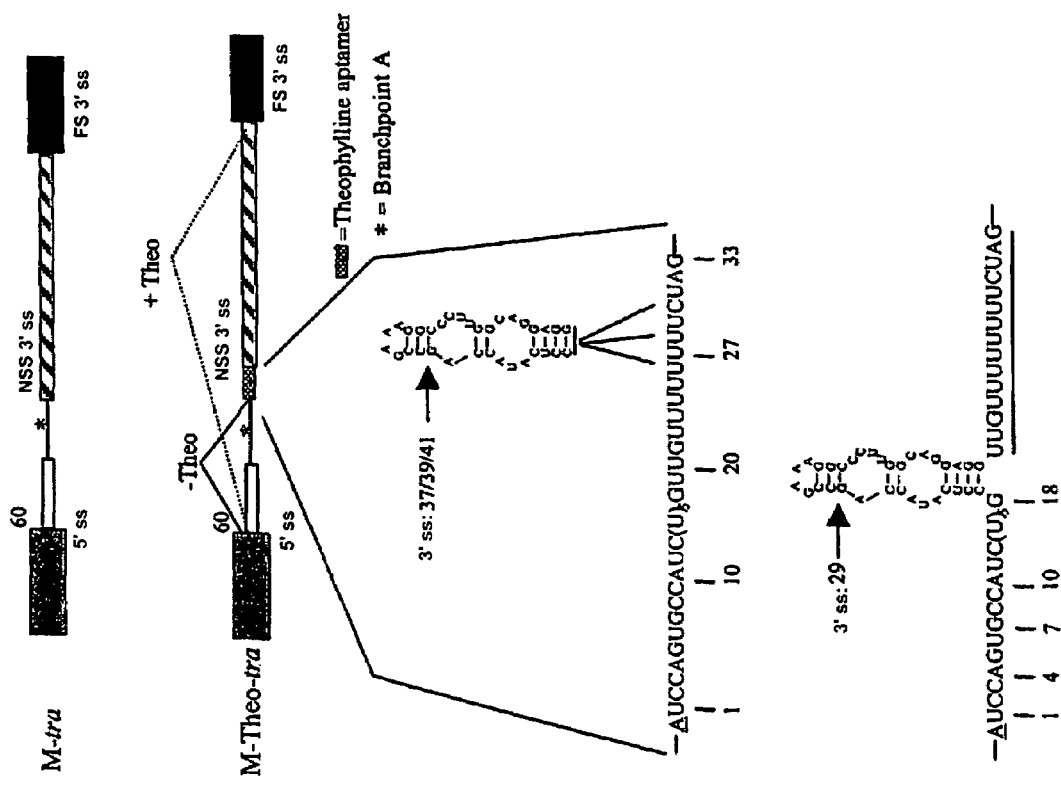
FIG. 19. Proposed scheme for the construction of M-Theo-tra derivatives.

To test theophylline-mediated modulation of tra splicing, a series of M-tra derivatives carrying the high affinity theophylline-binding site at various positions 5' to the NSS 3' splice site junction will be constructed (FIG. 19 and see below). M-tra is a derivative of tra, which was designed to overcome the low in vitro splicing efficiency of tra, and has been shown to faithfully recapitulate *Drosophila* gender specific splicing in HeLa as well as in *Drosophila* nuclear extracts (Valcarcel et al., 1993). In addition, M-tra lacks exon 3, which is included in both sexes.

Figure 20:
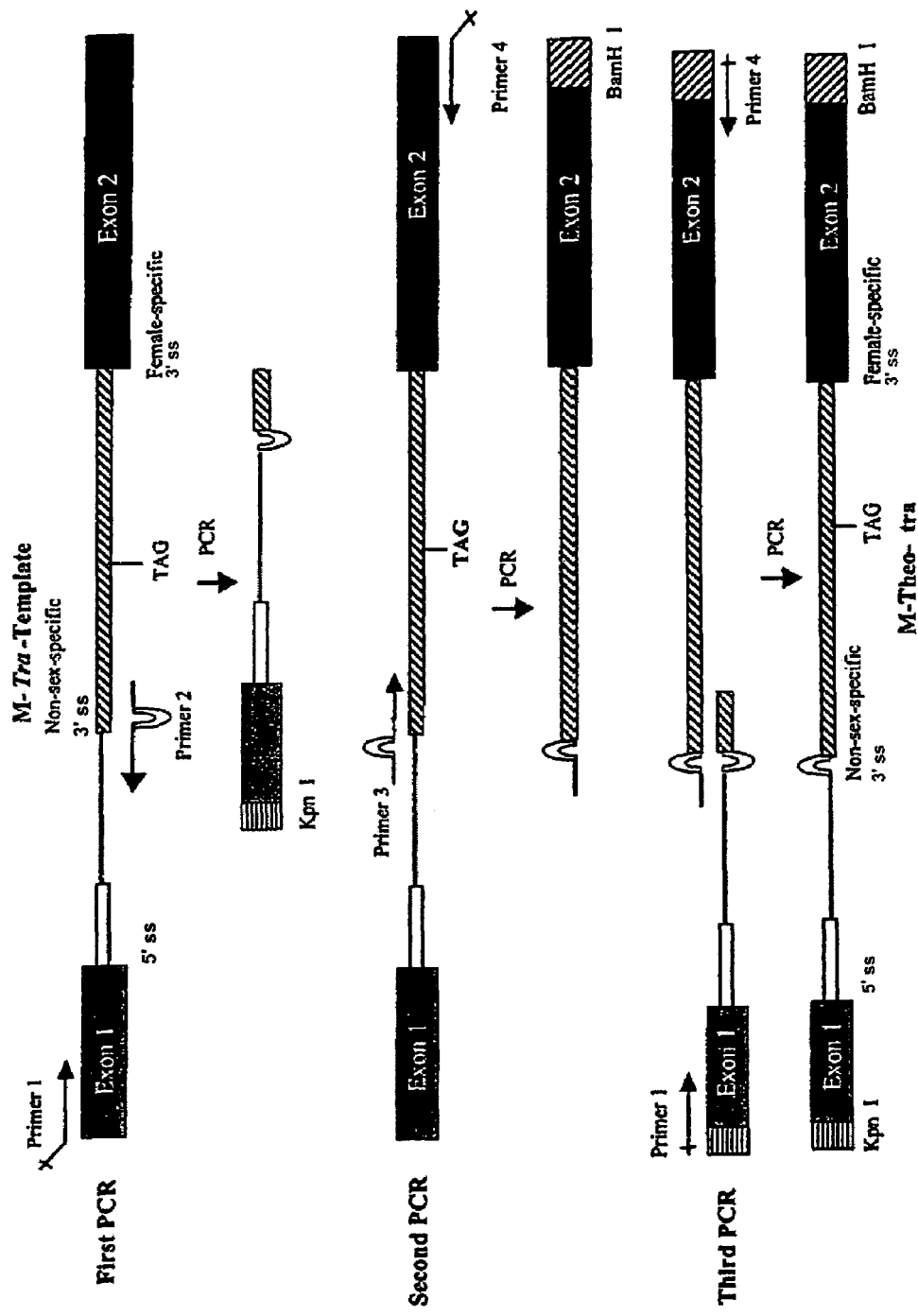
FIG. 20. Overlapping PCR for the construction of M-Theo-tra templates.

As outlined in FIG. 20, an overlapping PCR approach will be used to generate M-Theo-tra derivatives containing theophylline-binding site at positions 26, 28 and 30. In the first PCR, the portion of M-Theo-tra encompassing the first exon and non-sex-specific 3' splice site will be generated using forward (Primer #1) and reverse primers (Primer #2). The forward primer will be specific for the first exon and the reverse primer will be designed to bind the NSS 3' splice site and carry the theophylline aptamer sequence. The second PCR will be carried out with a forward primer (Primer #3) whose 5' end will be overlapping to the 3' end of the first PCR product, and the reverse primer will be designed to bind 3' end of the second exon (Primer #4). In the third PCR, the products of first two PCRs will be annealed and forward and reverse primers from the first and second PCRs, respectively will be used. The gel purified PCR product will be cloned downstream of T7 promoter in KpnI/BamHI digested pBluescript SK (Stratagene) to yield pM-Theo-tra37, pM-Theo-tra39 and pM-Theo-tra41. The plasmids pM-mutTheo-tra37, pM-mutTheo-tra39 and pM-mutTheo-tra41, each one carrying a mutation in the theophylline-binding site, and is expected not to bind theophylline, will also be generated (Zimmermann et al., 2000). The authenticity of these constructs will be confirmed by sequencing.

To determine whether M-Theo-tra can recapitulate gender specific splicing of tra, $^{32}$P-labeled M-Theo-tra pre-mRNA will be incubated in HeLa nuclear extract in the presence of theophylline or caffeine as described in FIG. 3. The splicing of M-mutTheo-tra will also be performed in an identical manner. The M-theo-tra derivative in which the addition of theophylline inhibits NSS 3' splice site with simultaneous activation of FS 3' splice site would be the desired substrate and will be used in future experiments. Additionally, in the absence of theophylline or in the presence of caffeine, this substrate is expected to undergo male specific default splicing. Finally, none of the M-mutTheo-tra derivatives (negative control) are expected to undergo theophylline-dependent 3' splice site switch.

Figure 21:
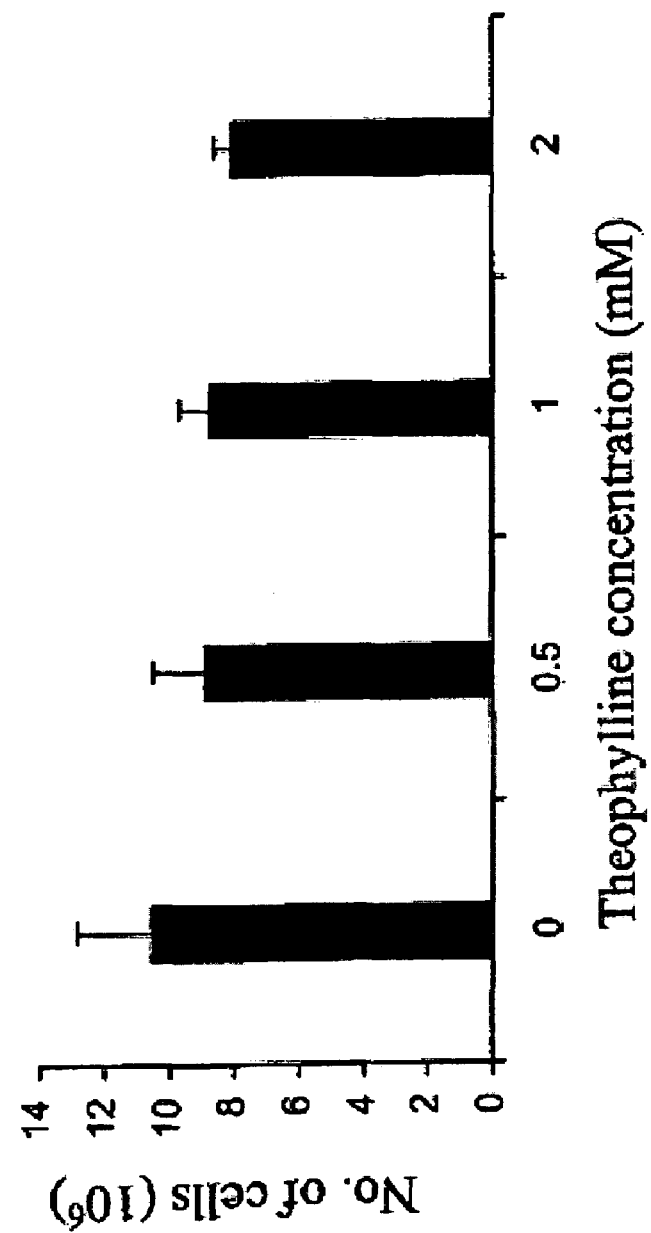
FIG. 21. *Drosophila* Schneider cell viability assay.

It was further investigated whether theophylline could be used to regulate splicing of tra in a more physiological and biologically meaningful context, for example, in *Drosophila* Schneider cells (SL-2). *Drosophila* Schneider cells (SL-2), which are known to be male with respect to Sxl expression provides an excellent model system for studying the underlying mechanisms that control the sex determination pathway (Ryner and Baker, 1991). Before theophylline could be employed as a regulatory molecule it is important to determine whether theophylline has any adverse effect on the growth of Schneider cells. To this end, Schneider's cells ($2\times10^6$, per well) were seeded in a six well plate in 3 ml *Drosophila* medium supplemented with 5% FCS and L-glutamine (Invitrogen). The cells were grown at 27° C. without CO2 in the absence or presence of theophylline. After 72 h, cell were harvested and resuspended in PBS containing trypan blue (0.05%). The cells were counted using hemocytometer. Dead cells were identified by uptake of the trypan blue; live cells by exclusion of the trypan blue marker. In FIG. 21, the growth rate for Schneider's cells in the presence of indicated concentrations of theophylline (an average of three identical experiments were performed in parallel) is shown. The data indicates that even at the highest concentration of theophylline (2 mM) the growth profile of majority of cells is not altered. Because 0.1-0.5 mM theophylline is sufficient to inhibit pre-mRNA splicing (FIG. 11), Schneider's cells can be safely used to study theophylline-dependent regulation of tra splicing.

It is contemplated that the M-theo-tra derivative (FIG. 19), which responds best to theophylline-dependent gender specific splicing, will be used in here. M-theo-tra will be subcloned downstream of metallothionein promoter in a *Drosophila* expression vector pRmHa-3, a generous gift from Juan Valcarcel. The expression plasmid pRmHa-3 is a pUC18 based vector and contains the promoter, metal response element and transcription start site from the metallothionein gene followed by the multiple cloning site, and the polyadenylation signal (A+) from the *Drosophila melanogaster* alcohol dehydrogenase (ADH) gene. The *Drosophila* expression vector (pRM-mutTheo-tra) harboring an analog of M-Theo-tra, which contains a mutation in theophylline-binding site, will also be constructed. The construction of these plasmids will be carried out following standard molecular cloning techniques. In brief, PCR amplified fragments encoding M-Theo-tra or M-mutTheo-tra will subcloned into EcoR I/Sal I digested pRmHa-3 to yield pRM-theo-tra. The authenticity of the inserts will be confirmed by direct sequencing.

Schneider cells will be transiently transfected with pRM-theo-tra, pRM-mutTheo-tra or with empty vector (pRmHa-3). In brief, Schneider cells ($2\text{-}3\times10^6$ cells/well) will be seeded in a six well plate in 3 ml *Drosophila* medium (Gibco) supplemented with 5% FCS, and 50 µg/ml gentamycin. The following day, cells will be washed with 2-3 ml of serum free medium, and transfected with 0.5-3.0 µg plasmid (the total amount of DNA will be kept constant by using empty vector) using CellFectin (Invitrogen) following manufacture's instructions. The amount of DNA and the transfection time will be standardized and the conditions that result in highest transfection efficiency will be used. After 18-24 h, the DNA-containing medium will be replaced by 3 ml of *Drosophila* medium and cells will be allowed to grow for another 24 h. At this stage theophylline or caffeine will be added and the transcription will be induced by CuSO4 (0.7-1.0 µg). After an incubation of 24 and 48 h, cells will be collected, washed with ice cold PBS, total RNA will be isolated with PARIS™ Kit (Ambion), and analyzed by RT-PCR. Since the timing of theophylline addition (after transfection), concentration of copper sulfate and induction time could affect the outcome of an experiment; each of these factors will separately optimized. Although every effort will be made to maintain Schneider cells under optimal culture conditions according to the published protocol (Bunch et al., 1988), cultured cells are known to change their properties with repeated passages. Therefore key findings obtained with Schneider cells will also be studied in other cell line such as *Drosophila* Kc cells.

It is contemplated that both pRM-Theo-tra and pRM-mutTheo-tra transfected cells, untreated or treated with caffeine, are expected to undergo male specific splicing, i.e., the NSS 3' splice site will be activated, which would be confirmed by ~383-bp PCR product. Upon theophylline treatment, pRM-theo-tra, but not pRM-mutTheo-tra transfected cells, is expected to generate female specific splicing (~186-bp band in RT-PCR) 3. Finally, pRmHa-3 (vector only) transfected cells will be negative in terms of M-Theo-tra splicing.

Another aspect of the present invention relates to methods of placing or inserting a theophylline aptamer into the 5' splice site and determining whether a theophylline-dependent riboswitch would modulate the 5' splice site choice in the presence of theophylline. Another aspect of the present invention relates to methods of modulating RNA splicing comprising the steps of inserting a theophylline aptamer into the 5' spice site and modulating pre-mRNA splicing in the presence of theophylline.

Another aspect of the present invention relates to methods of placing or inserting a theophylline aptamer into the BPS and determining whether a theophylline-dependent riboswitch would modulate pre-mRNA splicing in the presence of theophylline. Another aspect of the present invention relates to methods of modulating RNA splicing comprising the steps of inserting a theophylline aptamer into the BPS and modulating pre-mRNA splicing in the presence of theophylline.

In recent years tremendous efforts have been made in the development of tools that could manipulate gene expression at the level of transcription. For example, sequence specific DNA binding of pyrrole-imidazole polyamide oligomers has been exploited to control transcription (Gottesfeld et al., 1997). Likewise, principle of chemically induced proximity has been used for the development of small molecule-based approach for the regulation of transcription (Belshaw et al., 1996; Ho et al., 1996). Although controlling gene expression at the level of transcription is useful, to be able to control pre-mRNA splicing will have many applications in biology and medicine. For instance, a theophylline-dependent trans gene whose expression is turned on/off at a specific time in the development can be used to study the function of a developmentally regulated gene. Similarly, if a gene of interest encodes a transcription factor, a trans gene could be designed so that its alternative splicing modulated by theophylline would generate mRNAs encoding transcription activator and repressor molecules that bind to the same sequence of the promoter.

Another aspect of the present invention relates to riboswitch and a small molecule-based approach for controlling gene expression at the level of splicing. The approach is based on the principle of riboswitch in which the binding of a small molecule ligand to the specific RNA sequence leads to the formation of a stem loop structure that either terminates transcription prematurely or sequesters the Shine-Dalgarno sequence and inhibits translation initiation (Nudler and Mironov, 2004). Since aptamers can also bind small molecule ligands, it is interestingly found that insertion of an aptamer within the 3' splice site region of a pre-mRNA generates an artificial riboswitch that may enable ligand specific control of pre-mRNA splicing.

A series of model pre-mRNAs in which the 3' splice site AG was engineered to be the part of theophylline-binding aptamer were constructed and tested for their ability to undergo pre-mRNA splicing in the absence or presence of theophylline (FIGS. 2-5). These substrates differ in terms of the BPS-to-AG distance and the location of the 3' splice site AG within the theophylline binding aptamer. In AdML-Theo39AG, step II of splicing was nearly abolished in the absence of theophylline (FIG. 2C, lanes 6-9), and our observation that lowering of the BPS-to-AG distance by 10 (FIG. 3, AdML-Theo29AG) or 12 nucleotides (FIG. 4, AdML-Theo27AG) rescued this inhibition is consistent with the previously published reports which suggest that: 1. Although the normal BPS-to-AG distance in vertebrates is 18-40 nucleotides, utilization of an AG farther than 30 nucleotides downstream of the BPS significantly reduces the efficiency of the second step of the splicing (Chua and Reed, 2001), and 2. Insertion of pyrimidines upstream of such an AG alleviates the poor step II splicing (Chiara et al., 1997; Patterson and Guthrie, 1991).

Figure 5:
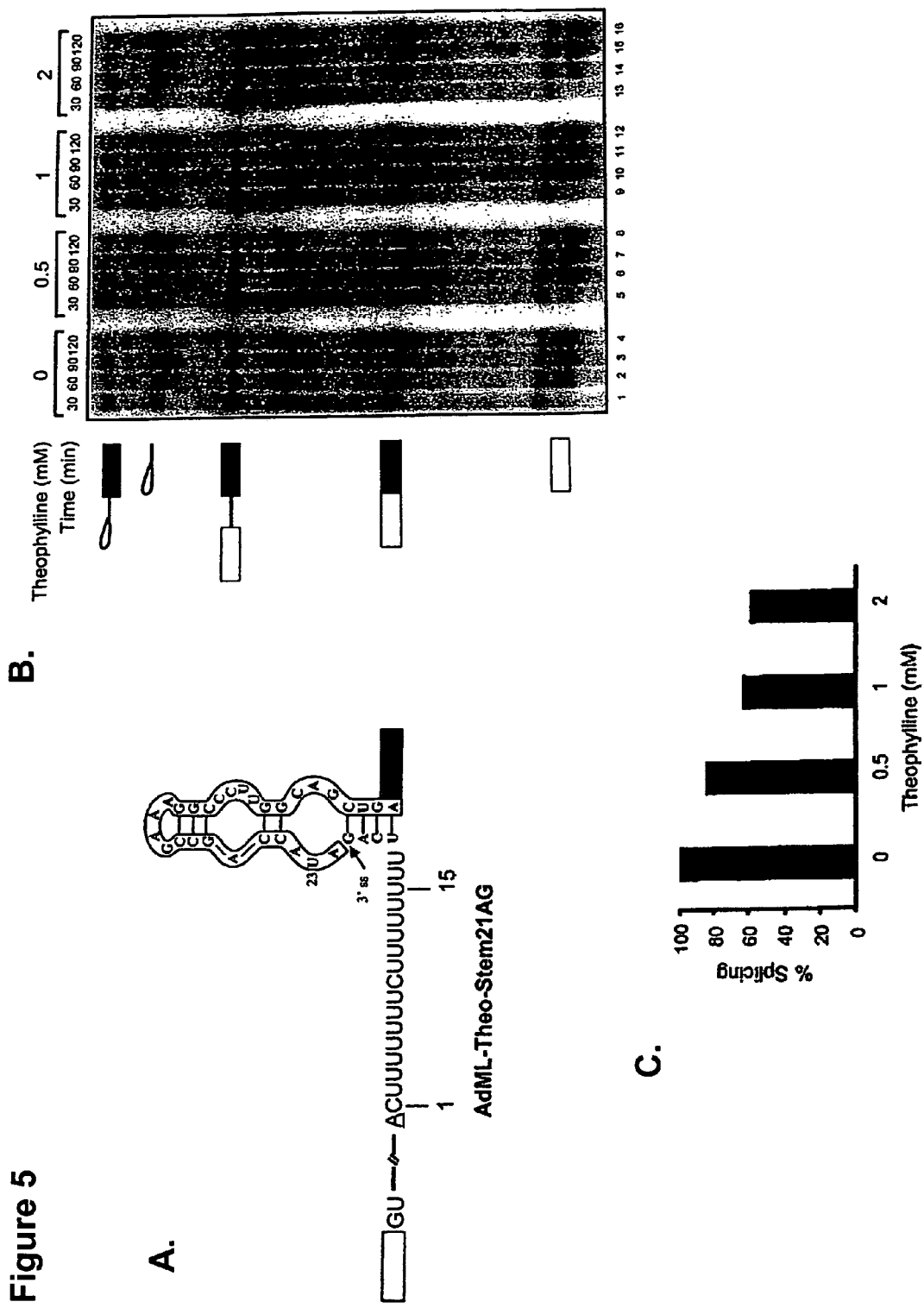
FIG. 5. Pre-mRNA in which 3' ss AG is outside the theophylline core does not confer theophylline-mediated regulation of splicing. (A) Schematic representation of AdML-Theo-Stem21AG pre-mRNA (SEQ ID NO: 19). (B), Splicing time course with the AdML-Theo-Stem21AG substrate. $^{32}$P-Labeled AdML-Theo-Stem21AG pre-mRNAs was subjected to in vitro splicing in the absence (lanes 1-4) or with indicated concentration of theophylline (lanes 5-16) as described in FIG. 2. The extracted RNA was fractionated on a 13% polyacrylamide denaturing gel. The position of the pre-mRNAs, splicing intermediates, and spliced products is indicated on left. (C), Histogram representing the effect of theophylline on the splicing efficiency of AdML-Theo-Stem21AG pre-mRNA at 120 min time point (from B) as described in FIG. 4.

Experimental data included herein indicate that AdML-Theo29AG, AdML-Theo27AG and AdML-Theo-Stem21AG pre-mRNAs conferred theophylline dependent control of splicing, albeit with varying degree (FIGS. 3-5, also see below). While 0.5 mM theophylline was able to inhibit the splicing of AdML-Theo29AG by more than 50%, a 4-fold higher concentration of theophylline was required to achieve the same level of inhibition in AdML-Theo27AG (FIGS. 3D and 4C). Increasing the concentration of theophylline to 2.0 mM, however, reduced this difference to <2-fold (FIGS. 3D and 4C). This difference, which corresponds to only ~0.5 kcal/mol, can not account for the loss of three base pairing interactions between AdML-Theo29AG and AdML-Theo27AG (a hydrogen bond can contribute from 0.5 to 2.0 kcal/mol to the stability of a base pair), suggesting that the unpaired region of theophylline aptamer makes the major contribution towards the overall binding energy. This may explain why none of the 15 residues (FIG. 1B, nucleotides shown in the box) required for high affinity theophylline binding resides in the lower stem (Jenison et al., 1994; Zimmermann et al., 2000).

Unlike AdML-Theo29AG and AdML-Theo27AG substrates, the normal step II of the splicing of AdML-Theo-Stem21AG in the absence of theophylline (see accumulation of lariat-exon 2 in lanes 2-5, FIGS. 3B and 4B versus no accumulation in lanes 1-4 FIG. 5B) further confirmed the BPS-to-AG distance rule (Chiara et al., 1997; Chua and Reed, 2001; Patterson and Guthrie, 1991). However, the poor response of AdML-Theo-Stem21AG to theophylline-mediated step II splicing inhibition is somewhat intriguing (compare FIGS. 3D, 4C-5C). Two explanations can be offered to this observation: First, while present in the lower stem of the aptamer, the AG could still serve as a 3' splice site. Given that the 3' splice site AG as well as the nucleotides in its vicinity have been shown to interact with the nucleotides at the 5' splice site (Collins and Guthrie, 1999; Collins and Guthrie, 2001; Deirdre et al., 1995; Parker and Siliciano, 1993) and with the conserved loop of U5 snRNA (Sontheimer and Steitz, 1993), it is highly unlikely that while sequestered in the double-stranded stem the AG could maintain these interactions. An alternative explanation is that after the completion of the first step or just prior to the step II of the splicing, the spliceosome unwinds the lower stem of the aptamer and select this AG as splice acceptor site. Support to this explanation comes from the fact that the second step of the splicing is preceded by a major conformational rearrangement aided in part by putative RNA helicases, which likely unfold the lower stem (Staley and Guthrie, 1998; Umen and Guthrie, 1995).

Data disclosed herein indicate that even at the highest concentration of theophylline, 20-25% of the AdML-Theo29AG pre-mRNA underwent step II of splicing (FIGS. 3B and 3D). This could most likely be due to the differential metal ion requirements for the binding of theophylline to its cognate RNA and in vitro splicing; while high affinity theophylline-RNA aptamer binding requires 5.0 mM $Mg^{2+}$ (Jenison et al., 1994; Zimmermann et al., 2000), ~3.0 mM $Mg^{2+}$ has been found to be optimum for in vitro splicing (Krainer et al., 1984). Since the in vitro splicing experiments were performed in the presence of ~3.0 mM $Mg^{2+}$, the observed incomplete splicing inhibition could be the consequence of weak theophylline-aptamer binding. In addition, the design of the pre-mRNA construct could also account for the incomplete repression of splicing. For example, unavailability of a competing 3' splice site likely forced the splicing machinery to select a structured AG. This interpretation is in agreement to the previously reported studies in which the repression of a targeted splice site was significantly higher when an alternative splice site was available (Goguel et al., 1993; Villemaire et al., 2003).

Figure 8:
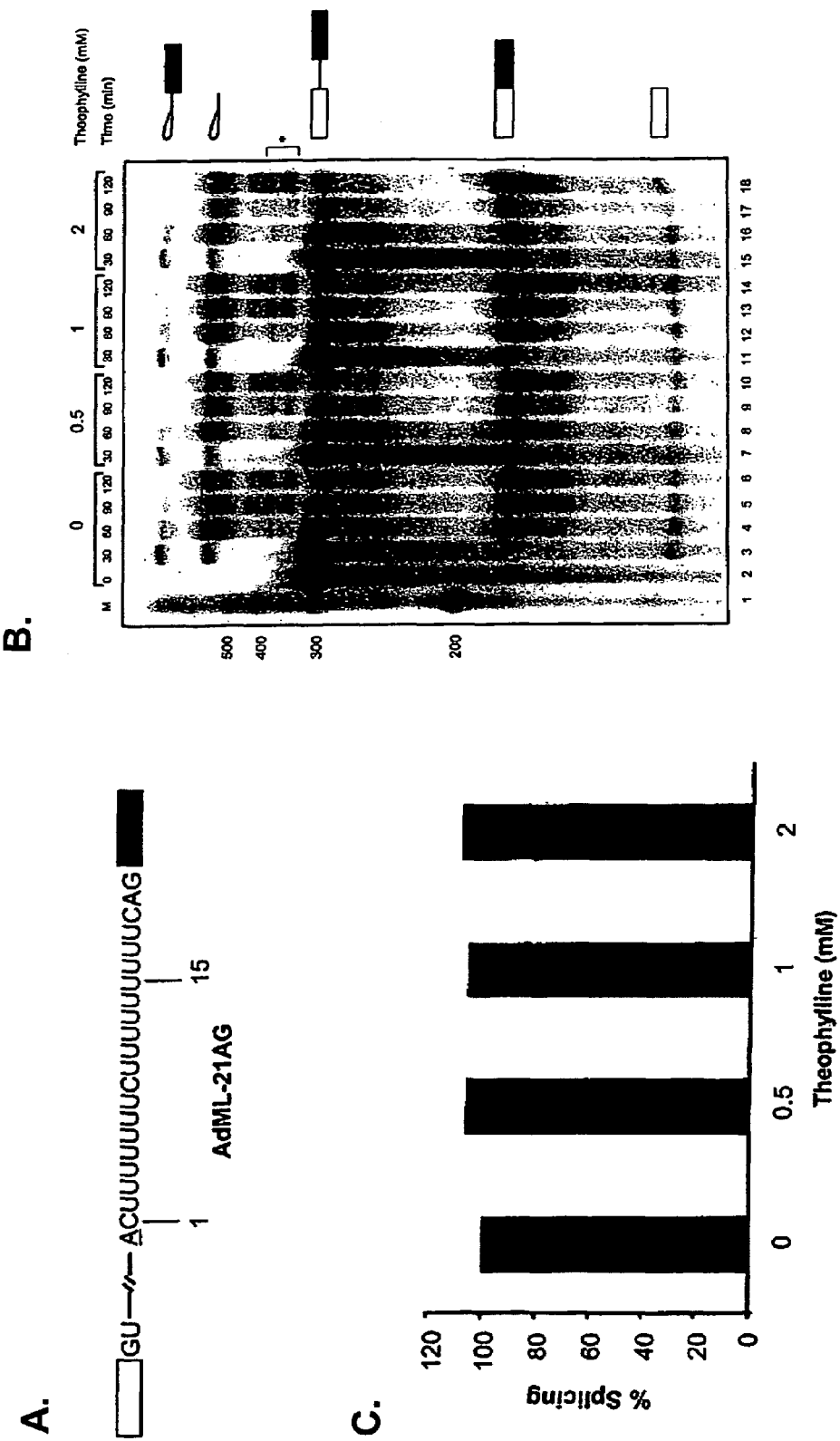
FIG. 8. Theophylline-dependent regulation of pre-mRNA splicing is highly specific. (A) Schematic representation of AdML-21AG pre-mRNA (SEQ ID NO: 21). (B), Splicing time course with the AdML-21AG pre-mRNA. $^{32}$P-Labeled AdML-21AG pre-mRNA was subjected to in vitro splicing in the absence (lanes 2-6) or with increasing concentration of theophylline (lanes 7-18) as described in FIG. 2. The extracted RNA was fractionated on a 13% polyacrylamide denaturing gel. The position of the pre-mRNAs, splicing intermediates, and spliced products is indicated on right. An asterisk (*) indicates degraded lariat. (C), Histogram representing the effect of theophylline on the splicing efficiency of AdML-21AG pre-mRNA at 120 min time point (from B) as described in FIG. 4.

Several lines of evidence argue strongly that the observed theophylline dependent inhibition of step II of the splicing is specific. First, theophylline mediated decrease in the yield of the spliced product is directly proportional to the amount of the lariat product, suggesting that the inhibition of AdML-Theo-29AG splicing is not the result of mRNA degradation (see lariat and spliced product in FIG. 3B, lanes 2-17). Second, the lower yield of the mRNA is mirrored by the accumulation of lariat-exon 2, confirming that the splicing was specifically blocked at the second step (FIG. 3C). Third, even at the highest concentration, theophylline does not affect the efficiency of the first step of splicing, thus excluding the possibility that the lower efficiency of the first step of splicing might be the cause of reduced level of mRNA (FIG. 3D). Fourth, theophylline failed to affect the splicing of pre-mRNAs in which the theophylline aptamer was inserted to 8 or 10 nucleotides downstream of 3' or 5' ss, respectively (FIG. 6 and data not shown). Fifth, even at the highest tested dose, theophylline failed to elicit any effect on the splicing of a pre-mRNA that does not contain its binding site (FIG. 8). Finally, caffeine, which is similar in shape and size to theophylline, had no effect on the splicing of AdML-Theo-29AG pre-mRNA (FIG. 9).

The formation of RNA secondary structure has been known to account for the regulation of splicing in a number of natural pre-mRNAs (Buratti et al., 2004). In addition, the effects of artificial stem-loop structures on the splicing of pre-mRNAs in yeast (Goguel and Rosbash, 1993; Goguel et al., 1993), mammals (Eperon et al., 1988; Liu et al., 1997; Solnick, 1985) and plants (Goodall and Filipowicz, 1991; Liu et al., 1995) have also been investigated. More recently, the analysis of human intronic sequences has revealed a strong correlation between alternative splicing and the prevalence of tandem nucleotide repeats that have the potential of forming secondary structure in introns that flank alternatively spliced exons (Lian and Garner, 2005). Given these facts, it would be interesting to test whether or not the RNA-theophylline system developed here could be used to influence a 3' splice site switch of a pre-mRNA in which a common 5' splice site pairs with two alternative 3' splice site.

In conclusion, we have demonstrated that an artificial riboswitch, which exploits the high affinity binding of theophylline to an in vitro evolved aptamer, can regulate pre-mRNA splicing. Theophylline-dependent control of pre-mRNA splicing may have many advantages. First, theophylline is a well-known drug with favorable pharmacokinetic and cellular uptake properties. Second, theophylline is highly stable and possesses good water solubility. Third, theophylline is commercially available and is inexpensive. Finally, theophylline binds to its cognate sequence with high affinity and specificity, and the BLAST search of the human genome revealed no apparent match for theophylline aptamer sequence.

Figure 22:
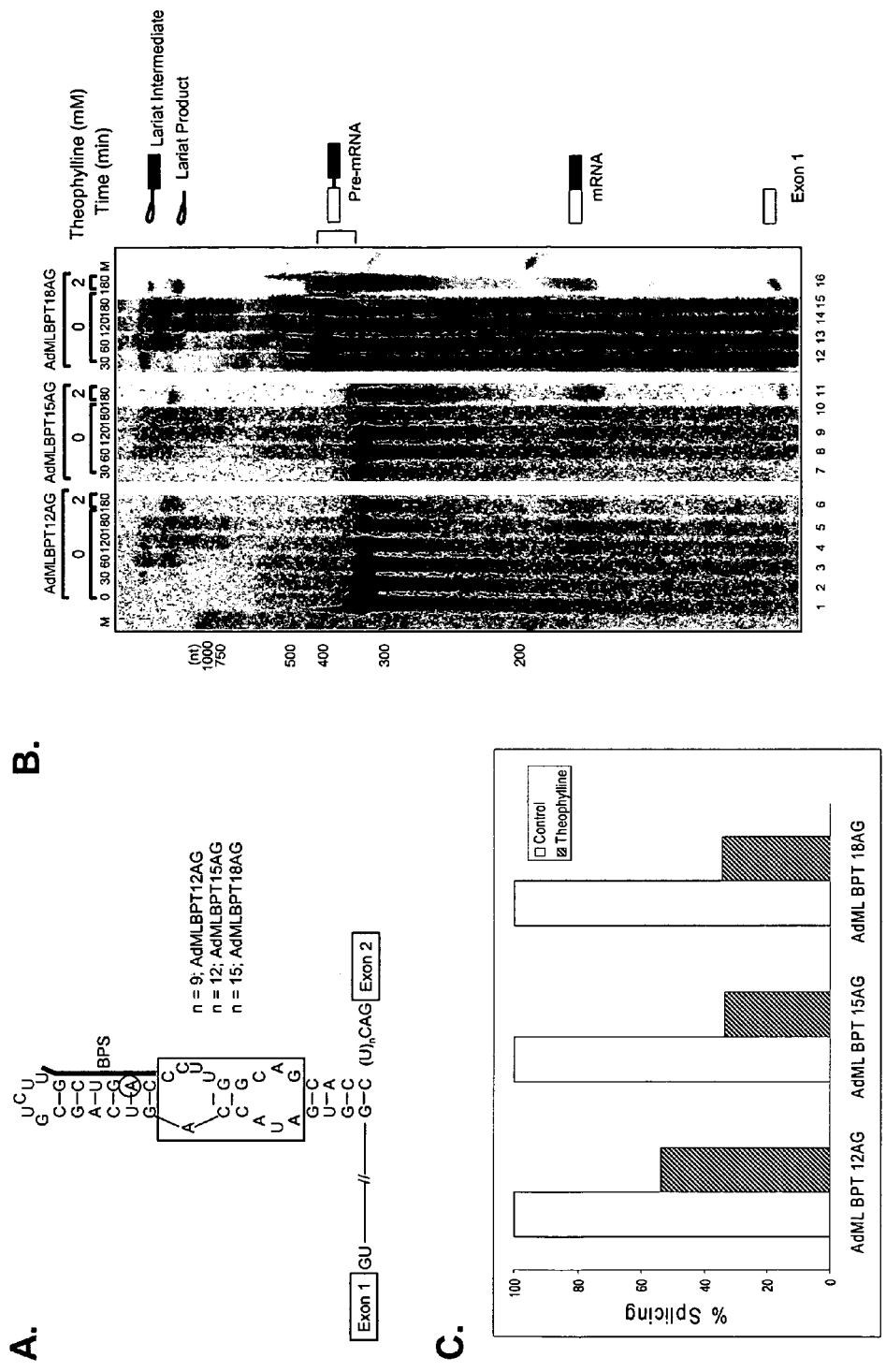
FIG. 22. Theophylline-responsive riboswitch confers ligand dependent control of splicing. (A), AdML pre-mRNA derivatives (AdMLBPT12AG (SEQ ID NO: 25), AdMLBPT15AG (SEQ ID NO: 26), and AdMLBPT18AG (SEQ ID NO: 27)) in which the branchpoint sequence is inserted within the upper stem of theophylline binding sequences. (B), $^{32}$P-labeled pre-mRNAs were synthesized as run-off transcripts from linearized plasmids (1 µg) using T7 RNA polymerase. Gel purified pre-mRNAs were subjected to in vitro splicing in the absence or presence of theophylline by incubating in HeLa nuclear extract. Addition of theophylline to the splicing reaction significantly lowered the yield of the spliced product (Compare lanes 6, 11 and 16 with lanes 2-5, 7-10 and 12-15, respectively. (C), Quantification of the data in panel B. Percent splicing was calculated by amount of mRNA product over the sum of pre-mRNA and mRNA.
Figure 23:
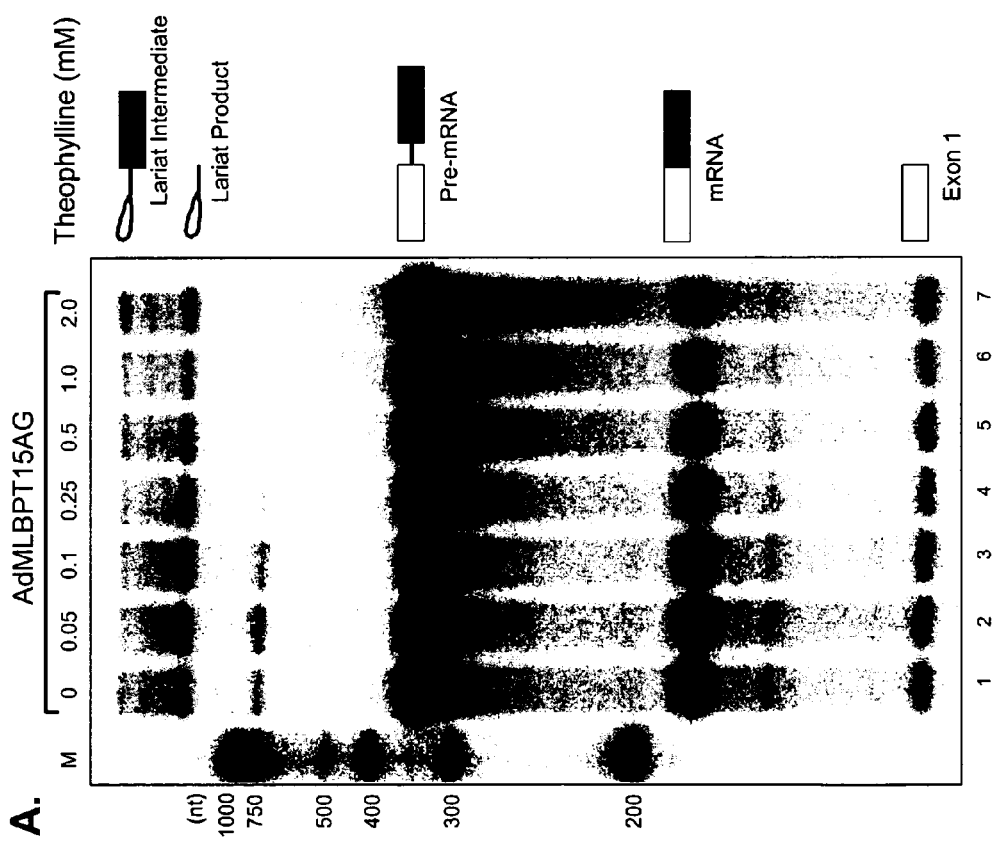
FIG. 23. Theophylline inhibits splicing in a dose dependent manner. (A), $^{32}$P-labeled AdML BPT15AG pre-mRNA was incubated in HeLa nuclear extract (experimental details described in FIG. 2) in the absence or with increasing concentrations of theophylline. (B), Quantification of data indicate that while 250 µM of theophylline can affect splicing reaction, 0.5 mM theophylline is sufficient to achieve ~50% splicing inhibition.

Since the choice of alternative splice sites is generally made at early stages of spliceosome assembly, it was next examined whether a theophylline riboswitch could be engineered to control splicing prior to the first step. A series of pre-mRNA substrates were constructed in which the branchpoint sequence (BPS) was inserted within the theophylline aptamer. In AdML pre-mRNA derivatives in which the branchpoint sequence is inserted within the upper stem of theophylline binding sequences, normal splicing was observed in the absence of theophylline, albeit with varying efficiency (FIG. 22B, lanes 2-5, 7-10, and 12-15). However, addition of theophylline to the splicing reaction significantly lowered the yield of the spliced product (FIG. 22B, lanes 6, 11, and 16; FIG. 22C). AdML BPT15AG, which showed the most significant effects in the presence of theophylline, was chosen for further experiments. To determine whether theophylline-mediated inhibition was dose dependent and to identify the optimum concentration for controlling splicing, the splicing experiment was repeated using AdML BPT15AG in the presence of varying concentrations of theophylline. Theophylline as found to inhibit splicing in a dose-dependent manner (FIGS. 23A and B). While 250 µM of theophylline could affect the splicing reaction, 0.5 mM theophylline was necessary to achieve 50% splicing inhibition (FIG. 23B).

Figure 24:
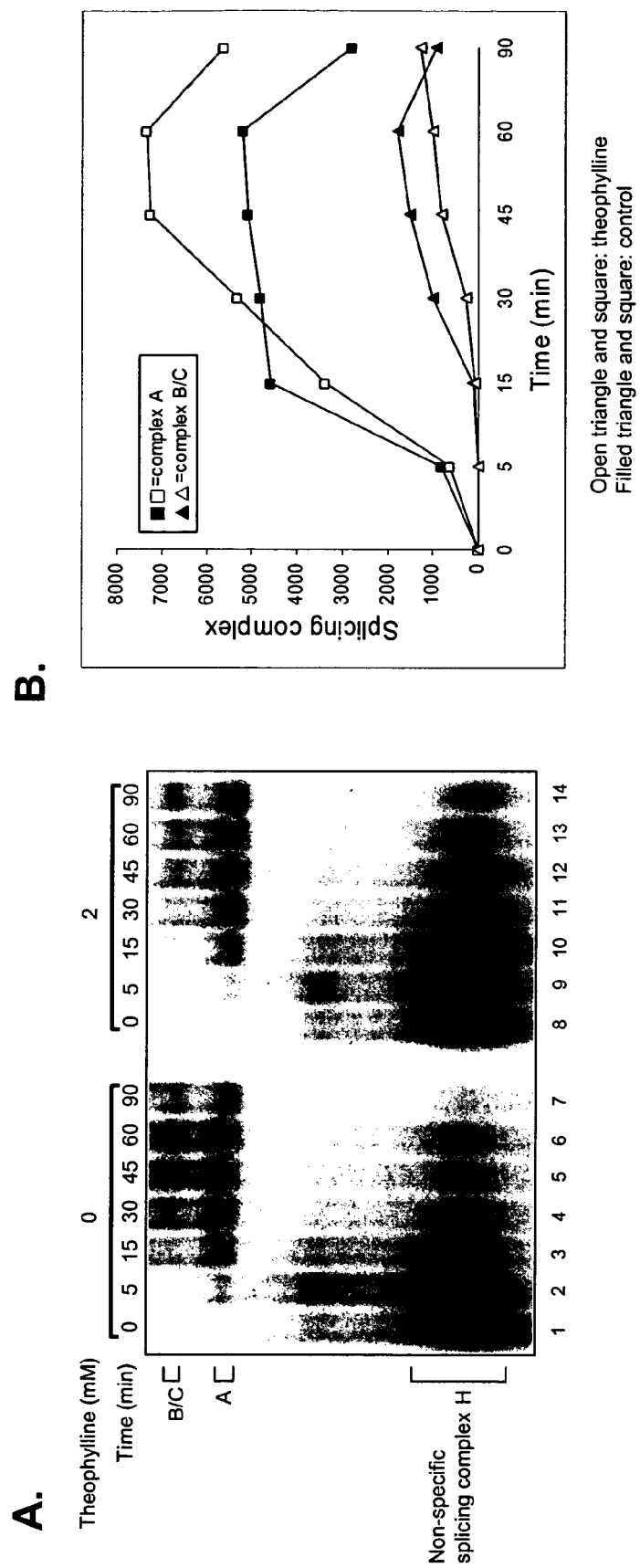
FIG. 24. Theophylline inhibits splicing by blocking spliceosome assembly. (A), $^{32}$P-labeled AdML BPT15AG pre-mRNA was incubated in HeLa extract for designated time at 30° C. without or with 2 mM theophylline. Aliquots were withdrawn at various time points, followed by the separation of complexes on native agarose gels according to the published protocol (Das and Reed, 1999). The bands representing splicing complex H, A and B/C are marked on the left. (B), Quantification of data from (A).

To investigate whether theophylline inhibits pre-mRNA splicing by blocking the step(s) in the assembly of the spliceosome or simply interferes with the chemical step(s) of splicing, splicing complex assembly was analyzed. Spliceosome assembly assays were performed in the presence or absence of 2 mM theophylline. Addition of theophylline significantly affected the kinetics of spliceosome assembly (FIG. 24A, compare lanes 1-7 and lanes 8-14). For example, in the absence of theophylline, splicing complex A was detected at approximately five minutes and converted into complex B/C at approximately 30 minutes. This process peaked between 45-60 minutes, and declined after 90 minutes of incubation. In contrast, splicing complex A appeared as early as approximately five minutes in the presence of theophylline, but its conversion to complex B/C was significantly impaired. In addition, theophylline affected the kinetics of complex H to A transformation. While the majority of complex H disappeared after 30 minutes of incubation, in the presence of theophylline it persisted even after 90 minutes. Thus, theophylline inhibits pre-mRNA splicing by blocking assembly of the spliceosome.

Figure 25:
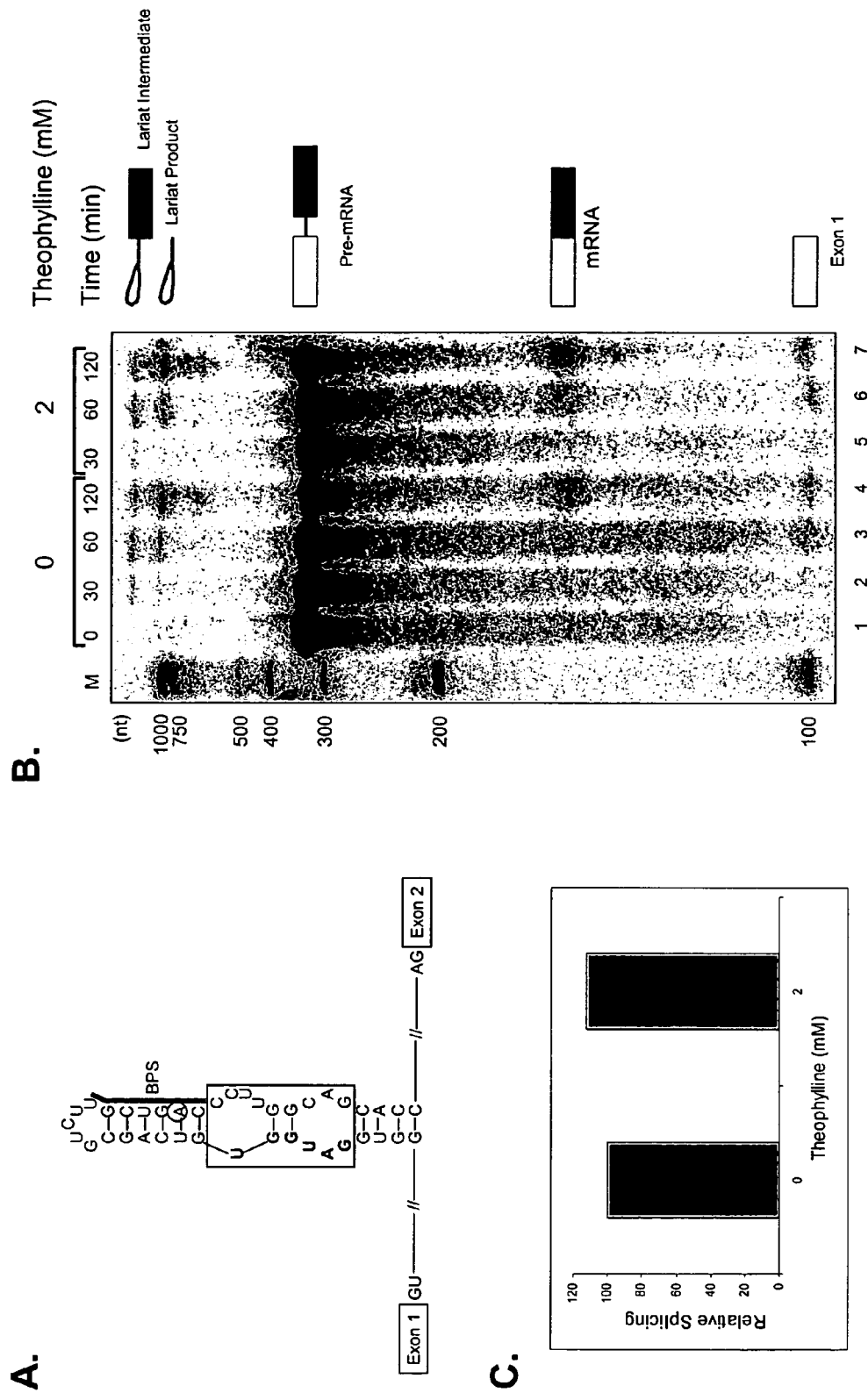
FIG. 25. Theophylline dependent inhibition of splicing is specific. (A), Nucleotides that are necessary for theophylline binding were mutated to generate BrkBpTheo pre-mRNA (SEQ ID NO: 28). (B), $^{32}$P-labeled pre-mRNAs were subjected to in vitro splicing in the absence or presence of theophylline by incubating in HeLa nuclear extract. (C), Quantification of data from (B). Splicing of BrkBpTheo remained virtually unaffected at 2 mM theophylline.

To determine whether theophylline-dependent splicing is specific, nucleotides that are necessary for theophylline binding (boxed residues in FIG. 1A) were mutated. The resultant pre-mRNA (BrkBpTheo) was not expected to bind theophylline, and thus should remain unaffected during in vitro splicing in the presence of theophylline. This was indeed the case, as splicing of BrkBpTheo remained virtually unaffected even at the maximum tested dose of theophylline (FIG. 25).

Figure 26:
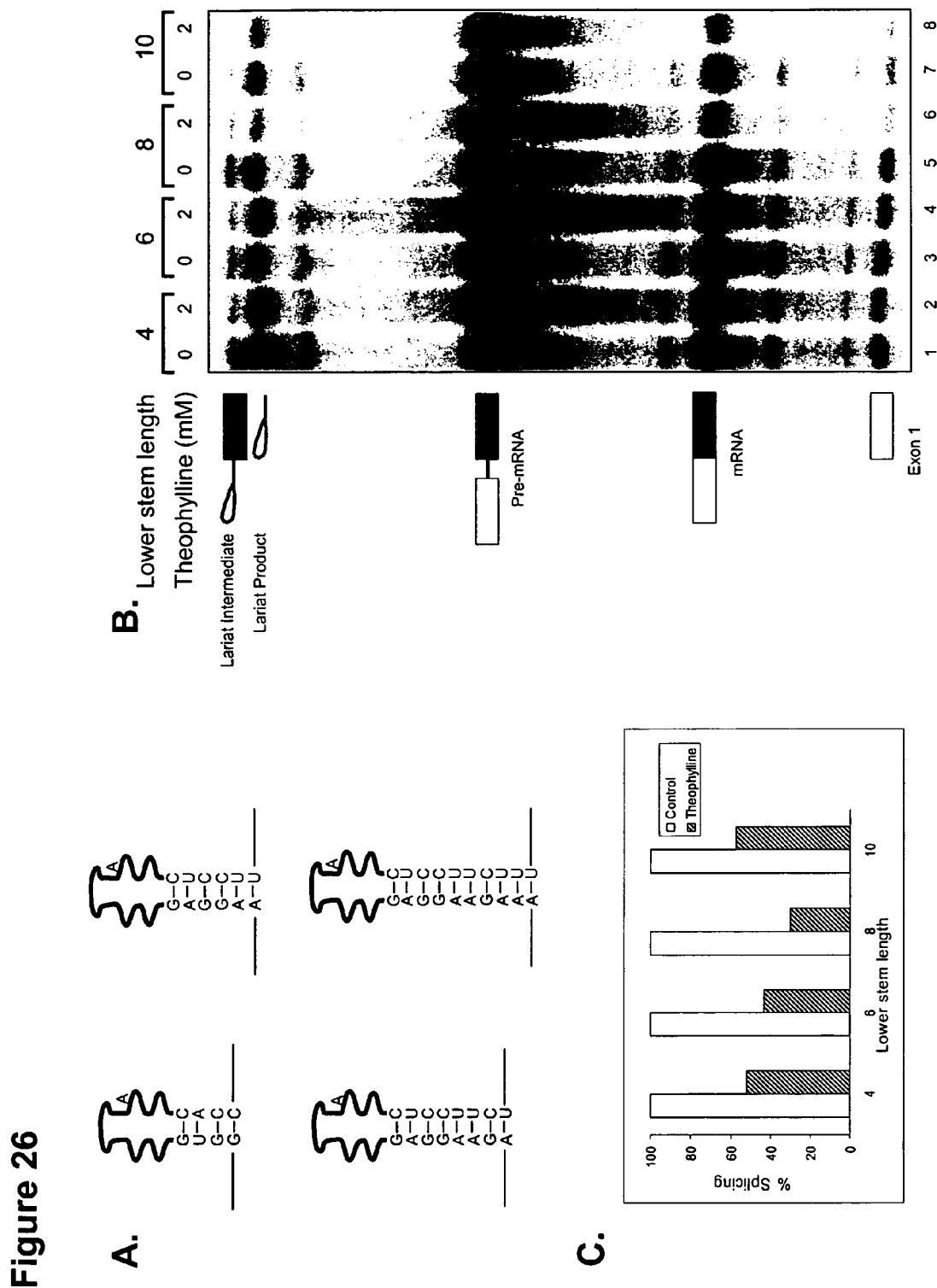
FIG. 26. Thermodynamic stability of the RNA-theophylline complex and splicing inhibition. (A), AdML-Theo15AG derivatives were constructed in which the size of the lower theophylline aptamer stem was varied from four to ten nucleotides. (B), $^{32}$P-labeled pre-mRNAs with stem lengths of four, six, eight, and ten nucleotides were subjected to in vitro splicing in the absence or presence of theophylline by incubating in HeLa nuclear extract. (C), Quantification of data from (B). Inhibition of splicing increased with stem size for the four, six, and eight nucleotide stem pre-mRNAs.

Biochemical and structural studies showed that the lower theophylline aptamer stem is not critical for ligand binding (Zimmermann 1997), but apparently increases the stability of the RNA-theophylline complex. If true, then an increase in the length of the lower theophylline aptamer stem should further stabilize the RNA-theophylline complex, which may bring stronger splicing repression. To test this prediction, AdML-Theo15AG derivatives were constructed in which the size of the lower theophylline aptamer stem was varied from four to ten nucleotides (FIG. 26A). Results showed that the longer the stem size, the stronger the inhibition of splicing (FIGS. 26B and C). A slightly lower degree of inhibition was observed in the case of the substrate with a ten nucleotide stem, apparently due to overall low splicing efficiency in the absence of theophylline.

Figure 27:
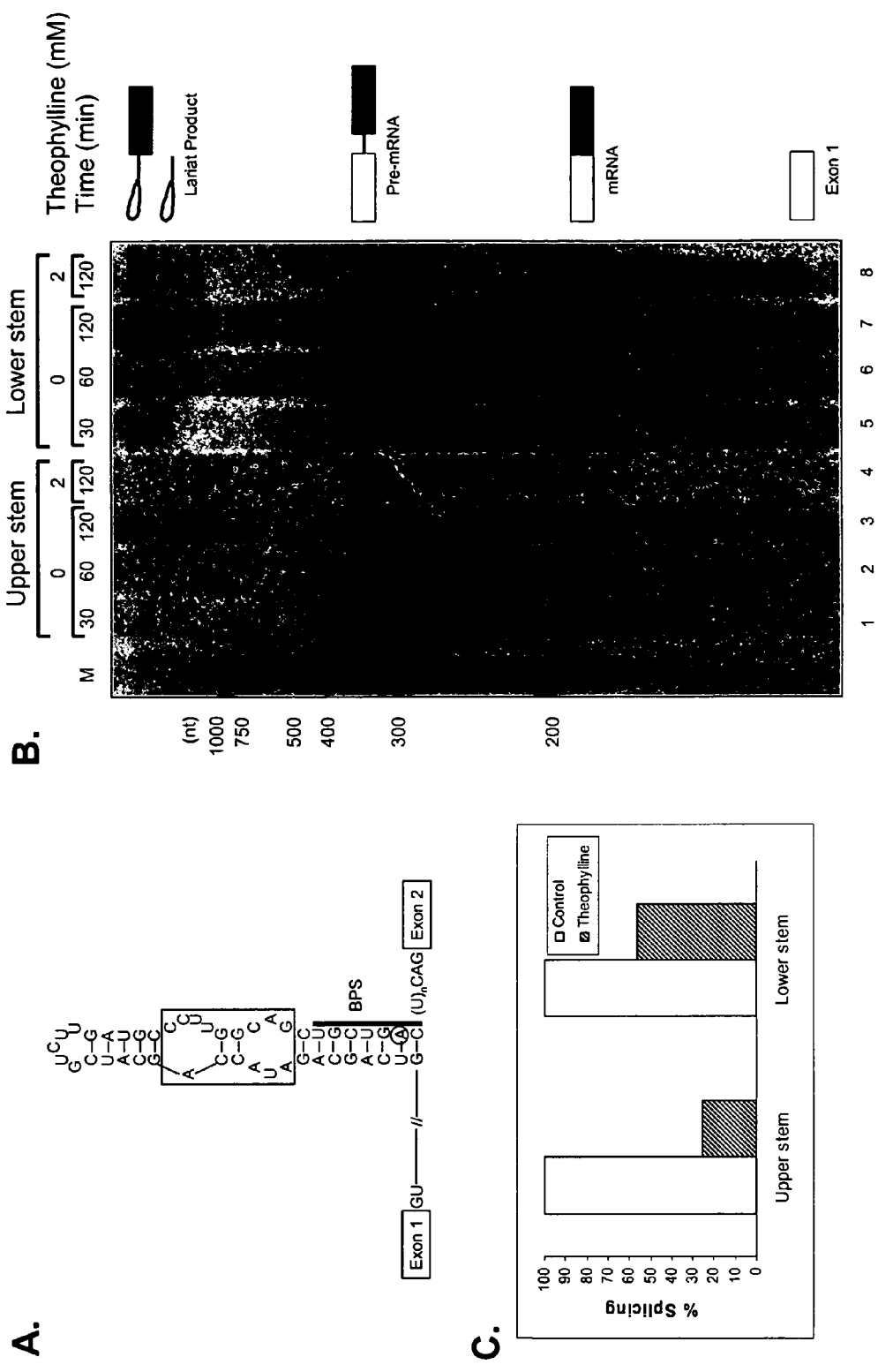
FIG. 27. Location of BPS affects splicing. (A), An AdML derivative was constructed in which the BPS was inserted in the lower theophylline aptamer stem (AdML-lowerBPS, n is 9-15; SEQ ID NO: 29). (B), $^{32}$P-labeled pre-mRNAs with BPS in the lower or upper stem were subjected to in vitro splicing in the absence or presence of theophylline by incubating in HeLa nuclear extract. (C), Quantification of data from (B). Relocation of BPS to the lower stem resulted in an AdML derivative that was less responsive to theophylline-mediated splice repression.

The effect of BPS location on splicing repression was tested next. An AdML derivative in which the BPS was inserted in the lower theophylline aptamer stem was constructed (FIG. 27A). Splicing assays showed that relocation of BPS to the lower stem rendered the AdML derivative less responsive to theophylline-mediated splicing repression (FIG. 27B, compare lane 4 and lane 8). These results are consistent with experiments in which relocation of 3' ss AG from the core to the lower stem resulted in a significantly weaker response to theophylline-mediated splice repression.

Figure 28:
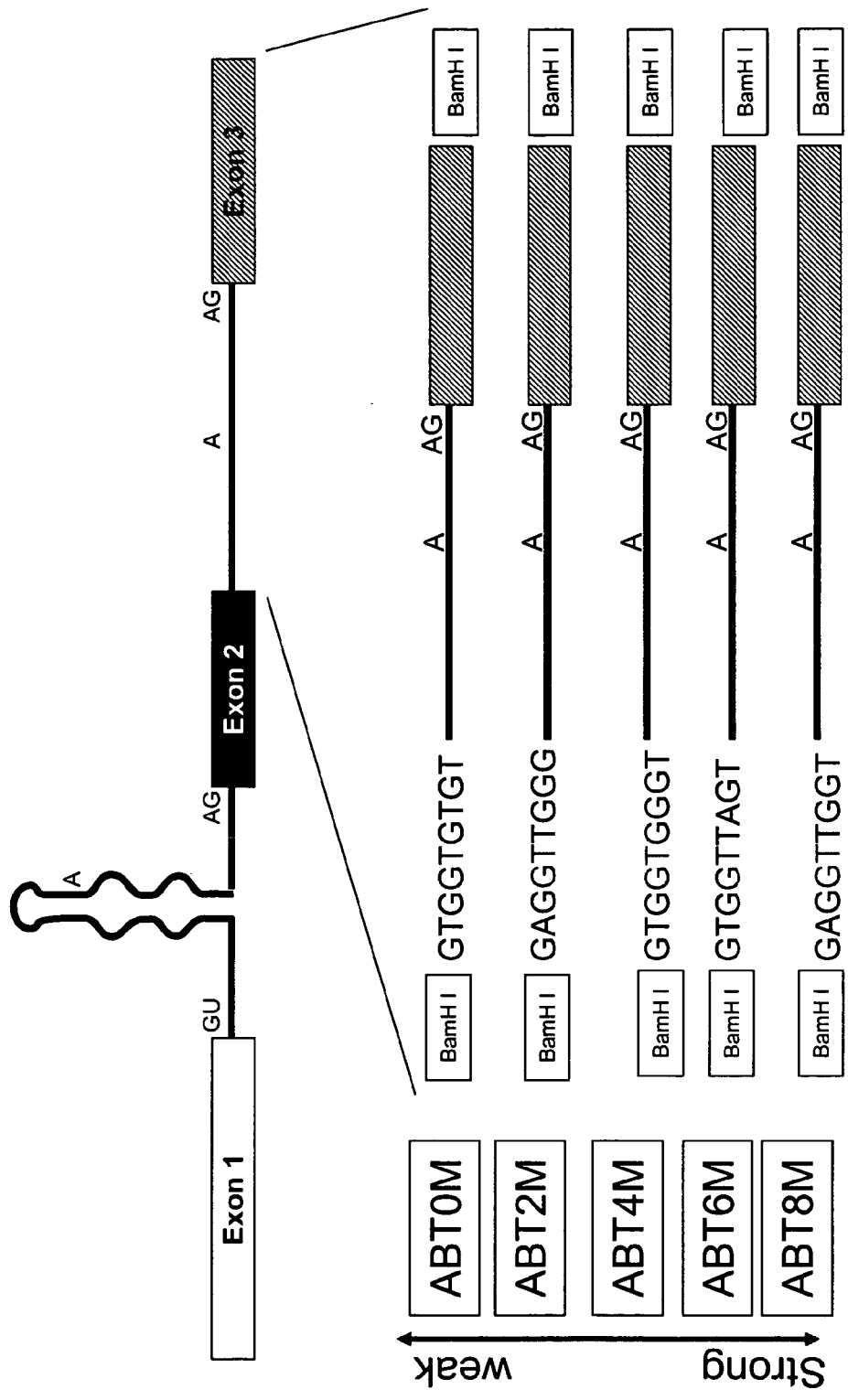
FIG. 28. Schematic representation of alternative splicing substrate. A series of model splicing substrates were constructed consisting of three exons interrupted by two introns. "Strong" and "Weak" refer to the strength of 5' ss in exon 2.
Figure 29:
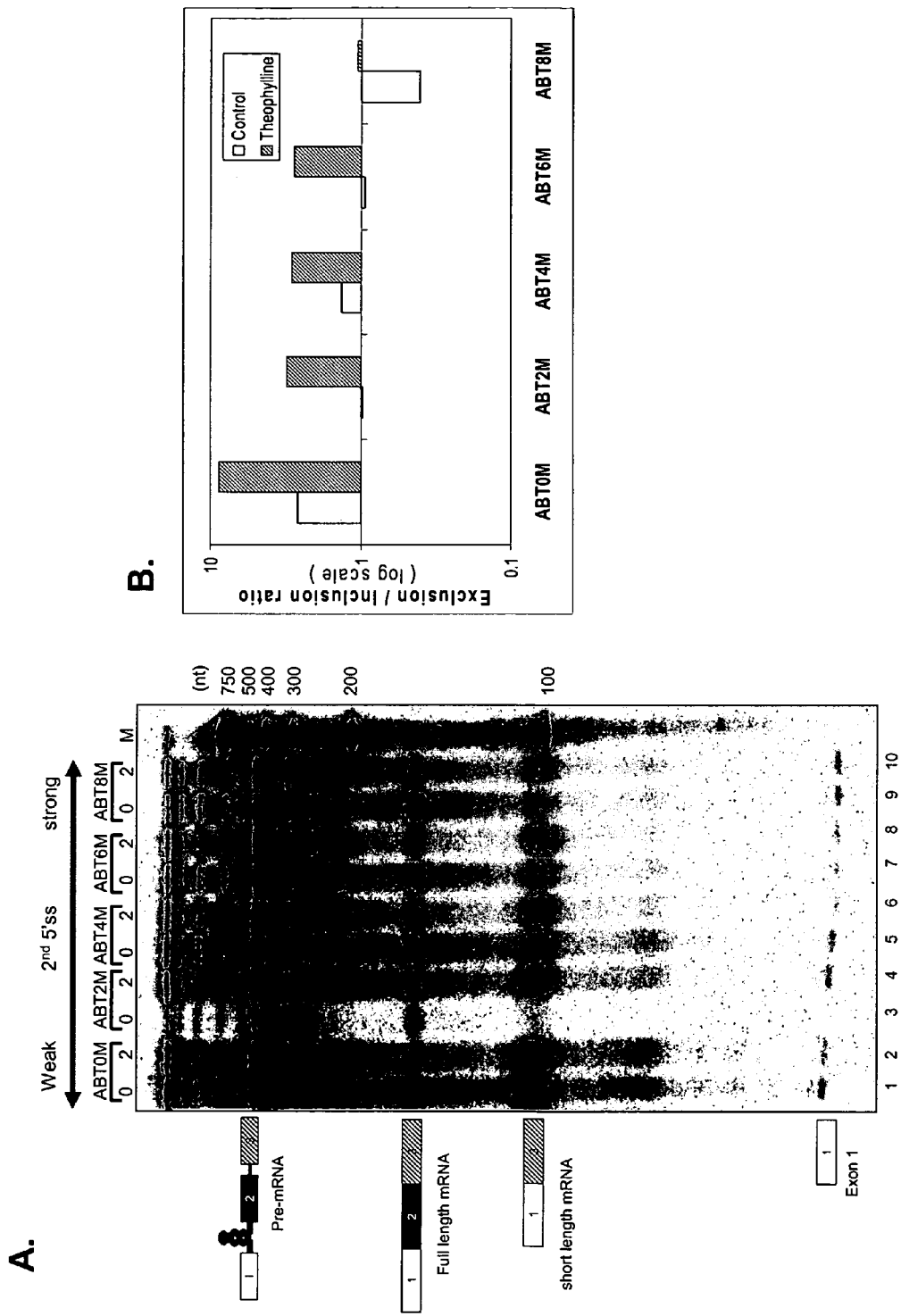
FIG. 29. Theophylline-dependent control of alternative splicing in vitro. (A), $^{32}$P-labeled ABT0M, ABT2M, ABT4M, ABT6M, and ABT8M pre-mRNAs were subjected to in vitro splicing in the absence or presence of theophylline by incubating in HeLa nuclear extract. (B), Quantification of exon 2 exclusion/inclusion in the presence and absence of theophylline.

Naturally-occurring RNA structure elements as well as artificial stem-loop structures are known to influence alternative splicing. To determine whether theophylline-induced secondary structure can likewise influence alternative splicing, a series of model splicing substrates were constructed consisting of three exons interrupted by two introns (FIG. 28). While intron 1 BPS was inserted within TBS, the BPS of intron 2 remained unchanged. The strength of 5' ss in exon 2 increased in the following order: ABT0M<ABT2M<ABT4M<ABT6M<ABT8M. It was hypothesized that in the presence of theophylline, intron 1 branchpoint would be sequestered within the RNA-theophylline complex, which in turn should repress excision of intron 1 and enable intron 2 branchpoint to choose between the 5' ss of exons 1 and 2 for the first step of splicing. Thus, which of the two 5' ss is utilized will determine the level of exon 2 inclusion/exclusion in the full-length mRNA. To test this hypothesis, radioactively labeled ABT0M, ABT2M, ABT4M, ABT6M, and ABT8M were incubated in HeLa nuclear extract under standard conditions for in vitro splicing. Splicing of ABT0M substrate gave rise to two spliced products, a slower migrating band of approximately 150 nucleotides and a smaller band of approximately 100 nucleotides (FIG. 29A). To determine the identity of these mRNAs, representative bands were excised and subjected to RT-PCR followed by DNA sequencing. The sequencing results suggested that the slower migrating band represented full-length mRNA, while the faster migrating band represented mRNA in which exon 2 was missing due to alternative splicing. Significantly, theophylline shifted ABT0M splicing in favor of the short isoform by decreasing the amount of the long isoform (FIG. 29A, compare lanes 1 and 2). Compared to the control, theophylline promoted exon 2 exclusion (FIG. 29B). Results with other substrates suggested an inverse correlation between the strength of exon 2 5' ss and the level of exon 2 skipped mRNA. Thus, splicing of an alternative exon can be fine-tuned in a theophylline-dependent manner.

Figure 30:
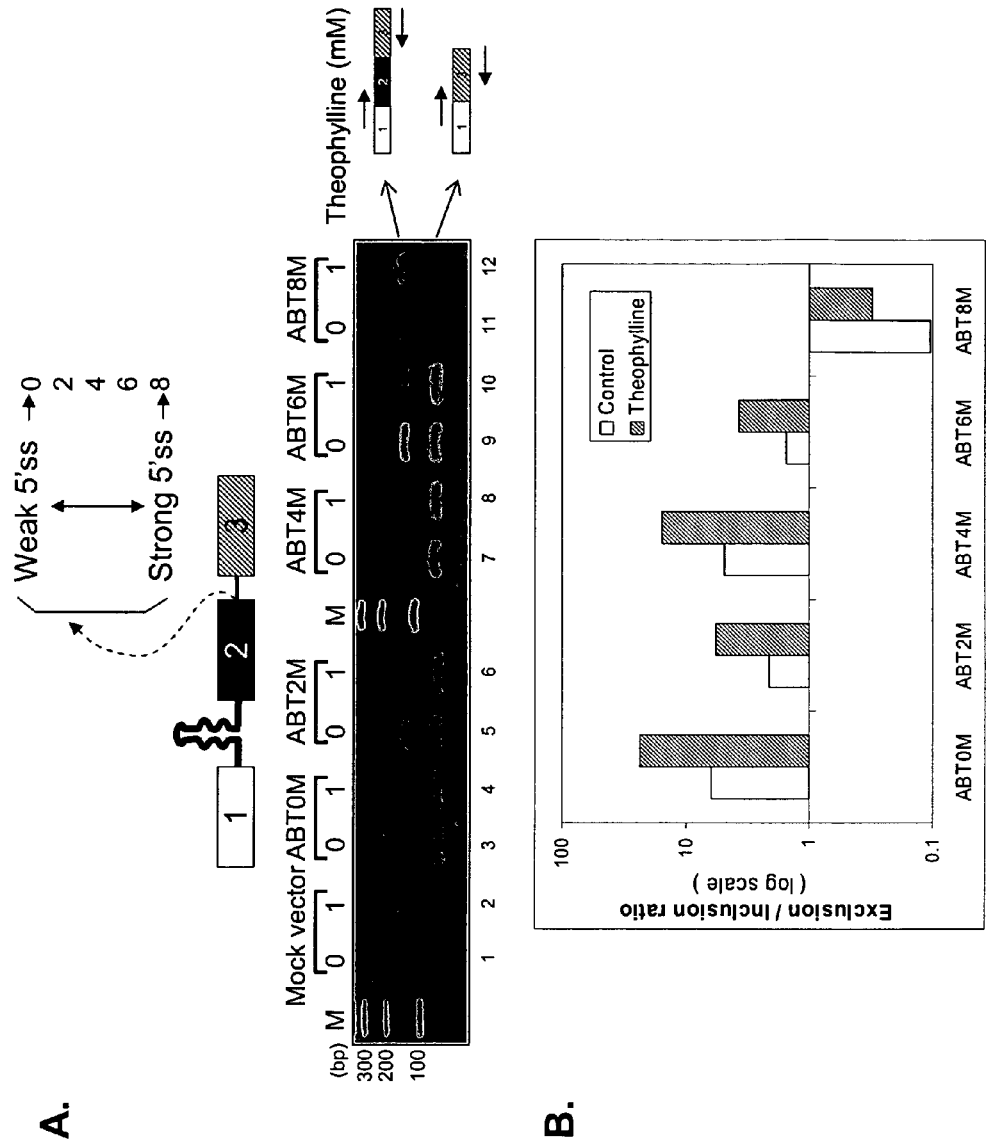
FIG. 30. Theophylline-dependent control of alternative splicing in vitro. (A), HeLa cells were transfected with pcDNA-ABT0-8M constructs in the presence or absence of theophylline. Total RNA was extracted following a 24 hour incubation. (B), Quantification of exon 2 exclusion/inclusion in the presence and absence of theophylline.

To determine whether theophylline-induced sequestering of branchpoint can control splicing in living cells, DNAs that encode ABT0-8M pre-mRNAs was inserted into the mammalian expression vector pcDNA3.1 to yield pcDNA-ABT0-8M. HeLa cells (70-90% confluence) were transiently transfected with these constructs or with empty vector, then treated with theophylline (1 mM) or buffer. After a 24 hour incubation, cells were harvested and total RNA was extracted using an RNeasy mini-kit (Qiagen). RT-PCR assays showed that theophylline can affect alternative splicing (FIG. 30A), which is in agreement with the in vitro results (FIG. 29A). These results suggest that artificial riboswitches can be engineered to regulate alternative splicing both in vitro and in cultured cells.

Alternative splicing is a precisely regulated process by which a single pre-mRNA can undergo differential joining of 5' and 3' splice sites to generate variant mRNAs with diverse, and often antagonistic functions (Black, 2003; Clayerie, 2001; Graveley, 2001). The defective regulation of splice variant expression has been identified as the cause of several genetic disorders (Dredge et al., 2001; Faustino and Cooper, 2003; Garcia-Blanco et al., 2004; Hull et al., 1993; Nissim-Rafinia and Kerem, 2002; Pagani and Baralle, 2004; Phillips and Cooper, 2000). Moreover, certain forms of cancer have been linked to unbalanced isoform expression from genes involved in cell cycle regulation or angiogenesis (Krajewska et al., 1996a; Krajewska et al., 1996b; Novak et al., 2001; Steinman et al., 2004; Venables, 2004; Xerri et al., 1996). Thus, a system based on a small drug like molecule (such as theophylline) that can influence a splicing decision may emerges as novel pharmacological tools with potential for therapeutic intervention.

For example, the theophylline-dependent riboswitches can be employed to target two genes that are linked to human diseases: the Bcl-x gene and the SMN1 gene. Alternative splicing of Bcl-x gene generates a long isoform, Bcl-xL and a short isoform, Bcl-xS. A proper balance between these two isoforms is essential for the normal cell function, such as maintaining breast epithelial cell homeostasis and mammary gland involution. In addition, overexpression of Bcl-xL has been associated with increased risk of breast cancer metastasis and resistance to chemotherapeutic agents. It has been suggested that Bcl-xL promotes cell survival by counteracting signals that lead to the expression of Bcl-xS, a pro-apoptotic protein. An ideal approach for breast cancer treatment would be a conditional splicing switch that regulates Bcl-x trans gene splicing in a dose-dependent manner according to individual patient need.

Figure 31:
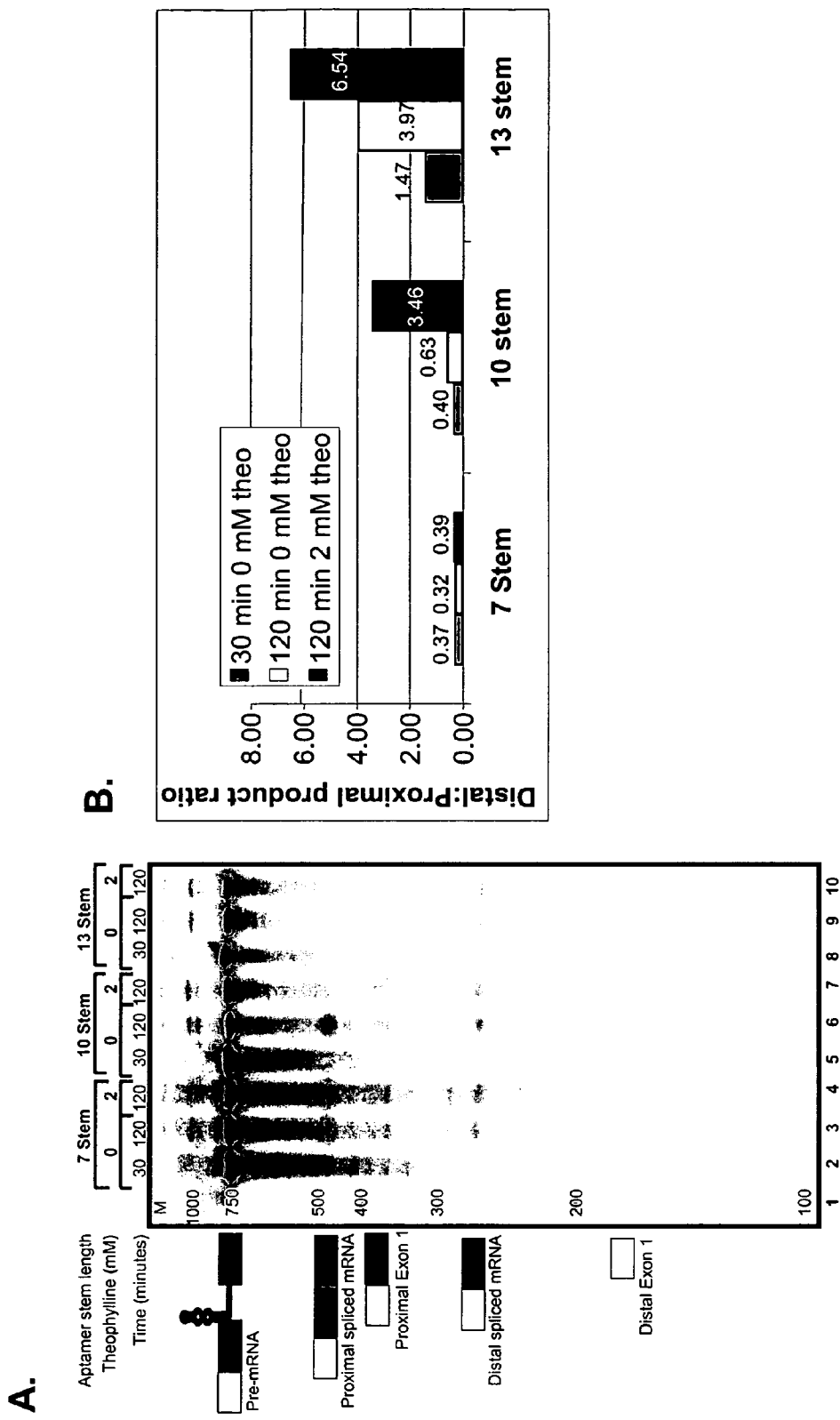
FIG. 31. Controlling Bcl-x pre-mRNA splicing with theophylline. (A), $^{32}$P-labeled BclxSHTheo57 (7 nucleotide stem), BclxSHTheo510 (10 nucleotide stem), and BclxSH-Theo513 (13 nucleotide stem) pre-mRNAs were subjected to in vitro splicing in the absence or presence of theophylline by incubating in HeLa nuclear extract. (B), Quantification of the distal to proximal product ratio in the presence and absence of theophylline.

To investigate whether theophylline can affect alternative splicing of Bcl-x trans gene, a Bcl-x minigene (pBcl-x-Theo) was constructed in which the proximal 5' ss is imbedded within TBS. Because the entire TBS is present in the intron, it was expected that the modified minigene would remain functional. Three derivatives of the Bcl-x minigene were prepared by in vitro transcription: BclxSHTheo57 (7 nucleotide stem), BclxSHTheo510 (10 nucleotide stem), and BclxSHTheo513 (13 nucleotide stem), and used for in vitro splicing assays (FIG. 31A). The distal to proximal product ratio increased in the presence of theophylline in the 10- and 13-nucleotide stem substrates (FIG. 31B). Experiments will next be performed in human breast cancer cells (MFC-7) transfected with the Bcl-x minigene to verify in vivo functionality.

Spinal muscular atrophy (SMA) is a hereditary neurodegenerative disorder, which is caused by mutation in the SMN1 gene (Cartegni et al., 2002; Garcia-Blanco et al., 2004; Khoo et al., 2003). Although SMN2 gene can compensate partially for the loss of SMN1, a translationally silent C-to-T substitution in exon 7 disrupts an SF2/ASF-dependent ESE, resulting into exclusion of exon 7 and production of defective protein. Thus, blocking the 3' splice site (using theophylline aptamer system) of exon 8 may force the splicing machinery to include included exon 7 and therefore produce the functional protein.

EXAMPLES

Example 1

Pre-mRNA Substrates

AdML Par and AdML21AG pre-mRNAs were generated by in vitro transcription using BamHI digested plasmids pAdML Par (Gozani et al., 1994) and pAdML21AG, respectively. AdML-Theo39AG pre-mRNA was synthesized from a PCR derived template, which was amplified from plasmid pAdMLΔAG (Gozani et al., 1994) using T7 primer (5'-TAATACGACTCACTATAG-3'; SEQ ID NO: 30) and oligonucleotide #17179 (5'-TCAACGTCGAGACGCTGC-CAAGGGCCTTTCGGCTG GTATCGCCAGAGAGAGAGG-3'; SEQ ID NO: 31) as forward and reverse primers, respectively. Plasmids encoding AdML-Theo29AG, AdML-Theo27AG and AdML-Theo-Stem21AG pre-mRNAs are derivatives of pAdML (Gozani et al., 1994) and were constructed by PCR using T7 primer as the forward primer and oligonucleotide #17396 (5'-TTGACGTCGACCTCCTGCCAAGGGC-CTTTCGGCTGGTATGAGGAA AAAAAAA-GAAAAAAAGT-3'; SEQ ID NO: 32); oligonucleotide #17395 (5'-TTGACGTCGACCTGCCAAGGGCCTTTCG-GCTGGTATGGAAAAAAAAAGAAAAA AAGT-3'; SEQ ID NO: 33); and oligonucleotide #22735 (5'-TTGACGTC-GATCAGCT GCCAAGGGCCTTTCGGCTGGTATCT-GAAAAAAAAAAGAAAAAGT-3'; SEQ ID NO: 34), respectively as reverse primer. AdML-TheoExon2 pre-mRNA was synthesized from PstI digested plasmid pAdML-TheoExon2, which was generated by PCR using oligonucleotides #30036 (5'-CCCTTGGCAGCGTCTGAGGACAAAC TCTTCGCGG-3'; SEQ ID NO: 35) and #30037 (5'-CCTTTCGGCTGGTATCGCCAC GTCGACCTGAAAAAAAAAG-3'; SEQ ID NO: 36) and pAdML21AG as the template, underline represents theophylline binding sequence. The PCR amplified DNA was circularized using T4 DNA ligase to yield the desired pAdML-TheoExon2.

Example 2

In Vitro Transcription Assay

Linearized plasmid (1 vg) or PCR generated DNA (~150-200 ng) was used as template for run-off transcription. A typical (10 μL) in vitro transcription reaction consisted of 40 mM Tris-HCl (pH 8.0), 2.0 mM spermidine, 10 mM DTT, 20 mM $MgCl_2$, NTP mixture (0.4 mM CTP and ATP, and 0.1 mM GTP and UTP), 2.0 mM cap analog (NEB), ~10 μCi [$\gamma$-$^{32}$P]UTP, 10-20 units SP6 (NEB) or T7 polymerase (Ambion). After incubation at 37° C. for 2 hours, the reaction was terminated by adding 12.5 μL stop buffer and RNA was purified on a 10% denaturing polyacrylamide gel.

Example 3

In Vitro Splicing Assay

Nuclear extracts were prepared from HeLa cells (obtained from National Cell Culture), essentially as described by Dignam et al., (Dignam et al., 1983). To ensure that theophylline binds to its RNA target, a solution (5 μl) consisting of $^{32}$P-labeled pre-mRNA (5-10 fmol, ~10,000 cpm per reaction), indicated concentration of theophylline, 0.5 μl BC300 (20 mM HEPES, pH 8.0, 20% glycerol, 300 mM KCl, 0.2 mM EDTA) and 0.25 μl 160 mM $MgCl_2$ were heated to 65° C. for 5 minutes, followed by 20 minutes incubation at room temperature. Next, 0.5 mM ATP, 20 mM creatine phosphate, 0.4 units of RNasin (Promega), 1.0 mM DTT, 6.25 μl HeLa nuclear extract, and water up to 12.5 μl (all concentrations are final) was added and incubation continued at 30° C. for the indicated time. Where indicated, theophylline was substituted by caffeine or water. Splicing reaction was terminated by the addition of 125 μl stop buffer (100 mM Tris-HCl, pH 7.5, 10 mM EDTA, 1% SDS, 150 mM NaCl, 300 mM sodium acetate) followed by phenol-chloroform extraction and isolation of the RNA by ethanol precipitation. The RNA pallet was washed with 70% aqueous ethanol, dried and dissolved in 10 μl loading buffer. Splicing intermediates and products were analyzed by electrophoresis in 13% denaturing polyacrylamide gels. The fractionated RNAs were visualized by PhosphorImager (Molecular Dynamics) and RNA signals were quantified by ImageQuant version 4.2 software (Molecular Dynamics) or ImageJ version 1.36 software (Rasband, W. S., ImageJ, U.S. National Institutes of Health, Bethesda, Md., http://rsb.info.nih.gov/ij, 1997-2006).

Example 4

Spliceosome Assembly Assay

Spliceosome assembly and separation of individual complexes were performed essentially as described earlier (Das and Reed, 1999). Briefly, pre-mRNA (~5 ng) was incubated in HeLa nuclear extract in the absence or presence of theophylline (12.5 μl total volume) under the conditions that support in vitro splicing. After the incubation, 2.5 μl of 4 μg/μl heparin and 2.5 μl of 5× loading dye containing 1×TBE (89 mM Tris, 89 mM boric acid, 2.5 mM EDTA), 20% glycerol, 0.25% bromophenol blue, 0.25% xylene cyanol) was added and the 3 μl aliquots of each reaction mixture were loaded on a 2% horizontal low-melting agarose gels followed by the spliceosome complexes at 70V for 3 h in Tris-glycine running buffer at room temperature (Konarska and Sharp, 1986). Gels were fixed in 10% acetic acid, 10% methanol for 30 min, and then dried under vacuum at 80° C.

As stated above, the foregoing is merely intended to illustrate various embodiments of the present invention. The specific modifications discussed above are not to be construed as limitations on the scope of the invention. It will be apparent to one skilled in the art that various equivalents, changes, and modifications may be made without departing from the scope of the invention, and it is understood that such equivalent embodiments are to be included herein. All references cited herein are expressly incorporated by reference herein in their entirety.

REFERENCES

1. Aebi, M., Hornig, H., Padgett, R. A., Reiser, J. and Weissmann, C. (1986) Sequence requirements for splicing of higher eukaryotic nuclear pre-mRNA. Cell, 47, 555-565.
2. Aurup, H., Williams, D. and Eckstein, F. (1992) 2'-Fluoro- and 2'-amino-2'-deoxynucleoside 5'-triphosphates as substrates for T7 RNA polymerase. Biochemistry, 31, 9636-9641.
3. Banerjee, H., Rahn, A., Davis, W. and Singh, R. (2003) Sex lethal and U2 small nuclear ribonucleoprotein auxiliary factor (U2AF65) recognize polypyrimidine tracts using multiple modes of binding. Rna, 9, 88-99.
4. Belshaw, P. J., Ho, S. N., Crabtree, G. R. and Schreiber, S. L. (1996) Controlling protein association and subcellular localization with a synthetic ligand that induces heterodimerization of proteins. Proc Natl Acad Sci USA, 93, 4604-4607.
5. Bevers, S., Ha, S. B. and McLaughlin, L. W. (1999) Critical nature of a specific uridine O2-carbonyl for cleavage by the hammerhead ribozyme. Biochemistry, 38, 7710-7718.
6. Black, D. L. (2003) Mechanisms of alternative pre-messenger RNA splicing. Annu Rev Biochem, 72, 291-336.
7. Boggs, R. T., Gregor, P., Idriss, S., Belote, J. M. and McKeown, M. (1987) Regulation of sexual differentiation in D. melanogaster via alternative splicing of RNA from the transformer gene. Cell, 50, 739-747.
8. Bunch, T. A., Grinblat, Y. and Goldstein, L. S. (1988) Characterization and use of the Drosophila metallothionein promoter in cultured Drosophila melanogaster cells. Nucleic Acids Res, 16, 1043-1061.
9. Buratti, E., Muro, A. F., Giombi, M., Gherbassi, D., Iaconcig, A. and Baralle, F. E. (2004) RNA folding affects the recruitment of SR proteins by mouse and human polypurinic enhancer elements in the fibronectin EDA exon. Mol Cell Biol, 24, 1387-1400.
10. Burgstaller, P. and Famulok, M. (1994) Isolation of RNA aptamers for biological cofactors by in vitro selection. Angew. Chem. Int. Ed. Engl., 33, 1084-1087.
11. Cartegni, L. and Krainer, A. R. (2003) Correction of disease-associated exon skipping by synthetic exon-specific activators. Nat Struct Biol, 10, 120-125.
12. Chen, Z., Monia, B. P. and Corey, D. R. (2002) Telomerase inhibition, telomere shortening, and decreased cell proliferation by cell permeable 2'-O-methoxyethyl oligonucleotides. J Med Chem, 45, 5423-5425.
13. Chiara, M. D., Palandjian, L., Feld Kramer, R. and Reed, R. (1997) Evidence that U5 snRNP recognizes the 3' splice site for catalytic step II in mammals. Embo J, 16, 4746-4759.

14. Chua, K. and Reed, R. (2001) An upstream AG determines whether a downstream AG is selected during catalytic step II of splicing. Mol Cell Biol, 21, 1509-1514.
15. Clayerie, J. M. (2001) Gene number. What if there are only 30,000 human genes? Science, 291, 1255-1257.
16. Cline, T. W. and Meyer, B. J. (1996) Vive la difference: males vs females in flies vs worms. Annu Rev Genet, 30, 637-702.
17. Collins, C. A. and Guthrie, C. (1999) Allele-specific genetic interactions between Prp8 and RNA active site residues suggest a function for Prp8 at the catalytic core of the spliceosome. Genes Dev, 13, 1970-1982.
18. Collins, C. A. and Guthrie, C. (2001) Genetic interactions between the 5' and 3' splice site consensus sequences and U6 snRNA during the second catalytic step of pre-mRNA splicing. RNA, 7, 1845-1854.
19. Das, R. and Reed, R. (1999) Resolution of the mammalian E complex and the ATP-dependent spliceosomal complexes on native agarose mini-gels. Rna, 5, 1504-1508.
20. Deirdre, A., Scadden, J. and Smith, C. W. (1995) Interactions between the terminal bases of mammalian introns are retained in inosine-containing pre-mRNAs. Embo J, 14, 3236-3246.
21. Dignam, J. D., Lebovitz, R. M. and Roeder, R. G. (1983) Accurate transcription initiation by RNA polymerase II in a soluble extract from isolated mammalian nuclei. Nucleic Acids Res., 11, 1475-1489.
22. Dominski, Z. and Kole, R. (1993) Restoration of correct splicing in thalassemic pre-mRNA by antisense oligonucleotides. Proc Natl Acad Sci USA, 90, 8673-8677.
23. Dredge, B. K., Polydorides, A. D. and Darnell, R. B. (2001) The splice of life: alternative splicing and neurological disease. Nat Rev Neurosci, 2, 43-50.
24. Duconge, F. and Toulme, J. J. (1999) In vitro selection identifies key determinants for loop-loop interactions: RNA aptamers selective for the TAR RNA element of HIV-1. Rna, 5, 1605-1614.
25. Eder, P. S., DeVine, R. J., Dagle, J. M. and Walder, J. A. (1991) Substrate specificity and kinetics of degradation of antisense oligonucleotides by a 3' exonuclease in plasma. Antisense Res Dev, 1, 141-151.
26. Endo, M., Mitsui, T., Okuni, T., Kimoto, M., Hirao, I. and Yokoyama, S. (2004) Unnatural base pairs mediate the site-specific incorporation of an unnatural hydrophobic component into RNA transcripts. Bioorg Med Chem Lett, 14, 2593-2596.
27. Eperon, I. C. and Muntoni, F. (2003) Can a 'patch' in a skipped exon make the pre-mRNA splicing machine run better? Trends Mol Med, 9, 233-234.
28. Eperon, L. P., Graham, I. R., Griffiths, A. D. and Eperon, I. C. (1988) Effects of RNA secondary structure on alternative splicing of pre-mRNA: is folding limited to a region behind the transcribing RNA polymerase? Cell, 54, 393-401.
29. Faustino, N. A. and Cooper, T. A. (2003) Pre-mRNA splicing and human disease. Genes Dev, 17, 419-437.
30. Freyer, G. A., Arenas, J., Perkins, K. K., Furneaux, H. M., Pick, L., Young, B., Roberts, R. J. and Hurwitz, J. (1987) In vitro formation of a lariat structure containing a G2'-5'G linkage. J Biol Chem., 262, 4267-4273.
31. Garcia-Blanco, M. A., Baraniak, A. P. and Lasda, E. L. (2004) Alternative splicing in disease and therapy. Nat Biotechnol, 22, 535-546.
32. Gaur, R. K., McLaughlin, L. W. and Green, M. R. (1997) Functional group substitutions of the branchpoint adenosine in a nuclear pre-mRNA and a group II intron. Rna, 3, 861-869.
33. Gaur, R. K., Valcarcel, J. and Green, M. R. (1995) Sequential recognition of the pre-mRNA branch point by U2AF65 and a novel spliceosome-associated 28-kDa protein. RNA, 1, 407-417.
34. Goguel, V. and Rosbash, M. (1993) Splice site choice and splicing efficiency are positively influenced by pre-mRNA intramolecular base pairing in yeast. Cell, 72, 893-901.
35. Goguel, V., Wang, Y. and Rosbash, M. (1993) Short artificial hairpins sequester splicing signals and inhibit yeast pre-mRNA splicing. Mol. Cell. Biol., 13, 6841-6848.
36. Goodall, G. J. and Filipowicz, W. (1991) Different effects of intron nucleotide composition and secondary structure on pre-mRNA splicing in monocot and dicot plants. Embo J, 10, 2635-2644.
37. Gottesfeld, J. M., Neely, L., Trauger, J. W., Baird, E. E. and Dervan, P. B. (1997) Regulation of gene expression by small molecules. Nature, 387, 202-205.
38. Gozani, O., Patton, J. G. and Reed, R. (1994) A novel set of spliceosome-associated proteins and the essential splicing factor PSF bind stably to pre-mRNA prior to catalytic step II of the splicing reaction. Embo J, 13, 3356-3367.
39. Granadino, B., Penalva, L. O., Green, M. R., Valcarcel, J. and Sanchez, L. (1997) Distinct mechanisms of splicing regulation in vivo by the *Drosophila* protein Sex-lethal. Proc. Natl. Acad. Sci. USA, 94, 7343-7348.
40. Graveley, B. R. (2001) Alternative splicing: increasing diversity in the proteomic world. Trends Genet, 17, 100-107.
41. Graveley, B. R. (2005) Small molecule control of pre-mRNA splicing. Rna, 11, 355-358.
42. Guschlbauer, W. (1980) Conformational analysis of ribonucleosides from proton-proton coupling constants. Biochim Biophys Acta, 610, 47-55.
43. Heidenreich, O., Benseler, F., Fahrenholz, A. and Eckstein, F. (1994) High activity and stability of hammerhead ribozymes containing 2'-modified pyrimidine nucleosides and phosphorothioates. J Biol Chem, 269, 2131-2138.
44. Heidenreich, O., Kang, S. H., Xu, X. and Nerenberg, M. (1995) Application of antisense technology to therapeutics. Mol Med Today, 1, 128-133.
45. Ho, S. N., Biggar, S. R., Spencer, D. M., Schreiber, S. L. and Crabtree, G. R. (1996) Dimeric ligands define a role for transcriptional activation domains in reinitiation. Nature, 382, 822-826.
46. Hornig, H., Aebi, M. and Weissmann, C. (1986) Effect of mutations at the lariat branch acceptor site on beta-globin pre-mRNA splicing in vitro. Nature, 324, 589-591.
47. Huang, Z. and Szostak, J. W. (2003) Evolution of aptamers with a new specificity and new secondary structures from an ATP aptamer. Rna, 9, 1456-1463.
48. Hull, J., Shackleton, S. and Harris, A. (1993) Abnormal mRNA splicing resulting from three different mutations in the CFTR gene. Hum Mol Genet, 2, 689-692.
49. Inoue, K., Hoshijima, K., Sakamoto, H. and Shimura, Y. (1990) Binding of the *Drosophila* sex-lethal gene product to the alternative splice site of transformer primary transcript. Nature, 344, 461-463.
50. Jenison, R. D., Gill, S. C., Pardi, A. and Polisky, B. (1994) High-resolution molecular discrimination by RNA. Science, 263, 1425-1429.
51. Johnson, J. M., Castle, J., Garrett-Engele, P., Kan, Z., Loerch, P. M., Armour, C. D., Santos, R., Schadt, E. E., Stoughton, R. and Shoemaker, D. D. (2003) Genome-wide survey of human alternative pre-mRNA splicing with exon junction microarrays. Science, 302, 2141-2144.
52. Joyce, G. F. (1994) In vitro evolution of nucleic acids. Curr Opin Struct Biol, 4, 331-336.

53. Kan, Z., Rouchka, E. C., Gish, W. R. and States, D. J. (2001) Gene structure prediction and alternative splicing analysis using genomically aligned ESTs. Genome Res, 11, 889-900.

54. Kandels-Lewis, S, and Seraphin, B. (1993) Involvement of U6 snRNA in 5' splice site selection. Science, 262, 2035-2039.

55. Kawasaki, A. M., Casper, M. D., Freier, S. M., Lesnik, E. A., Zounes, M. C., Cummins, L. L., Gonzalez, C. and Cook, P. D. (1993) Uniformly modified 2'-deoxy-2'-fluoro phosphorothioate oligonucleotides as nuclease-resistant antisense compounds with high affinity and specificity for RNA targets. J. Med. Chemistry, 36, 831-841.

56. Konarska, M. M. and Sharp, P. A. (1986) Electrophoretic separation of complexes involved in the splicing of precursors to mRNAs. Cell, 46, 845-855.

57. Konforti, B. B., Koziolkiewicz, M. J. and Konarska, M. M. (1993) Disruption of base pairing between the 5' splice site and the 5' end of U1 snRNA is required for spliceosome assembly. Cell, 75, 863-873.

58. Krainer, A. R., Maniatis, T., Ruskin, B. and Green, M. R. (1984) Normal and mutant human beta-globin pre-mRNAs are faithfully and efficiently spliced in vitro. Cell, 36, 993-1005.

59. Krajewska, M., Fenoglio-Preiser, C. M., Krajewski, S., Song, K., Macdonald, J. S., Stemmerman, G. and Reed, J. C. (1996a) Immunohistochemical analysis of Bcl-2 family proteins in adenocarcinomas of the stomach. Am J Pathol, 149, 1449-1457.

60. Krajewska, M., Krajewski, S., Epstein, J. I., Shabaik, A., Sauvageot, J., Song, K., Kitada, S, and Reed, J. C. (1996b) Immunohistochemical analysis of bcl-2, bax, bcl-X, and mcl-1 expression in prostate cancers. Am J Pathol, 148, 1567-1576.

61. Kramer, A. (1996) The structure and function of proteins involved in mammalian pre-mRNA splicing. Annu Rev Biochem, 65, 367-409.

62. Kubik M F, B. C., Fitzwater T, Watson S R, Tasset D M. (1997) Isolation and characterization of 2'-fluoro-, 2'-amino-, and 2'-fluoro-/amino-modified RNA ligands to human IFN-gamma that inhibit receptor binding. J Immunol, 159.

63. Kurreck, J. (2003) Antisense technologies. Improvement through novel chemical modifications. Eur J Biochem, 270, 1628-1644.

64. Kuwabara, T., Warashina, M., Tanabe, T., Tani, K., Asano, S, and Taira, K. (1998) A novel allosterically trans-activated ribozyme, the maxizyme, with exceptional specificity in vitro and in vivo. Mol Cell, 2, 617-627.

65. Kuznetsova, M., Novopashina, D., Repkova, M., Venyaminova, A. and Vlassov, V. (2004) Binary hammerhead ribozymes with high cleavage activity. Nucleosides Nucleotides Nucleic Acids, 23, 1037-1042.

66. Lamond, A. I., Konarska, M. M. and Sharp, P. A. (1987) A mutational analysis of spliceosome assembly: evidence for splice site collaboration during spliceosome formation. Genes Dev., 1, 532-543.

67. Lesser, C. and Guthrie, C. (1993) Mutations in U6 snRNA that alter splice site specificity: implications for the active site. Science, 262, 1982-1988.

68. Lian, Y. and Garner, H. R. (2005) Evidence for the regulation of alternative splicing via complementary DNA sequence repeats. Bioinformatics, 21, 1358-1364.

69. Liu, H.-K., Goodall, G. J., Kole, R. and Filipowicz, W. (1995) Effects of secondary structure on pre-mRNA splicing: hairpins sequestering the 5' but not the 3' splice site inhibit intron processing in *Nicotiana plumbaginifolia*. EMBO J., 14, 377-388.

70. Liu, Z. R., Laggerbauer, B., Luhrmann, R. and Smith, C. W. (1997) Crosslinking of the U5 snRNP-specific 116-kDa protein to RNA hairpins that block step 2 of splicing. Rna, 3, 1207-1219.

71. Lopez, A. J. (1998) Alternative splicing of pre-mRNA: developmental consequences and mechanisms of regulation. Annu Rev Genet, 32, 279-305.

72. Luukkonen, B. G. and Seraphin, B. (1997) The role of branchpoint-3' splice site spacing and interaction between intron terminal nucleotides in 3' splice site selection in *Saccharomyces cerevisiae*. Embo J, 16, 779-792.

73. Malca, H., Shomron, N. and Ast, G. (2003) The U1 snRNP base pairs with the 5' splice site within a penta-snRNP complex. Mol Cell Biol, 23, 3442-3455.

74. Maniatis, T. and Tasic, B. (2002) Alternative pre-mRNA splicing and proteome expansion in metazoans. Nature, 418, 236-243.

75. Marshall, K. A. and Ellington, A. D. (2000) In vitro selection of RNA aptamers. Methods Enzymol, 318, 193-214.

76. Merendino, L., Guth, S., Bilbao, D., Martinez, C. and Valcarcel, J. (1999) Inhibition of msl-2 splicing by Sex-lethal reveals interaction between U2AF35 and the 3' splice site AG. Nature, 402, 838-841.

77. Mironov, A. A., Fickett, J. W. and Gelfand, M. S. (1999) Frequent alternative splicing of human genes. Genome Res, 9, 1288-1293.

78. Modrek, B., Resch, A., Grasso, C. and Lee, C. (2001) Genome-wide detection of alternative splicing in expressed sequences of human genes. Nucleic Acids Res, 29, 2850-2859.

79. Monia, B. P., Lesnik, E. A., Gonzalez, C., Lima, W. F., McGee, D., Guinosso, C. J., Kawasaki, A. M., Cook, P. D. and Freier, S. M. (1993) Evaluation of 2'-modified oligonucleotides containing 2'-deoxy gaps as antisense inhibitors of gene expression. J Biol Chem, 268, 14514-14522.

80. Moore, J. J., Query, C. C. and Sharp, P. A. (1993) Splicing of precursors to mRNA by the spliceosome. In Gesteland, R. F. and Atkins, J. R. (eds.), In The RNA world. Cold Spring Harbor, N.Y.

81. Moore, M. J. and Sharp, P. A. (1992) Site-specific modification of pre-mRNA: the 2'-hydroxyl groups at the splice sites. Science, 256, 992-997.

82. Newman, A. (1994) Activity in the spliceosome. Curr. Biol., 4, 462-464.

83. Newman, A. J., Lin, R. J., Cheng, S. C. and Abelson, J. (1985) Molecular consequences of specific intron mutations on yeast mRNA splicing in vivo and in vitro. Cell, 42, 335-344.

84. Nilsen, T. W. (2003) The spliceosome: the most complex macromolecular machine in the cell? Bioessays, 25, 1147-1149.

85. Nissim-Rafinia, M. and Kerem, B. (2002) Splicing regulation as a potential genetic modifier. Trends Genet, 18, 123-127.

86. Novak, U., Grob, T. J., Baskaynak, G., Peters, U. R., Aebi, S., Zwahlen, D., Tschan, M. P., Kreuzer, K. A., Leibundgut, E. O., Cajot, J. F., Tobler, A. and Fey, M. F. (2001) Overexpression of the p73 gene is a novel finding in high-risk B-cell chronic lymphocytic leukemia. Ann Oncol, 12, 981-986.

87. Nudler, E. and Mironov, A. S. (2004) The riboswitch control of bacterial metabolism. Trends Biochem Sci, 29, 11-17.

88. Pagani, F. and Baralle, F. E. (2004) Genomic variants in exons and introns: identifying the splicing spoilers. Nat Rev Genet, 5, 389-396.
89. Parker, R. and Siliciano, P. G. (1993) Evidence for an essential non-Watson-Crick interaction between the first and last nucleotides of a nuclear pre-mRNA intron. Nature, 361, 660-662.
90. Patterson, B. and Guthrie, C. (1991) A U-rich tract enhances usage of an alternative 3' splice site in yeast. Cell, 64, 181-187.
91. Phillips, A. and Cooper, T. (2000) RNA processing and human disease. Cell Mol Life Sci, 57, 235-249.
92. Pieken, W. A., Olsen, D. B., Benseler, F., Aurup, H. and Eckstein, F. (1991) Kinetic characterization of ribonuclease-resistant 2'-modified hammerhead ribozymes. Science, 253, 314-317.
93. Proctor, D. J., Ma, H., Kierzek, E., Kierzek, R., Gruebele, M. and Bevilacqua, P. C. (2004) Folding thermodynamics and kinetics of YNMG RNA hairpins: specific incorporation of 8-bromoguanosine leads to stabilization by enhancement of the folding rate. Biochemistry, 43, 14004-14014.
94. Query, C. C., Moore, M. J. and Sharp, P. A. (1994) Branch nucleophile selection in pre-mRNA splicing: evidence for the bulged duplex model. Genes & Dev., 8, 587-597.
95. Reed, R. and Palandjian, L. (1997) Spliceosome assembly. In Krainer, A. (ed.), Eukaryotic mRNA processing. IRL Press, Oxford, pp. 103-129.
96. Roberts, G. C. and Smith, C. W. (2002) Alternative splicing: combinatorial output from the genome. Curr Opin Chem Biol, 6, 375-383.
97. Ruskin, B. and Green, M. R. (1985) Role of the 3' splice site consensus sequence in mammalian pre-mRNA splicing. Nature, 317, 732-734.
98. Ruskin, B., Zamore, P. D. and Green, M. R. (1988) A factor, U2AF, is required for U2 snRNP binding and splicing complex assembly. Cell, 52, 207-219. Ryner, L. C. and Baker, B. S. (1991) Regulation of doublesex pre-mRNA processing by 3' splice site activation. Genes Dev., 5, 2071-2085.
99. Sakamoto, H., Inoue, K., Higuchi, I., Ono, Y. and Shimura, Y. (1992) Control of *Drosophila* Sex-lethal pre-mRNA splicing by its own female-specific product. Nucleic Acids Res, 20, 5533-5540.
100. Sambrook, J., and Russell, D. W. 2001. Molecular cloning: a laboratory manual, 3rd ed., Cold Spring Harbor Laboratory Press, Cold Spring Harbor, N.Y.
101. Sassanfar, M. and Szostak, J. W. (1993) An RNA motif that binds ATP. Nature, 364, 550-553.
102. Sawa, H. and Abelson, J. (1992) Evidence for a base-pairing interaction between U6 small nuclear RNA and the 5' splice site during the splicing reaction in yeast. Proc. Natl. Acad. Sci. USA, 89, 11269-11273.
103. Sawa, H. and Shimura, Y. (1992) Association of U6 snRNA with the 5'-splice site region of pre-mRNA in the spliceosome. Genes & Dev., 6, 244-254.
104. Seraphin, B., Kretzner, L. and Rosbash, M. (1988) A U1 snRNA:pre-mRNA base pairing interaction is required early in yeast spliceosome assembly but does not uniquely define the 5' cleavage site. EMBO J., 7, 2533-2538.
105. Seraphin, B. and Rosbash, M. (1990) Exon mutations uncouple 5' splice site selection from U1 snRNA pairing. Cell, 63, 619-629.
106. Shaw, J. P., Kent, K., Bird, J., Fishback, J. and Froehler, B. (1991) Modified deoxyoligonucleotides stable to exonuclease degradation in serum. Nucleic Acids Res, 19, 747-750.
107. Shomron, N. and Ast, G. (2003) Boric acid reversibly inhibits the second step of pre-mRNA splicing. FEBS Lett, 552, 219-224.
108. Shomron, N., Malca, H., Vig, I. and Ast, G. (2002) Reversible inhibition of the second step of splicing suggests a possible role of zinc in the second step of splicing. Nucleic Acids Res, 30, 4127-4137.
109. Siliciano, P. G. and Guthrie, C. (1988) 5' splice site selection in yeast: genetic alterations in base-pairing with U1 reveal additional requirements. Genes Dev., 2, 1258-1267.
110. Singh, R., Banerjee, H. and Green, M. R. (2000) Differential recognition of the polypyrimidine-tract by the general splicing factor U2AF65 and the splicing repressor sex-lethal. Rna, 6, 901-911.
111. Singh, R., Valcarcel, J. and Green, M. R. (1995) Distinct binding specificities and functions of higher eukaryotic polypyrimidine tract-binding proteins. Science, 268, 1173-1176.
112. Skordis, L. A., Dunckley, M. G., Yue, B., Eperon, I. C. and Muntoni, F. (2003) Bifunctional antisense oligonucleotides provide a trans-acting splicing enhancer that stimulates SMN2 gene expression in patient fibroblasts. Proc Natl Acad Sci USA, 100, 4114-4119.
113. Smith, C. W. and Valcarcel, J. (2000) Alternative pre-mRNA splicing: the logic of combinatorial control. Trends Biochem Sci, 25, 381-388.
114. Solnick, D. (1985) Alternative splicing caused by RNA secondary structure. Cell, 43, 667-676.
115. Sontheimer, E. and Steitz, J. A. (1993) The U5 and U6 small nuclear RNAs as active site components of the spliceosome. Science, 262, 1989-1996.
116. Sosnowski, B. A., Belote, J. M. and McKeown, M. (1989) Sex-specific alternative splicing of RNA from the transformer gene results from sequence-dependent splice site blockage. Cell, 58, 449-459.
117. Soukup, G. A. and Breaker, R. R. (1999a) Engineering precision RNA molecular switches. Proc Natl Acad Sci USA, 96, 3584-3589.
118. Soukup, G. A. and Breaker, R. R. (1999b) Nucleic acid molecular switches. Trends Biotechnol, 17, 469-476.
119. Soukup, G. A., Emilsson, G. A. and Breaker, R. R. (2000) Altering molecular recognition of RNA aptamers by allosteric selection. J Mol Biol, 298, 623-632.
120. Staley, J. P. and Guthrie, C. (1998) Mechanical devices of the spliceosome: motors, clocks, springs, and things. Cell, 92, 315-326.
121. Steinman, H. A., Burstein, E., Lengner, C., Gosselin, J., Pihan, G., Duckett, C. S. and Jones, S. N. (2004) An alternative splice form of Mdm2 induces p53-independent cell growth and tumorigenesis. J Biol Chem, 279, 4877-4886.
122. Stevens, S. W., Ryan, D. E., Ge, H. Y., Moore, R. E., Young, M. K., Lee, T. D. and Abelson, J. (2002) Composition and functional characterization of the yeast spliceosomal penta-snRNP. Mol Cell, 9, 31-44.
123. Tanaka, K., Watakabe, A. and Shimura, Y. (1994) Polypurine sequences within a downstream exon function as a splicing factor. Mol. Cell. Biol., 14, 1347-1354.
124. Thanaraj, T. A., Stamm, S., Clark, F., Riethoven, J. J., Le Texier, V. and Muilu, J. (2004) ASD: the Alternative Splicing Database. Nucleic Acids Res, 32 Database issue, D64-69.
125. Tsuji, H., Nomiyama, K., Murai, K., Akagi, K. and Fujishima, M. (1992) Comparison of the properties of ribonucleases in human liver tissue and serum. Eur J Clin Chem Clin Biochem, 30, 339-341.

126. Umen, J. G. and Guthrie, C. (1995) The second catalytic step of pre-mRNA splicing. RNA, 1, 869-885.
127. Valcarcel, J., Gaur, R. K., Singh, R. and Green, M. R. (1996) Interaction of U2AF65 RS region with pre-mRNA branch point and promotion of base pairing with U2 snRNA. Science, 273, 1706-1709.
128. Valcarcel, J., Singh, R., Zamore, P. D. and Green, M. R. (1993) The protein Sex-lethal antagonizes the splicing factor U2AF to regulate alternative splicing of transformer pre-mRNA. Nature, 362, 171-175.
129. van Nues, R. W. and Beggs, J. D. (2001) Functional contacts with a range of splicing proteins suggest a central role for Brr2p in the dynamic control of the order of events in spliceosomes of Saccharomyces cerevisiae. Genetics, 157, 1451-1467.
130. Venables, J. P. (2004) Aberrant and alternative splicing in cancer. Cancer Res, 64, 7647-7654.
131. Villemaire, J., Dion, I., Elela, S. A. and Chabot, B. (2003) Reprogramming alternative pre-messenger RNA splicing through the use of protein-binding antisense oligonucleotides. J Biol Chem, 278, 50031-50039.
132. Vortler, L. C. and Eckstein, F. (2000) Phosphorothioate modification of RNA for stereochemical and interference analyses. Methods Enzymol, 317, 74-91.
133. Wallis, M. G., von Ahsen, U., Schroeder, R. and Famulok, M. (1995) A novel RNA motif for neomycin recognition. Chem Biol, 2, 543-552.
134. Wang, Y. and Rando, R. R. (1995) Specific binding of aminoglycoside antibiotics to RNA. Chem Biol, 2, 281-290.
135. Wassarman, D. A. and Steitz, J. A. (1992) Interactions of small nuclear RNA's with precursor messenger RNA during in vitro splicing. Science, 257, 1918-1925.
136. Watakabe, A., Tanaka, K. and Shimura, Y. (1993) The role of exon sequences in splice site selection. Genes Dev., 7, 407-418.
137. Will, C. L. and Luhrmann, R. (1997) Protein functions in pre-mRNA splicing. Curr Opin Cell Biol, 9, 320-328.
138. Wu, S., Romfo, C. M., Nilsen, T. W. and Green, M. R. (1999) Functional recognition of the 3' splice site AG by the splicing factor U2AF35. Nature, 402, 832-835.
139. Xerri, L., Parc, P., Brousset, P., Schlaifer, D., Hassoun, J., Reed, J. C., Krajewski, S, and Birnbaum, D. (1996) Predominant expression of the long isoform of Bcl-x (Bcl-xL) in human lymphomas. Br J Haematol, 92, 900-906.
140. Zamore, P. D., Patton, J. G. and Green, M. R. (1992) Cloning and domain structure of the mammalian splicing factor U2AF. Nature, 355, 609-614.
141. Zhao, Y. and Baranger, A. M. (2003) Design of an adenosine analogue that selectively improves the affinity of a mutant U1A protein for RNA. J Am Chem Soc, 125, 2480-2488.
142. Zhuang, Y. and Weiner, A. M. (1986) A compensatory base change in U1 snRNA suppresses a 5' splice site mutation. Cell, 46, 827-835.
143. Zillmann, M., Zapp, M. L. and Berget, S. M. (1988) Gel electrophoretic isolation of splicing complexes containing U1 small nuclear ribonucleoprotein particles. Mol Cell Biol, 8, 814-821.
144. Zimmermann, G. R., Jenison, R. D., Wick, C. L., Simorre, J. P. and Pardi, A. (1997) Interlocking structural motifs mediate molecular discrimination by a theophylline-binding RNA. Nat Struct Biol, 4, 644-649.
145. Zimmermann, G. R., Shields, T. P., Jenison, R. D., Wick, C. L. and Pardi, A. (1998) A semiconserved residue inhibits complex formation by stabilizing interactions in the free state of a theophylline-binding RNA. Biochemistry, 37, 9186-9192.
146. Zimmermann, G. R., Wick, C. L., Shields, T. P., Jenison, R. D. and Pardi, A. (2000) Molecular interactions and metal binding in the theophylline-binding core of an RNA aptamer. Rna, 6, 659-667.
147. Zorio, D. A. and Blumenthal, T. (1999) Both subunits of U2AF recognize the 3' splice site in Caenorhabditis elegans. Nature, 402, 835-838.
148. Zuker, M. (1989) Computer prediction of RNA structure. Methods Enzymol, 180, 262-288.

What is claimed is:

1. An artificial riboswitch comprising a nucleic acid sequence set forth SEQ ID NO: 6.

2. A nucleic acid comprising the complementary sequence of the nucleic acid sequence in claim 1.

3. A vector comprising the nucleic acid of claim 2.

4. A cell comprising the artificial riboswitch of claim 1 or the nucleic acid of claim 1 or 2.

5. A ligand-dependent riboswitch comprising a theophylline dependent aptamer, wherein the theophylline dependent aptamer is associated with the branchpoint sequence-3' splice region in a pre-mRNA in a nucleic acid sequence set forth as, and the presence of theophylline modulates pre-mRNA splicing.

* * * * *